(12) United States Patent
Wang et al.

(10) Patent No.: US 11,718,613 B2
(45) Date of Patent: *Aug. 8, 2023

(54) N-(PHENYLSULFONYL)BENZAMIDES AND RELATED COMPOUNDS AS BCL-2 INHIBITORS

(71) Applicant: THE REGENTS OF THE UNIVERSITY OF MICHIGAN, Ann Arbor, MI (US)

(72) Inventors: Shaomeng Wang, Superior Township, MI (US); Jianyong Chen, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 65 days.

This patent is subject to a terminal disclaimer.

(21) Appl. No.: 17/023,426

(22) Filed: Sep. 17, 2020

(65) Prior Publication Data
US 2021/0002277 A1  Jan. 7, 2021

Related U.S. Application Data

(63) Continuation of application No. 16/317,056, filed as application No. PCT/US2017/045428 on Aug. 4, 2017, now Pat. No. 10,829,488.

(60) Provisional application No. 62/454,101, filed on Feb. 3, 2017, provisional application No. 62/371,504, filed on Aug. 5, 2016.

(51) Int. Cl.
C07D 471/04 (2006.01)
A61P 35/02 (2006.01)
A61P 35/00 (2006.01)

(52) U.S. Cl.
CPC ............ C07D 471/04 (2013.01); A61P 35/00 (2018.01); A61P 35/02 (2018.01)

(58) Field of Classification Search
CPC .................................................. C07D 471/04
See application file for complete search history.

(56) References Cited

U.S. PATENT DOCUMENTS

| | | | |
|---|---|---|---|
| 8,546,399 B2 | 10/2013 | Bruncko et al. | |
| 8,580,794 B2 | 11/2013 | Doherty et al. | |
| 10,213,433 B2 | 2/2019 | Catron et al. | |
| 10,221,174 B2* | 3/2019 | Wang ...................... | A61P 35/02 |
| 10,327,687 B2 | 6/2019 | Ma et al. | |
| 10,829,488 B2* | 11/2020 | Wang ...................... | A61P 35/00 |
| 2006/0128706 A1 | 6/2006 | Bruncko et al. | |
| 2010/0184766 A1 | 7/2010 | Kunzer et al. | |
| 2010/0305122 A1 | 12/2010 | Bruncko et al. | |
| 2011/0124628 A1* | 5/2011 | Bruncko ................. | A61P 37/06 544/70 |
| 2012/0028925 A1 | 2/2012 | Tao et al. | |
| 2012/0157470 A1 | 6/2012 | Catron et al. | |
| 2015/0329541 A1 | 11/2015 | Bruncko et al. | |

FOREIGN PATENT DOCUMENTS

| | | |
|---|---|---|
| JP | 2012/515224 A | 7/2012 |
| JP | 2013526612 A | 6/2013 |
| JP | 2013540823 A | 11/2013 |

(Continued)

OTHER PUBLICATIONS

Venkatesh, J. Pharm. Sci. 89, 145-154 (2000) (p. 146.*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Adams et al., The Bcl-2 apoptotic switch in cancer development and therapy, Oncogene, 26(9):1324-37 (2007).

(Continued)

Primary Examiner — Nizal S Chandrakumar
(74) Attorney, Agent, or Firm — Marshall, Gerstein & Borun LLP

(57) ABSTRACT

The present disclosure provides compounds having Formula I-A:

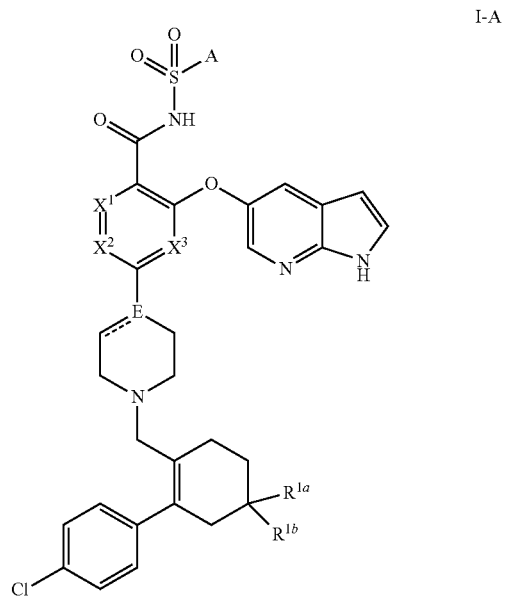

and the pharmaceutically acceptable salts and solvates thereof, wherein A, $X^1$, $X^2$, $X^3$ $R^{1a}$, $R^{1b}$, E, and $=$ are as defined as set forth in the specification. The present disclosure also provides compounds of Formula I-A for use to treat a disease, disorder, or condition responsive to Bcl-2 protein inhibition such as cancer.

16 Claims, 4 Drawing Sheets

(56) References Cited

FOREIGN PATENT DOCUMENTS

| JP | 2013543894 A | 12/2013 |
|---|---|---|
| JP | 2019-506191 A | 3/2019 |
| KR | 2012-0034671 A | 4/2012 |
| WO | WO-2005/049593 A2 | 6/2005 |
| WO | WO-2008/030836 A2 | 3/2008 |
| WO | WO-2008/070663 A2 | 6/2008 |
| WO | WO-2010/065824 A2 | 6/2010 |
| WO | WO-2010/065865 A2 | 6/2010 |
| WO | WO-2010/093742 A1 | 8/2010 |
| WO | WO-2010/138588 A2 | 12/2010 |
| WO | WO-2011/068863 A1 | 6/2011 |
| WO | WO-2011/149492 A1 | 12/2011 |
| WO | WO-2012/058392 A1 | 5/2012 |
| WO | WO-2012/071374 A1 | 5/2012 |

OTHER PUBLICATIONS

Adams et al., The Bcl-2 protein family: arbiters of cell survival, Science, 281(5381):1322-6 (1998).
Amundson et al., An informatics approach identifying markers of chemosensitivity in human cancer cell lines, Cancer Res., 60(21):6101-10 (2000).
Bingham et al., Over one hundred solvates of sulfathiazole, Chem. Commun., 603-4 (2001).
Caira et al., Preparation and crystal characterization of a polymorph, a monohydrate, and an ethyl acetate solvate of the antifungal fluconazole, J. Pharm. Sci., 93(3):601-11 (2004).
Cang et al., ABT-199 (venetoclax) and BCL-2 inhibitors in clinical development, J. Hematol. Oncol., 8:129 (2015).
Cannon, Burger's Medicinal Chemistry and Drug Discovery, Fifth Edition, vol. I: Principles and Practice, Wiley-Interscience, Chapter 19, pp. 783-802 (1995).
Danial et al., Cell death: critical control points, Cell, 116(2):205-19 (2004).
Dorwald, Side Reactions in Organic Synthesis, Wiley: VCH, Weinheim, p. IX of the Preface and pp. 1-15 (2005).
Huang, Fluorescence polarization competition assay: the range of resolvable inhibitor potency is limited by the affinity of the fluorescent ligand, J. Biomol. Screen., 8(1):34-8 (2003).
International Application No. PCT/US2017/045428, International Search Report and Written Opinion, dated Nov. 17, 2017.
Kirkin et al., The role of Bcl-2 family members in tumorigenesis, Biochim. Biophys. Acta, 1644(2-3):229-49 (2004).
Moss, Basic terminology of stereochemistry, Pure & Appl. Chem., 68(12):2193-222 (1996).
Nakayama et al., Targeted disruption of Bcl-2 alpha beta in mice: occurrence of gray hair, polycystic kidney disease, and lymphocytopenia, Proc. Natl. Acad. Sci. USA, 91(9):3700-4 (1994).
Nikolovska-Coleska et al., Development and optimization of a binding assay for the XIAP BIR3 domain using fluorescence polarization, Anal. Biochem., 332(2):261-73 (2004).
Reed et al., BCL-2 family proteins: regulators of cell death involved in the pathogenesis of cancer and resistance to therapy, J. Cell Biochem., 60(1):23-32 (1996).
Reed, Bcl-2 family proteins: strategies for overcoming chemoresistance in cancer, Adv. Pharmacol., 41:501-32 (1997).
Souers et al., ABT-199, a potent and selective BCL-2 inhibitor, achieves antitumor activity while sparing platelets, Nat. Med., 19(2):202-8 (2013).
Tse et al., ABT-263: a potent and orally bioavailable Bcl-2 family inhibitor, Cancer Res., 68(9):3421-8 (2008).
Van Delft et al., The BH3 mimetic ABT-737 targets selective Bcl-2 proteins and efficiently induces apoptosis via Bak/Bax if Mcl-1 is neutralized, Cancer Cell, 10(5):389-99 (2006).
VanTonder et al., Preparation and physicochemical characterization of 5 niclosamide solvates and 1 hemisolvate, AAPS PharmSciTech., 5(1):E12 (2004).
Venkatesh et al., Role of the development scientist in compound lead selection and optimization, J. Pharm. Sci., 89(2):145-54 (Feb. 2000).
West, Solid State Chemistry and Its Applications, John Wiley & Sons (1984).
Willis et al., Apoptosis initiated when BH3 ligands engage multiple Bcl-2 homologs, not Bax or Bak, Science, 315(5813):856-9 (2007).
Zhang, Apoptosis-based anticancer drugs, Nat. Rev. Drug Discov., 1(2):101-2 (2002).

* cited by examiner

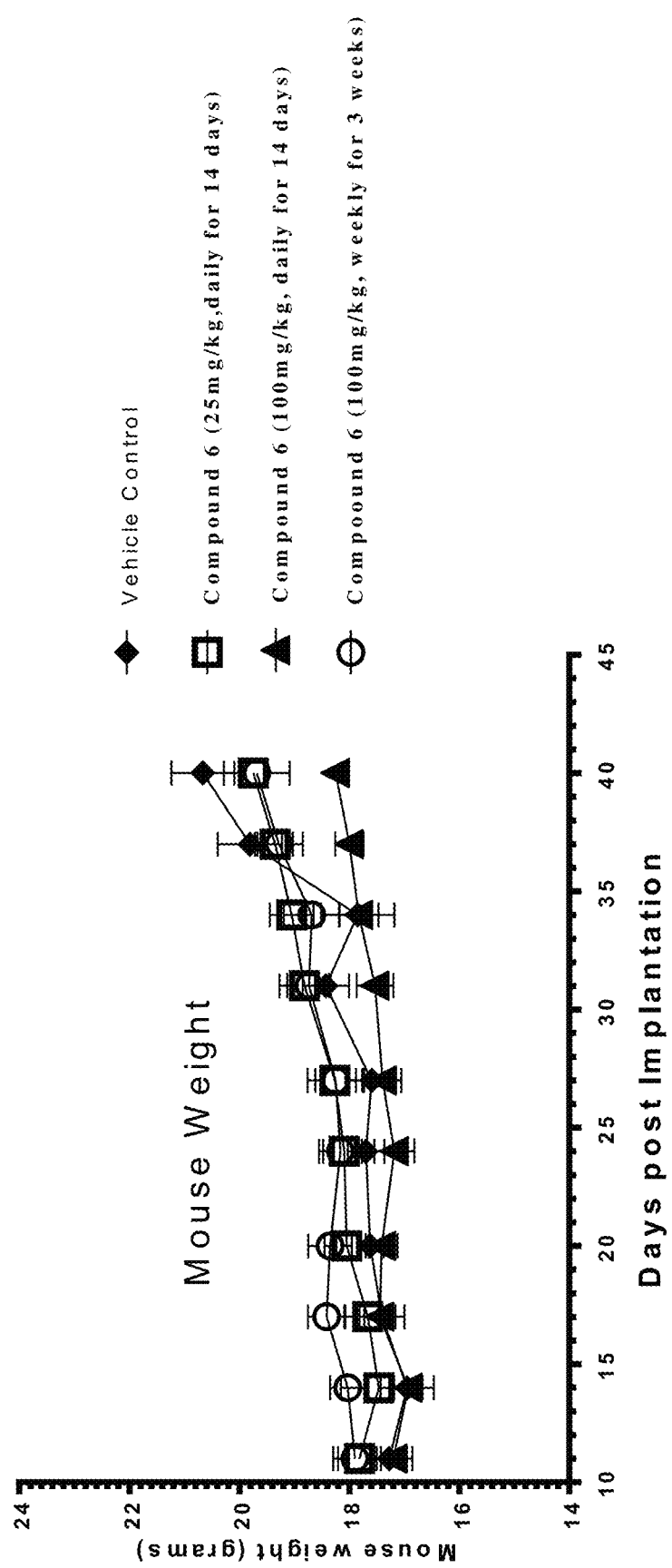

N-(PHENYLSULFONYL)BENZAMIDES AND RELATED COMPOUNDS AS BCL-2 INHIBITORS

CROSS REFERENCE TO RELATED APPLICATIONS

This is a continuation of U.S. application Ser. No. 16/317,056, filed Jan. 11, 2019, which is the U.S. national phase of International Application No. PCT/US2017/045428, filed Aug. 4, 2017, which claims the benefit of U.S. Provisional Patent Application No. 62/454,101 filed Feb. 3, 2017, and U.S. Provisional Patent Application No. 62/371,504, filed Aug. 5, 2016, each incorporated herein by reference in its entirety.

BACKGROUND OF THE INVENTION

Field of the Invention

The present disclosure provides Bcl-2 protein inhibitors and therapeutic methods of treating diseases, disorders, or conditions wherein inhibition of Bcl-2 proteins provides a benefit.

Background

Apoptosis, the process of programmed cell death, is an essential biological process for tissue homeostasis. In mammals, it has been shown to regulate early embryonic development. Later in life, cell death is a default mechanism by which potentially dangerous cells, e.g., cells carrying cancerous defects, are removed. Several apoptotic pathways are known. One of the most important apoptotic pathways involves the Bcl-2 family of proteins which are key regulators of the mitochondrial (also called "intrinsic") pathway of apoptosis. See Danial and Korsmeyer, Cell 116:205-219 (2004). The structural homology domains BH1, BH2, BH3 and BH4 are characteristic of Bcl-2 family proteins. The Bcl-2 family of proteins can be further classified into three subfamilies depending on how many of the homology domains each protein contains and on its biological activity, i.e., whether it has pro- or anti-apoptotic function.

The first subgroup of Bcl-2 proteins contains proteins having all four homology domains, i.e., BH1, BH2, BH3 and BH4. Their general effect is anti-apoptotic, that is to preserve a cell from starting a cell death process. Proteins such as Bcl-2, Bcl-w, Bcl-xL, Mcl-1, and Bfl-1/A1 are members of this first subgroup. Proteins belonging to the second subgroup of Bcl-2 proteins contain the three homology domains BH1, BH2, and BH3, and have a pro-apoptotic effect. The two main representative proteins of this second subgroup are Bax and Bak. The third subgroup of Bcl-2 proteins is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is not entirely known. In one hypothesis of regulation of cell death by Bcl-2 family proteins, the BH3-only proteins are further categorized as either "activator," e.g., Bim and Bid, or "sensitizer," e.g., Bad, Bik, Noxa, Hrk, Bmf, and Puma, proteins depending on their regulatory function.

One of the keys to tissue homeostasis is achieving a balance in the interactions among the three subgroups of Bcl-2 proteins in cells. Studies have elucidated the mechanisms by which pro-apoptotic and anti-apoptotic subgroups of Bcl-2 family proteins interact to allow a cell to undergo programmed cell death. After receiving intra- or extracellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins, e.g., Puma, Bim, Bid, are "activators" in that these proteins directly engage pro-apoptotic proteins Bax and Bak to initiate MOMP, while other BH3-only proteins, e.g., Bad, Bik and Noxa, are "sensitizers" and induce Bax and Bak oligomerization indirectly by binding anti-apoptotic proteins, e.g., Bcl-2, Bcl-xL, Bcl-w, Mcl-1, and displacing and "freeing-up" the "activator" BH3-only proteins, which subsequently bind to and activate pro-apoptotic proteins, e.g., Bax, Bak, to induce cell death. Other research suggests that anti-apoptotic proteins engage and seqeuester Bax and Bak directly and all BH3-only proteins regulates this interaction by binding to anti-apoptotic proteins, e.g., Bcl-2, Bch xL, Bcl-w, Mcl-1, which results in the release Bax and Bak. See Adams and Cory, Oncogene 26:1324-1337 (2007) and Willis et al., Science 315:856-859 (2007). Although the exact interactions through which the anti- and pro-apoptotic Bcl-2 family proteins regulate apoptosis remain under investigation, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

Down-regulated apoptosis (and more particularly the Bcl-2 family of proteins) may be involved in the onset of cancerous malignancy. Research has shown, for example, the anti-apoptotic proteins, Bcl-2 and Bcl-xL, are overexpressed in many cancer cell types. See Zhang, Nature Reviews Drug Discovery 1:101 (2002); Kirkin et al., Biochimica et Biophysica Acta 1644:229-249 (2004); and Amundson et al., Cancer Research 60:6101-6110 (2000). The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings have made possible new strategies in drug discovery for targeting cancer. If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival). Therapeutic strategies for targeting Bcl-2 and Bcl-$X_L$ in cancer to restore cancer cell sensitivity and overcome resistance of cancer cells to apoptosis have been reviewed. See Adams et al., Science 281:1322 (1998) and Reed, Adv. Pharmacol. 41:501 (1997); Reed et al., J. Cell. Biochem. 60:23 (1996).

Platelets also contain the necessary apoptotic machinery, e.g., Bax, Bak, Bcl-xL, Bcl-2, cytochrome c, caspase-9, caspase-3 and APAF-1, to execute programmed cell death through the intrinsic apoptotic pathway. Although circulating platelet production is a normal physiological process, a number of diseases are caused or exacerbated by excess of, or undesired activation of, platelets. This suggests that therapeutic agents capable of inhibiting anti-apoptotic proteins in platelets and reducing the number of platelets in mammals may be useful in treating pro-thrombotic conditions and diseases that are characterized by an excess of, or undesired activation of, platelets.

Small molecule BH3-only protein mimetics such as ABT-737 and ABT-263 bind strongly to a subset of anti-apoptotic Bcl-2 proteins including Bcl-2, Bcl-w and Bcl-xL, and weakly to Mcl-1 and A1. These small molecules were tested in animal studies and demonstrated cytotoxic activity in certain xenograft models as single agents, as well as enhanced the effects of a number of chemotherapeutic agents on other xenograft models when used in combination. See Tse, C. et al., Cancer Res 68: 3421-3428 (2008) and van Delft, M. F. et al., Cancer Cell 10:389-399 (2006). These in vivo studies suggest the potential utility of inhibitors of anti-apoptotic Bcl-2 family proteins for the treatment of diseases that involve a dysregulated apoptotic pathway. ABT-199 (Venetoclax) is a potent Bcl-2 inhibitor that has been approved by the U.S. Food and Drug Administration for the treatment of chronic lymphocytic leukemia. See Cang et al., Journal of Hematology & Oncology 8:129 (2015) and Souers et al., Nature Medicine 19:202-208 (2013).

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal, i.e., non-cancerous, cells, and the recognized inter-cell type variability of Bcl-2 family protein expression, it is advantageous to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others, e.g., lymphopenia has been observed in Bcl-2 deficient mice. See Nakayama, K. et al. PNAS 91:3700-3704 (1994).

There is an ongoing need for small molecules that selectively inhibit the activity of one type or a subset of Bcl-2 proteins for the treatment of hyperproliferative diseases such as cancer.

BRIEF SUMMARY OF THE INVENTION

In one aspect, the present disclosure provides compounds represented by any one of Formulae I-A or I-VIII, below, and the pharmaceutically acceptable salts and solvates, e.g., hydrates, thereof, collectively referred to herein as "Compounds of the Disclosure."

In another aspect, the present disclosure provides a pharmaceutical composition comprising a Compound of the Disclosure and one or more pharmaceutically acceptable carriers.

In another aspect, the present disclosure provides a method of inhibiting Bcl-2 proteins, e.g., Bcl-2, Bcl-w, Bcl-xL, Mcl-1, and Bfl-1/A1, or any combination thereof, in a subject, e.g., a human, comprising administering to the subject an effective amount of at least one Compound of the Disclosure.

In another aspect, the present disclosure provides methods for treating or preventing diseases, disorders, or conditions, e.g., a hyperproliferative disease, e.g., cancer, e.g., small cell lung cancer, non-Hodgkin's lymphoma (NHL), acute myelogenous leukemia (AML), chronic lymphoid (or lymphocytic) leukemia (CLL), or acute lymphoblastic leukemia (ALL), in a subject responsive to inhibition of Bcl-2 proteins, e.g., Bcl-2 and/or Bcl-xL, comprising administering to the subject a therapeutically effective amount of a Compound of the Disclosure.

In another aspect, the present disclosure provides the use of Compounds of the Disclosure as inhibitors of one or more Bcl-2 proteins, e.g., Bcl-2 and/or Bcl-xL.

In another aspect, the present disclosure provides the use of Compounds of the Disclosure as inhibitors of Bcl-2.

In another aspect, the present disclosure provides the use of Compounds of the Disclosure as inhibitors of Bcl-xL.

In another aspect, the present disclosure provides a pharmaceutical composition for treating diseases, disorders, or conditions responsive to inhibition of Bcl-2 proteins, e.g., Bcl-2 and/or Bcl-xL, wherein the pharmaceutical composition comprises a therapeutically effective amount of a Compound of the Disclosure optionally admixed with one or more pharmaceutically acceptable carriers.

In another aspect, the present disclosure provides Compounds of the Disclosure for use in treating or preventing a disease, disorder, or condition, e.g., a hyperproliferative disease, e.g., cancer, in a subject, e.g., a human.

In another aspect, the present disclosure provides a Compound of the Disclosure for use in the manufacture of a medicament for treating a disease, disorder, or condition, e.g., a hyperproliferative disease, e.g., cancer, in a subject, e.g., a human.

In another aspect, the present disclosure provides kit comprising a Compound of the Disclosure.

In another aspect, the present disclosure provides a kit comprising a Compound of the Disclosure and a second therapeutic agent useful in the treatment of a disease, disorder, or condition of interest, and a package insert containing directions for use in the treatment of that disease, disorder, or condition.

In another aspect, the present disclosure provides a composition comprising: (a) a Compound of the Disclosure; (b) a second therapeutically active agent; and (c) optionally an excipient and/or pharmaceutically acceptable carrier.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF DRAWINGS

FIG. 4 is a line graph showing the mouse weight following administration of Cpd. No. 6 in the RS4;11 leukemia xenograft model.

DETAILED DESCRIPTION OF THE INVENTION

Figure 1:
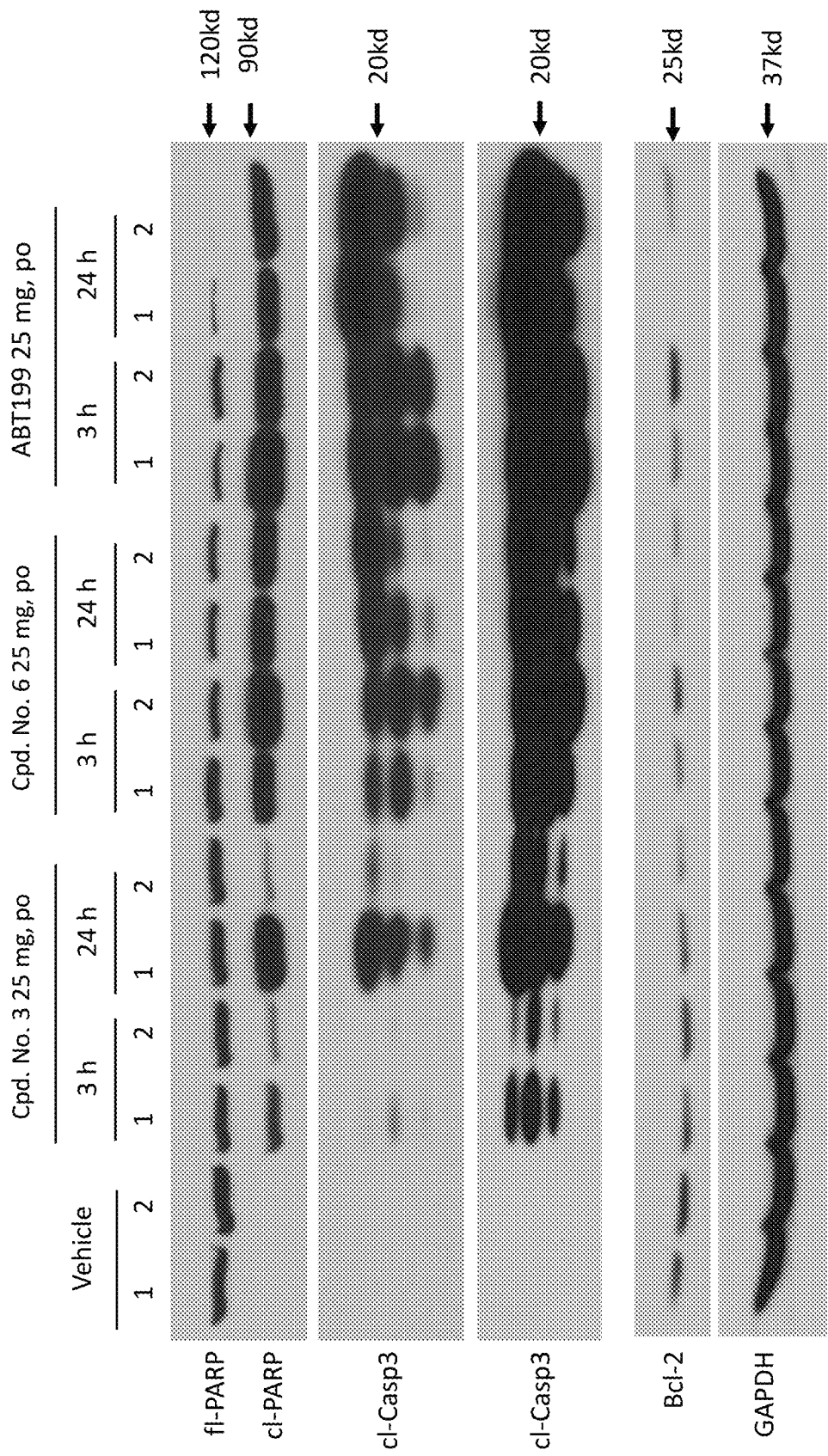
FIG. 1 is an illustration (Western blotting analysis) showing the expression of PARP, cleaved caspase-3, and Bcl-2 in RS4;11 xenograft tumor tissues obtained from mice following administration of Compounds of the Disclosure and ABT-199.

Compounds of the Disclosure inhibit Bcl-2 proteins, e.g., Bcl-2 and/or Bcl-xL. In view of this property, Compounds of the Disclosure are useful for treating or preventing diseases, disorders, or conditions, e.g., a hyperproliferative disease, e.g., cancer, responsive to the inhibition of Bcl-2 proteins in a subject. Cancers responsive to the inhibition of Bcl-2 proteins include, but are not limited to, small cell lung cancer, NHL, AML, CLL, and ALL.

In one embodiment, Compounds of the Disclosure are compounds having Formula I-A:

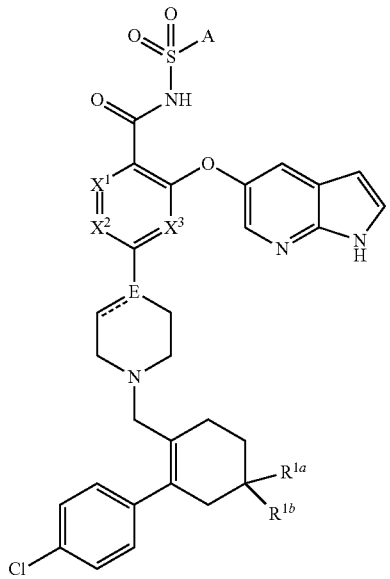

I-A or a pharmaceutically acceptable salt or solvate thereof, wherein:

A is selected from the group consisting of:

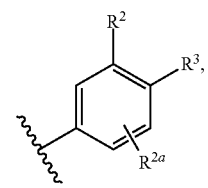

A-1

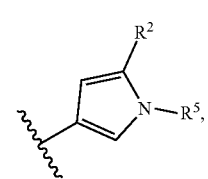

A-2

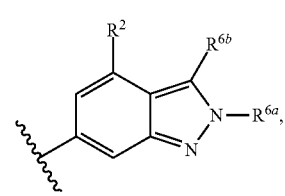

A-3

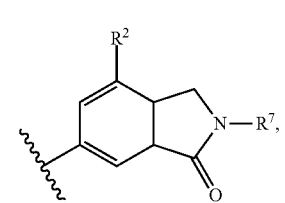

A-4

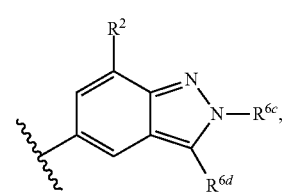

A-5

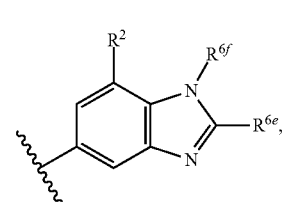

A-6

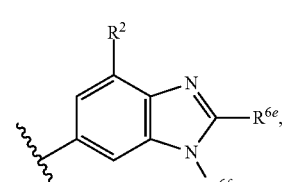

A-7

-continued

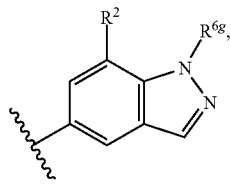
A-8

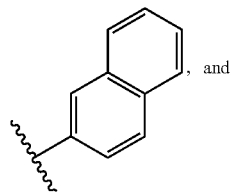
A-9 and

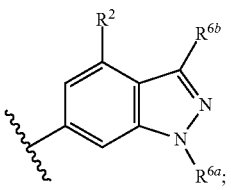
A-10

E is a carbon atom and ═ is a double bond; or
E is a —C(H)— and ═ is a single bond; or
E is a nitrogen atom and ═ is a single bond;
$X^1$, $X^2$, and $X^3$ are each independently selected from the group consisting of —$CR^8$═ and —N═;
$R^{1a}$ and $R^{1b}$ taken together with the carbon atom to which they are attached form a 3-, 4-, or 5-membered optionally substituted cycloalkyl; or
$R^{1a}$ and $R^{1b}$ taken together with the carbon atom to which they are attached form a 4- or 5-membered optionally substituted heterocyclo;
$R^2$ is selected from the group consisting of —$NO_2$, —$SO_2CH_3$, and —$SO_2CF_3$;
$R^{2a}$ is selected from the group consisting of hydrogen and halogen;
$R^3$ is selected from the group consisting of hydrogen, —CN, —C≡CH, and —N($R^{4a}$)($R^{4b}$);
$R^{4a}$ is selected from the group consisting of optionally substituted $C_{1-6}$ alkyl, optionally substituted $C_{3-6}$ cycloalkyl, heterocyclo, heteroalkyl, (cycloalkyl)alkyl, and (heterocyclo)alkyl;
$R^{4b}$ is selected from the group consisting of hydrogen and $C_{1-4}$ alkyl;
$R^5$ is selected from the group consisting of is selected from the group consisting of optionally substituted $C_{1-6}$ alkyl, heterocyclo, heteroalkyl, (cycloalkyl)alkyl, and (heterocyclo)alkyl;
$R^{6a}$, $R^{6c}$, $R^{6e}$, $R^{6f}$, and $R^{6g}$ are each independently selected from the group consisting of hydrogen, optionally substituted $C_{1-6}$ alkyl, optionally substituted $C_{3-6}$ cycloalkyl, optionally substituted aryl, optionally substituted heteroaryl, heterocyclo, heteroalkyl, (cycloalkyl)alkyl, and (heterocyclo)alkyl;
$R^{6b}$ and $R^{6d}$ are each independently selected from the group consisting of hydrogen, $C_{1-4}$ alkyl, and halogen;
$R^7$ is selected from the group consisting of optionally substituted $C_{1-6}$ alkyl, heterocyclo, heteroalkyl, (cycloalkyl)alkyl, and (heterocyclo)alkyl; and
$R^8$ is selected from the group consisting of hydrogen and halogen.

In another embodiment, Compounds of the Disclosure are compounds having Formula I-A, wherein:

A is selected from the group consisting of A-1, A-2, A-3, A-4, A-5, A-6, A-7, A-8, and A-9;

$R^{4a}$ is selected from the group consisting of optionally substituted $C_{1-6}$ alkyl, heterocyclo, heteroalkyl, (cycloalkyl)alkyl, and (heterocyclo)alkyl; and $R^{6a}$, $R^{6c}$, $R^{6e}$, $R^{6f}$, and $R^{6g}$ are each independently selected from the group consisting of hydrogen, optionally substituted $C_{1-6}$ alkyl, heterocyclo, heteroalkyl, (cycloalkyl) alkyl, and (heterocyclo)alkyl.

In another embodiment, Compounds of the Disclosure are compounds having Formula I:

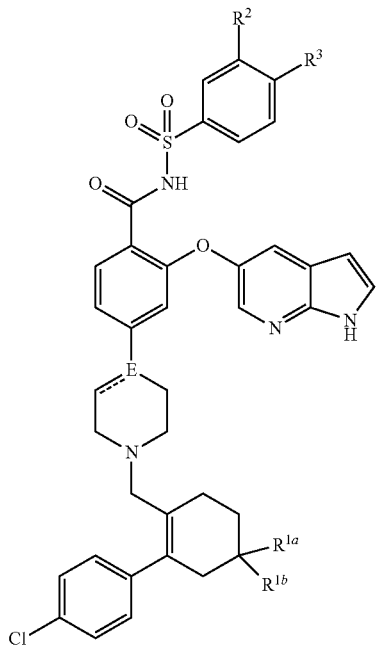
I or a pharmaceutically acceptable salt or solvate thereof, wherein:

E is a carbon atom and ═ is a double bond; or

E is a —C(H)— and ═ is a single bond; or

E is a nitrogen atom and ═ is a single bond;

$R^{1a}$ and $R^{1b}$ taken together with the carbon atom to which they are attached form a 3-, 4-, or 5-membered optionally substituted cycloalkyl; or $R^{1a}$ and $R^{1b}$ taken together with the carbon atom to which they are attached form a 4- or 5-membered optionally substituted heterocyclo;

$R^2$ is selected from the group consisting of —$NO_2$, —$SO_2CH_3$, and —$SO_2CF_3$;

$R^3$ is selected from the group consisting of hydrogen, —CN, —C≡CH, and —N($R^{4a}$)($R^{4b}$);

$R^{4a}$ is selected from the group consisting of optionally substituted $C_{1-6}$ alkyl, heterocyclo, (cycloalkyl)alkyl, and (heterocyclo)alkyl; and $R^{4b}$ is selected from the group consisting of hydrogen and $C_{1-4}$ alkyl.

In another embodiment, Compounds of the Disclosure are compounds having Formula II:

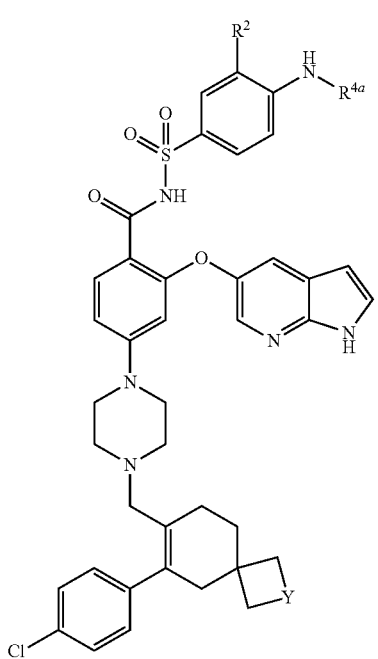

II or a pharmaceutically acceptable salt or solvate thereof, wherein Y selected from the group consisting of —CH$_2$— and —O—, and R$^2$ and R$^{4a}$ are as defined in connection with Formula I.

In another embodiment, Compounds of the Disclosure are compounds having Formula III:

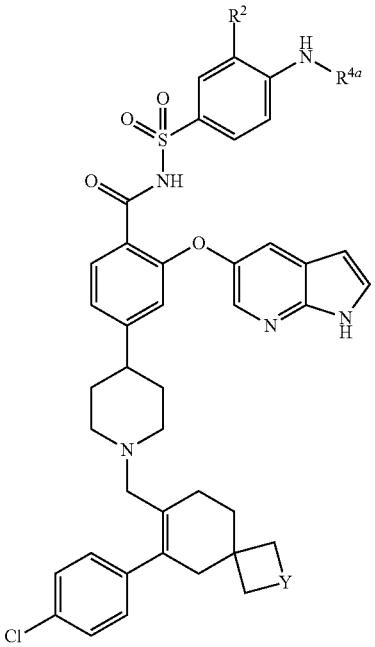

III or a pharmaceutically acceptable salt or solvate thereof, wherein Y selected from the group consisting of —CH$_2$— and —O—, and R$^2$ and R$^{4a}$ are as defined in connection with Formula I.

In another embodiment, Compounds of the Disclosure are compounds having Formula IV:

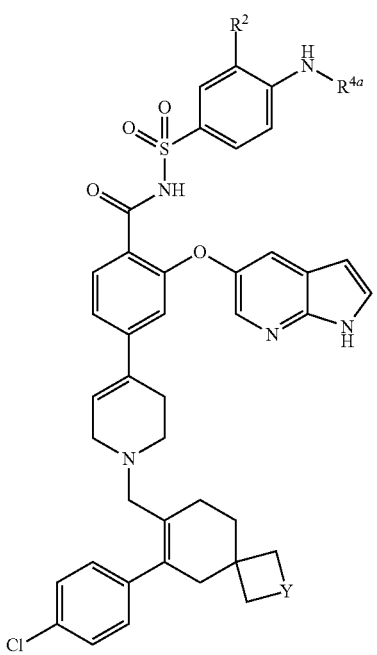

IV or a pharmaceutically acceptable salt or solvate thereof, wherein Y selected from the group consisting of —CH$_2$— and —O—, and R$^2$ and R$^{4a}$ are as defined in connection with Formula I.

In another embodiment, Compounds of the Disclosure are compounds having Formula V:

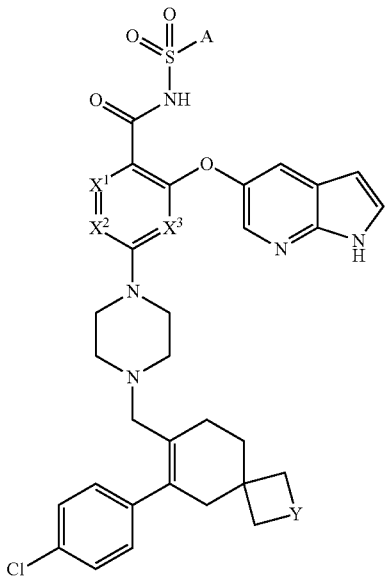

V or a pharmaceutically acceptable salt or solvate thereof, wherein Y selected from the group consisting of —CH$_2$— and —O—, and A, X$^1$, X$^2$, and X$^3$ are as defined in connection with Formula I-A.

In another embodiment, Compounds of the Disclosure are compounds having Formula VI:

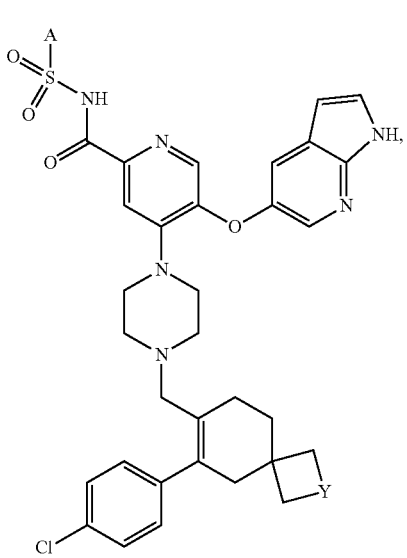

or a pharmaceutically acceptable salt or solvate thereof, wherein Y selected from the group consisting of —CH$_2$— and —O—, and A is as defined in connection with Formula I-A.

In another embodiment, Compounds of the Disclosure are compounds having Formula I-A, V, or VI, or a pharmaceutically acceptable salt or solvate thereof, wherein A is A-1.

In another embodiment, Compounds of the Disclosure are compounds having Formula I-A, V, or VI, or a pharmaceutically acceptable salt or solvate thereof, wherein A is A-2.

In another embodiment, Compounds of the Disclosure are compounds having Formula I-A, V, or VI, or a pharmaceutically acceptable salt or solvate thereof, wherein A is A-3.

In another embodiment, Compounds of the Disclosure are compounds having Formula I-A, V, or VI, or a pharmaceutically acceptable salt or solvate thereof, wherein A is A-4.

In another embodiment, Compounds of the Disclosure are compounds having Formula I-A, V, or VI, or a pharmaceutically acceptable salt or solvate thereof, wherein A is A-5.

In another embodiment, Compounds of the Disclosure are compounds having Formula I-A, V, or VI, or a pharmaceutically acceptable salt or solvate thereof, wherein A is A-6.

In another embodiment, Compounds of the Disclosure are compounds having Formula I-A, V, or VI, or a pharmaceutically acceptable salt or solvate thereof, wherein A is A-7.

In another embodiment, Compounds of the Disclosure are compounds having Formula I-A, V, or VI, or a pharmaceutically acceptable salt or solvate thereof, wherein A is A-8.

In another embodiment, Compounds of the Disclosure are compounds having Formula I-A, V, or VI, or a pharmaceutically acceptable salt or solvate thereof, wherein A is A-9.

In another embodiment, Compounds of the Disclosure are compounds having Formula I-A, V, or VI, or a pharmaceutically acceptable salt or solvate thereof, wherein A is A-10.

In another embodiment, Compounds of the Disclosure are compounds having Formula VII:

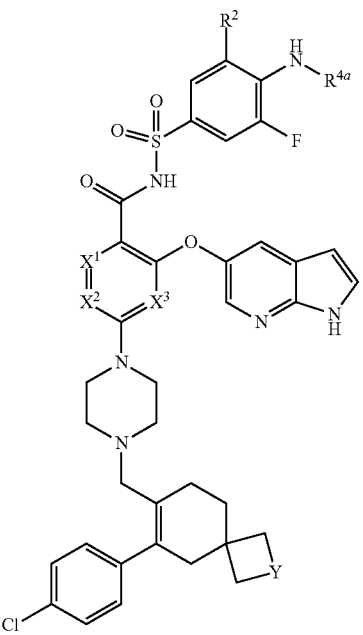

or a pharmaceutically acceptable salt or solvate thereof, wherein Y selected from the group consisting of —CH$_2$— and —O—, and $X^1$, $X^2$, $X^3$, $R^2$, and $R^{4a}$ are as defined in connection with Formula I-A.

In another embodiment, Compounds of the Disclosure are compounds having Formula I-A, V, or VII, or a pharmaceutically acceptable salt or solvate thereof, wherein $X^1$, $X^2$, and $X^3$ are each —CH=.

In another embodiment, Compounds of the Disclosure are compounds having Formula I-A, V, or VII, or a pharmaceutically acceptable salt or solvate thereof, wherein $X^1$ is —CF=, and $X^2$ and $X^3$ are each —CH=.

In another embodiment, Compounds of the Disclosure are compounds having Formula I-A, V, or VII, or a pharmaceutically acceptable salt or solvate thereof, wherein $X^1$ and $X^3$ are each —CH=, and $X^2$ is —CF=.

In another embodiment, Compounds of the Disclosure are compounds having Formula I-A, V, or VII, or a pharmaceutically acceptable salt or solvate thereof, wherein $X^1$ and $X^2$ are each —CH=, and $X^3$ is —CF=.

In another embodiment, Compounds of the Disclosure are compounds having Formula I-A, V, or VII, or a pharmaceutically acceptable salt or solvate thereof, wherein $X^1$ is —N=, and $X^2$ and $X^3$ are each —CH=.

In another embodiment, Compounds of the Disclosure are compounds having Formula I-A, V, or VII, or a pharmaceutically acceptable salt or solvate thereof, wherein $X^1$ and $X^3$ are each —CH=, and $X^2$ is —N=.

In another embodiment, Compounds of the Disclosure are compounds having Formula I-A, V, or VII, or a pharmaceutically acceptable salt or solvate thereof, wherein $X^1$ and $X^2$ are each —CH=, and $X^3$ is —N=.

In another embodiment, Compounds of the Disclosure are compounds having any one of Formulae II-VII, or a pharmaceutically acceptable salt or solvate thereof, wherein Y is —O—.

In another embodiment, Compounds of the Disclosure are compounds having any one of Formulae II-VII, or a pharmaceutically acceptable salt or solvate thereof, wherein Y is —CH$_2$—.

In another embodiment, Compounds of the Disclosure are compounds having any one of Formulae I-A or I-VII, or a pharmaceutically acceptable salt or solvate thereof, wherein R$^2$ is —NO$_2$.

In another embodiment, Compounds of the Disclosure are compounds having any one of Formulae I-IV, or a pharmaceutically acceptable salt or solvate thereof, wherein R$^{4a}$ is selected from the group consisting of:

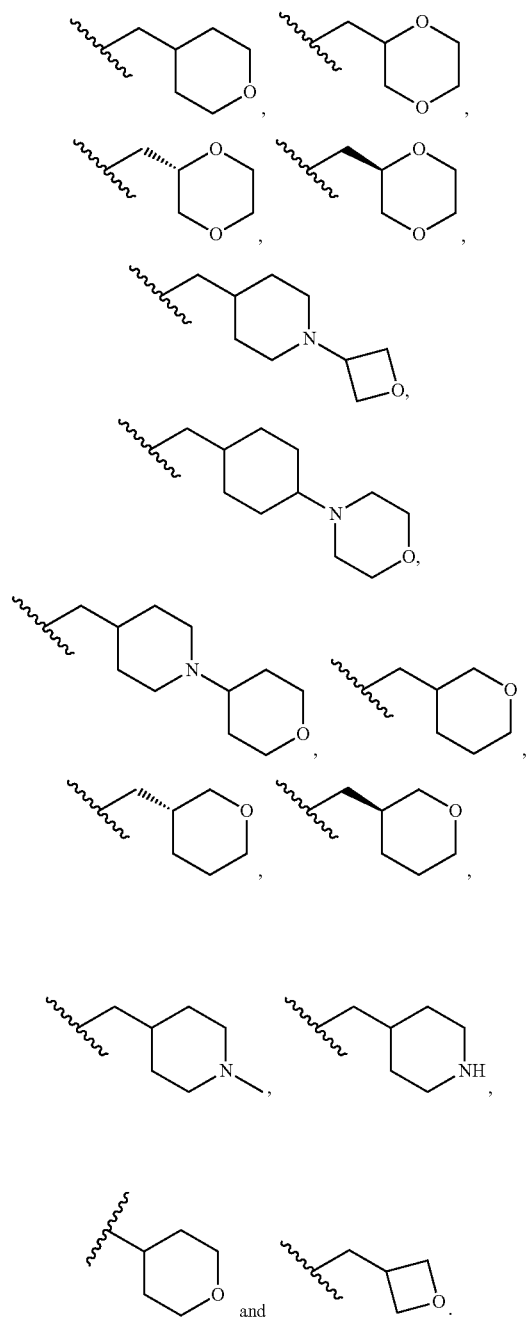

In another embodiment, Compounds of the Disclosure are compounds having any one of Formulae I-A or V-VII, or a pharmaceutically acceptable salt or solvate thereof, wherein R$^{4a}$, R$^5$, R$^{6a}$, and R$^7$ are each independently selected from the group consisting of:

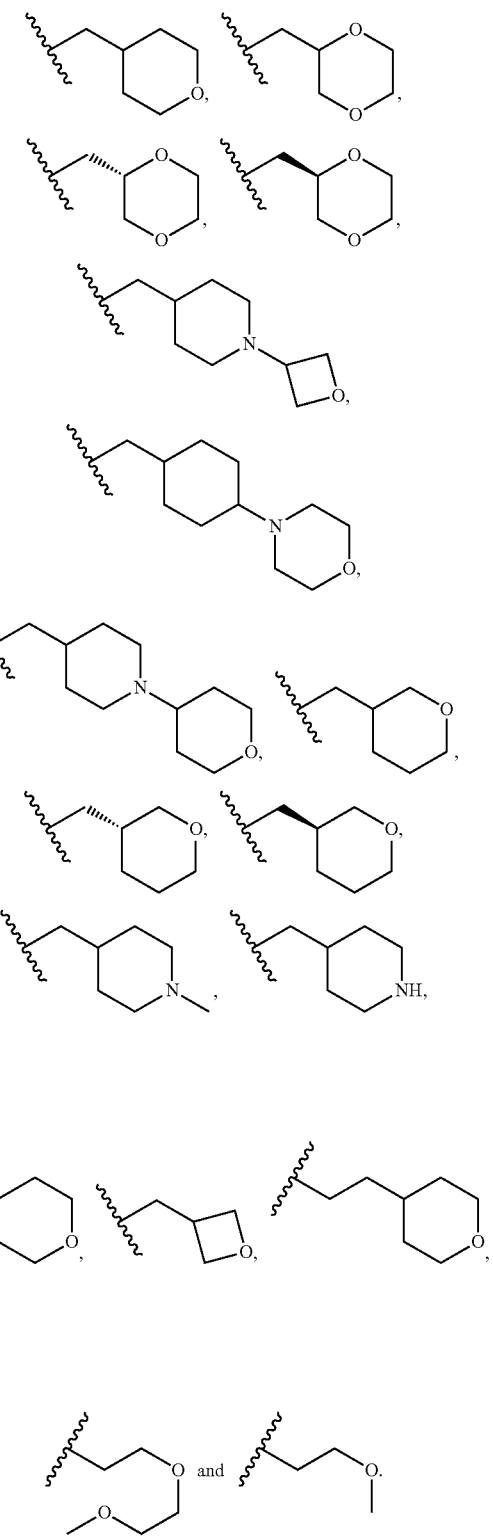

In another embodiment, Compounds of the Disclosure are compounds having Formula VIII:

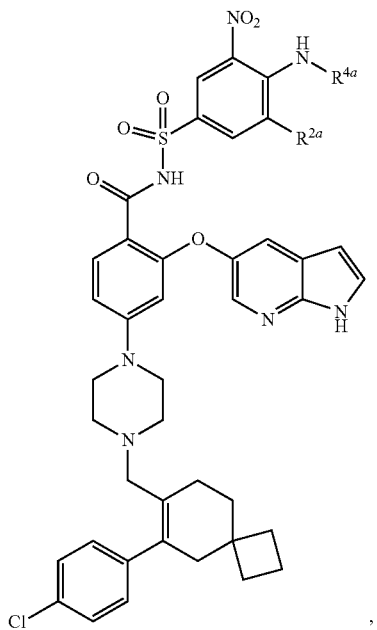

VIII or a pharmaceutically acceptable salt or solvate thereof, wherein $R^e a$ is hydrogen or fluoro and $R^{4a}$ is as defined in connection with Formula I-A.

In another embodiment, Compounds of the Disclosure are compounds having Formula VIII, or a pharmaceutically acceptable salt or solvate thereof, wherein $R^{4a}$ is selected from the group consisting of:

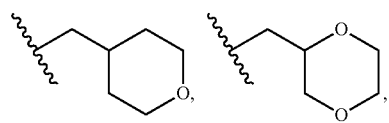

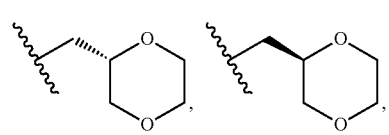

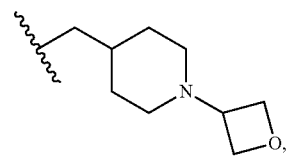

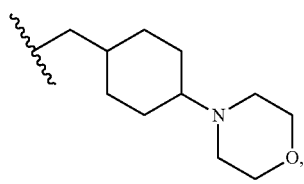

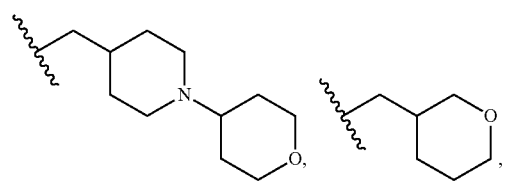

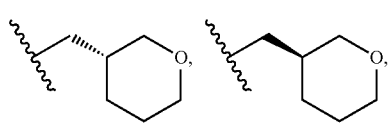

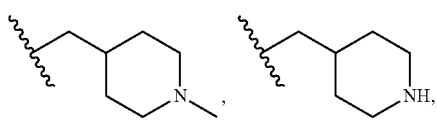

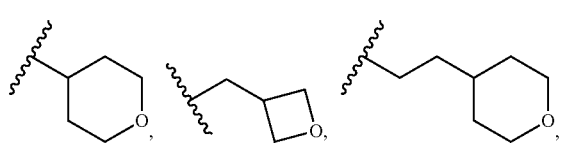

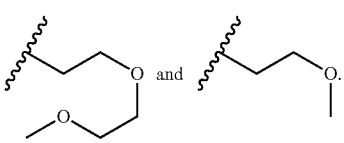

In another embodiment, Compounds of the Disclosure are compounds selected from one or more of the compounds of Table 1, or a pharmaceutically acceptable salt or solvate thereof.

TABLE 1

| Cpd. No. | Structure | Name |
|---|---|---|
| 1 | 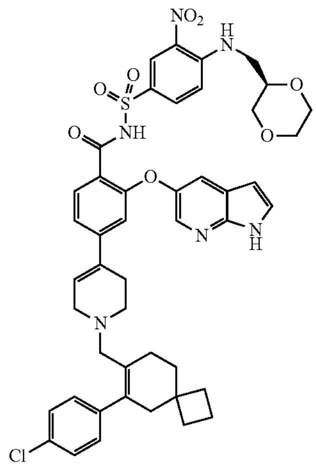 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide |
| 2 | 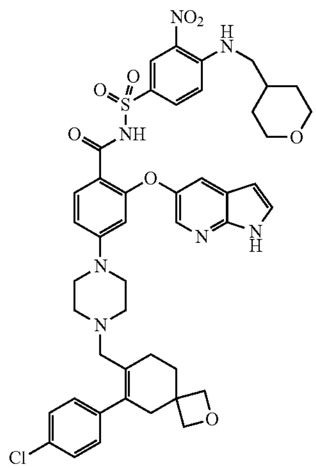 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1] | 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide |
| 3 | 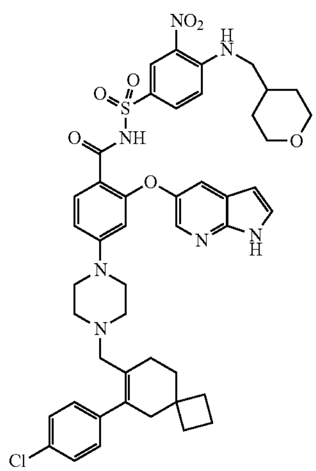 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 4 | 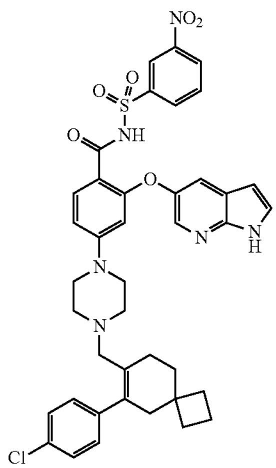 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitrophenyl)sulfonyl)benzamide |
| 5 | 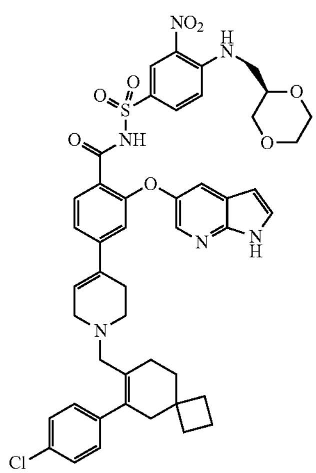 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide |
| 6 | 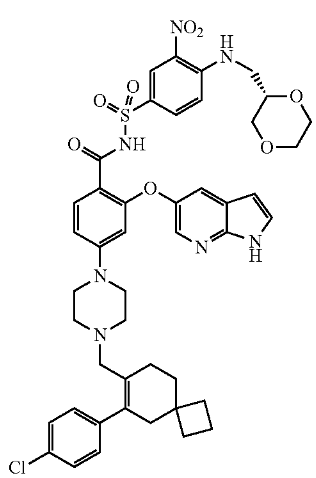 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-continued

| Cpd. No. | Structure | Name |
|---|---|---|
| 7 | 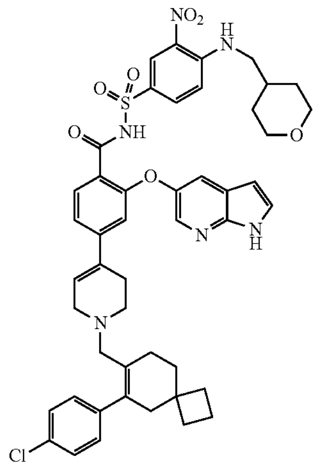 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |
| 8 | 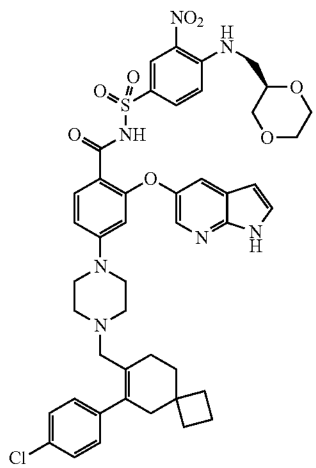 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide |
| 9 | 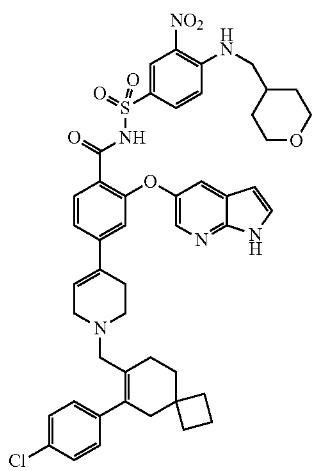 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 10 | 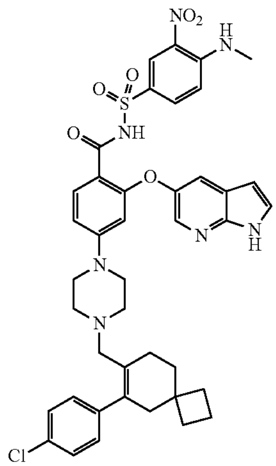 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(methylamino)-3-nitrophenyl)sulfonyl)benzamide |
| 11 | 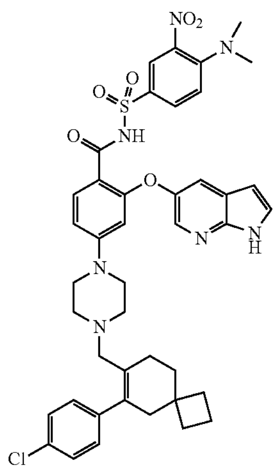 [SMILES: CN(C)c1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(dimethylamino)-3-nitrophenyl)sulfonyl)benzamide |
| 12 | 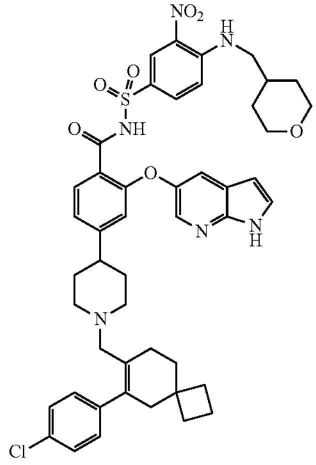 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide |

TABLE 1-continued

| Cpd. No. | Structure | Name |
|---|---|---|
| 13 | 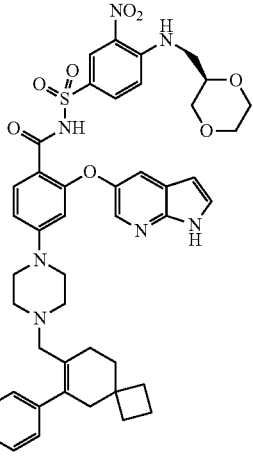 | (R)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 14 | 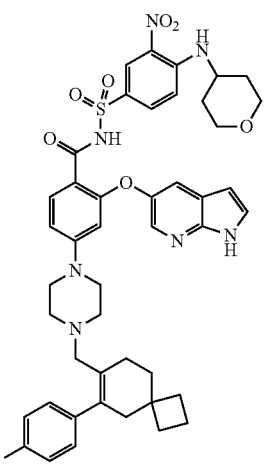 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((tetrahydro-2H-pyran-4-yl)amino)phenyl)sulfonyl)benzamide |
| 15 | 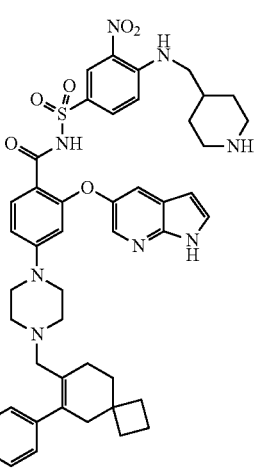 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((piperidin-4-ylmethyl)amino)phenyl)sulfonyl)benzamide |

TABLE 1-continued

| Cpd. No. | Structure | Name |
|---|---|---|
| 16 | 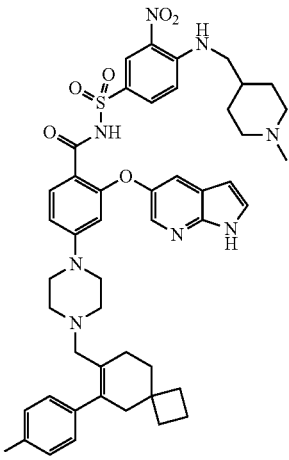 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-(((1-methylpiperidin-4-yl)methyl)amino)-3-nitrophenyl)sulfonyl)benzamide |
| 17 | 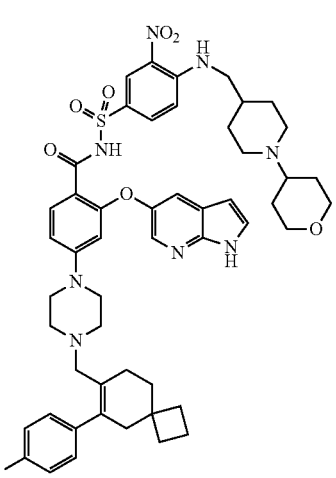 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(tetrahydro-2H-pyran-4-yl)piperidin-4-yl)methyl)amino)phenyl)sulfonyl)benzamide |
| 18 | 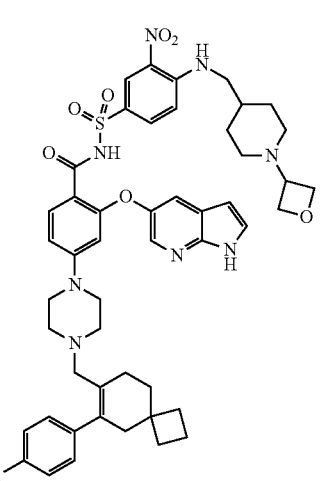 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((1-(oxetan-3-yl)piperidin-4-yl)methyl)amino)phenyl)sulfonyl)benzamide |

TABLE 1-continued

| Cpd. No. | Structure | Name |
|---|---|---|
| 19 | 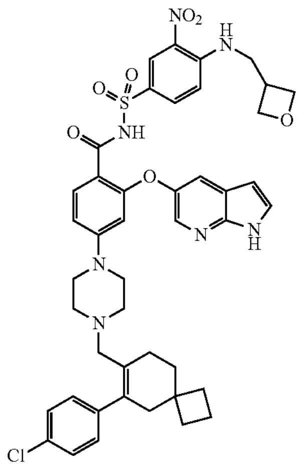 [SMILES: O=C(NS(=O)(=O)c1ccc(NCC2COC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-((oxetan-3-ylmethyl)amino)phenyl)sulfonyl)benzamide |
| 20 | 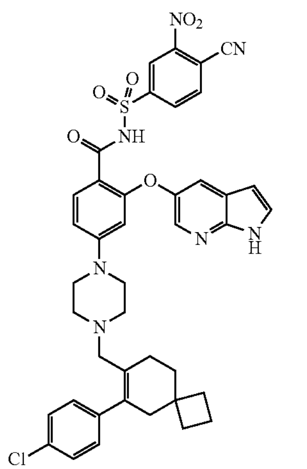 [SMILES: N#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-cyano-3-nitrophenyl)sulfonyl)benzamide |
| 21 | 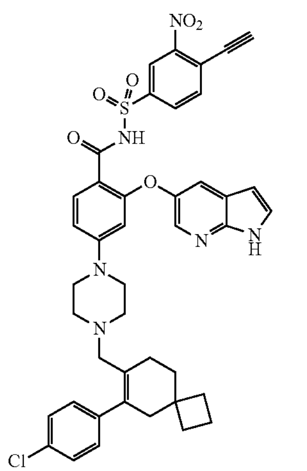 [SMILES: C#Cc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-ethynyl-3-nitrophenyl)sulfonyl)benzamide |

In another embodiment, Compounds of the Disclosure are compounds selected from one or more of the compounds of Table 1-A, or a pharmaceutically acceptable salt or solvate thereof.

TABLE 1-A

| Cpd. No. | Structure | Name |
|---|---|---|
| 22 | 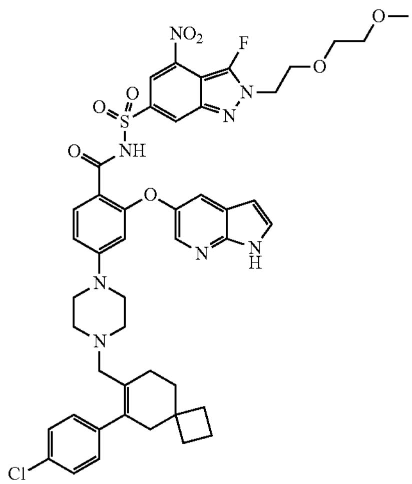 [SMILES: COCCOCCn1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2c1F] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-2-(2-(2-methoxyethoxy)ethyl)-4-nitro-2H-indazol-6-yl)sulfonyl)benzamide |
| 23 | 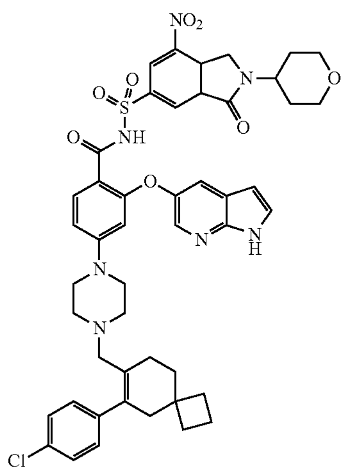 [SMILES: O=C(NS(=O)(=O)C1=CC2C(=O)N(C3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-(tetrahydro-2H-pyran-4-yl)-2,3,3a,7a-tetrahydro-1H-isoindol-5-yl)sulfonyl)benzamide |
| 24 | 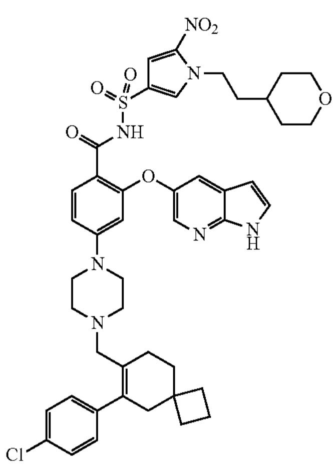 [SMILES: O=C(NS(=O)(=O)c1cc([N+](=O)[O-])n(CCC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-(2-(tetrahydro-2H-pyran-4-yl)ethyl)-1H-pyrrol-3-yl)sulfonyl)benzamide |

TABLE 1-A-continued

| Cpd. No. | Structure | Name |
|---|---|---|
| 25 | 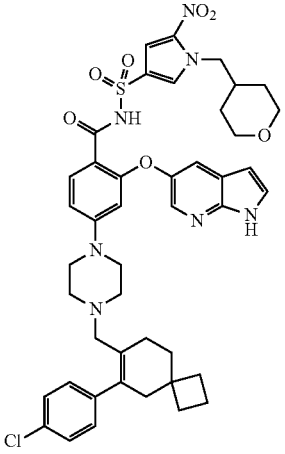 [SMILES: O=C(NS(=O)(=O)c1cc([N+](=O)[O-])n(CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl) sulfonyl)benzamide |
| 26 | 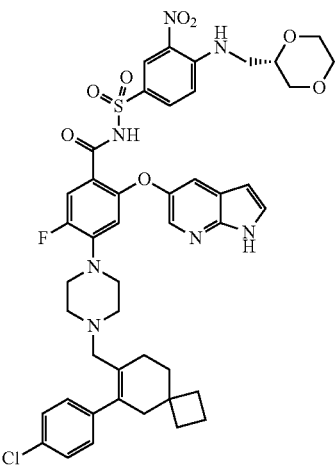 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |
| 27 | 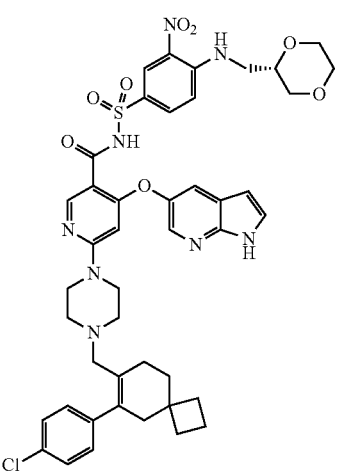 [SMILES: O=C(NS(=O)(=O)c1ccc(NC[C@H]2COCCO2)c([N+](=O)[O-])c1)c1cnc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-3-((1H-pyrrolo[2,3-b]pyridin-5-yl)oxy)-5-(4-((6-(4-chlorophenyl)spiro[3.5]non-6-en-7-yl)methyl)piperazin-1-yl)picolinamide |

TABLE 1-A-continued

| Cpd. No. | Structure | Name |
|---|---|---|
| 28 | 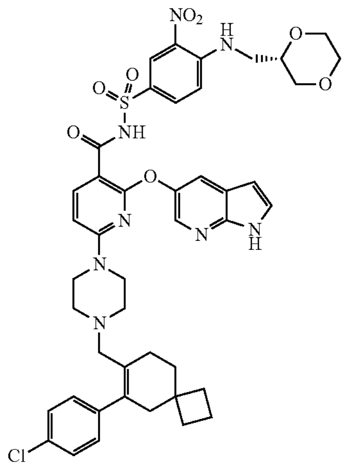 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)nc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-6-(4-((6-(4-chlorophenyl)spiro[3.5]non-6-en-7-yl)methyl)piperazin-1-yl)nicotinamide |
| 29 | 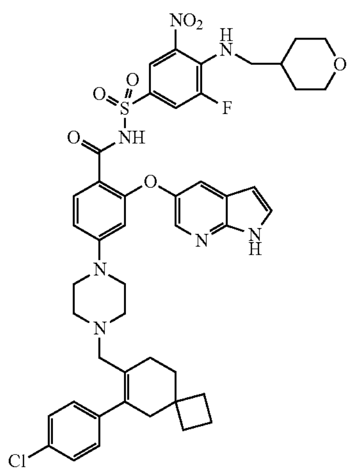 [SMILES: O=C(NS(=O)(=O)c1cc(F)c(NCC2CCOCC2)c([N+](=O)[O-])c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-fluoro-5-nitro-4-(((tetrahydro-2H-pyran-4-yl)methyl)amino)phenyl)sulfonyl)benzamide |
| 30 | 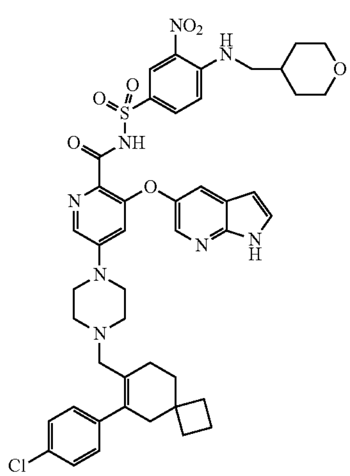 [SMILES: O=C(NS(=O)(=O)c1ccc(NCC2CCOCC2)c([N+](=O)[O-])c1)c1ncc(N2CCN(CC3=C(c4ccc(Cl)cc4)CC4(CCC4)CC3)CC2)cc1Oc1cnc2[nH]ccc2c1] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)picolinamide |

TABLE 1-A-continued

| Cpd. No. | Structure | Name |
|---|---|---|
| 31 | 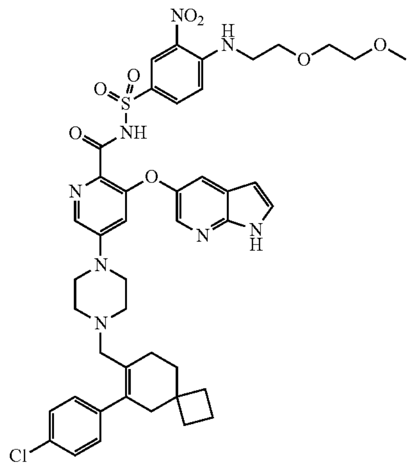 [SMILES: COCCOCCNc1ccc(S(=O)(=O)NC(=O)c2ncc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 32 | 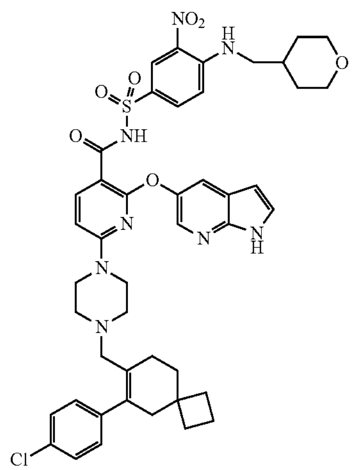 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)nc1Oc1cnc2[nH]ccc2c1] | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)nicotinamide |
| 33 | 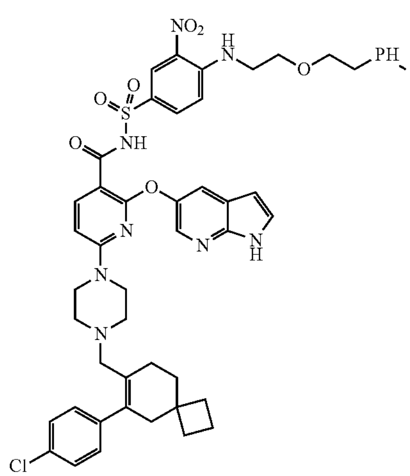 | 2-((1H-pyrrolo[2,3-b]pyridin-5-yl)oxy)-6-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)nicotinamide |

TABLE 1-A-continued

| Cpd. No. | Structure | Name |
|---|---|---|
| 34 | 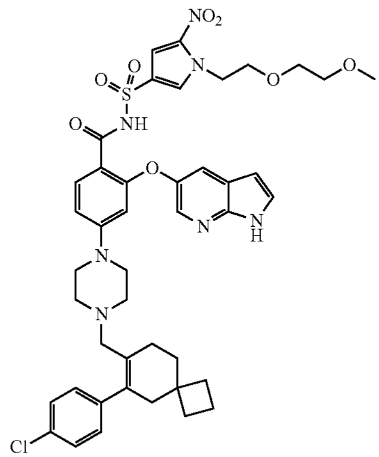 [SMILES: COCCOCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 3-((1H-pyrrolo[2,3-b]pyridin-5-yl)oxy)-5-(4-((6-(4-chlorophenyl)spiro[3.5]non-6-en-7-yl)methyl)piperazin-1-yl)-N-((4-((2-(2-methoxyethoxy)ethyl)amino)-3-nitrophenyl)sulfonyl)picolinamide |
| 35 | 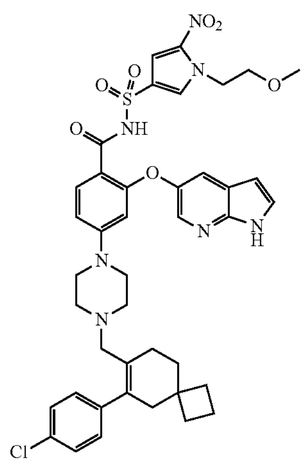 [SMILES: COCCn1cc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-(2-methoxyethyl)-5-nitro-1H-pyrrol-3-yl)sulfonyl)benzamide |
| 36 | 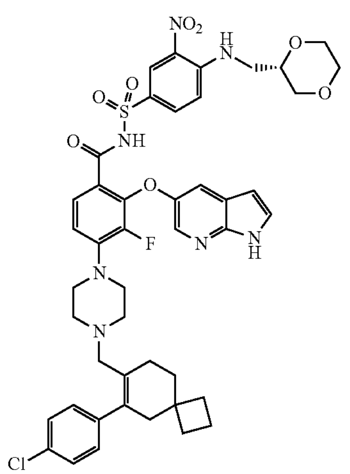 [SMILES: O=C(NS(=O)(=O)c1ccc(NC[C@H]2COCCO2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluorobenzamide |

TABLE 1-A-continued

| Cpd. No. | Structure | Name |
|---|---|---|
| 37 | 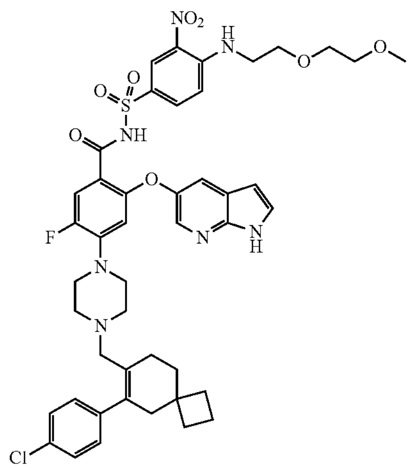 [SMILES: COCCOCCNc1ccc(S(=O)(=O)NC(=O)c2cc(F)c(N3CCN(CC4=C(c5ccc(Cl)cc5)CC5(CCC5)CC4)CC3)cc2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluoro-N-((4-((2-(2-methoxyethoxy)ethyl)amino)-3-nitrophenyl)sulfonyl)benzamide |
| 38 | 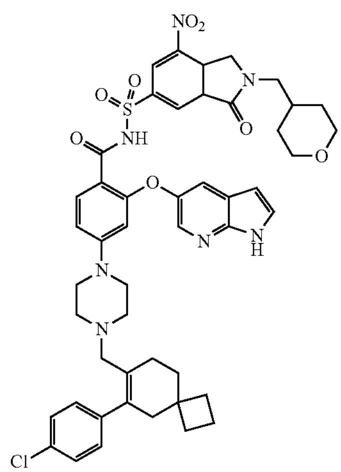 [SMILES: O=C(NS(=O)(=O)C1=CC2C(=O)N(CC3CCOCC3)CC2C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-3-oxo-2-((tetrahydro-2H-pyran-4-yl)methyl)-2,3,3a,7a-tetrahydro-1H-isoindol-5-yl)sulfonyl)benzamide |
| 39 | 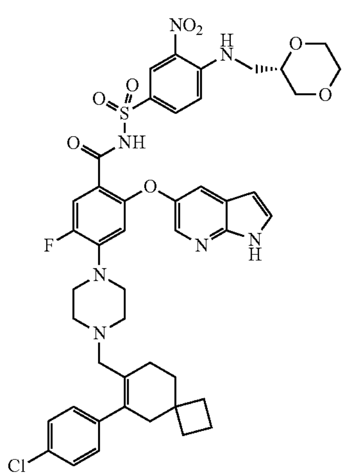 [SMILES: O=C(NS(=O)(=O)c1ccc(NC[C@H]2COCCO2)c([N+](=O)[O-])c1)c1cc(F)c(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)-5-fluorobenzamide |

TABLE 1-A-continued

| Cpd. No. | Structure | Name |
|---|---|---|
| 40 | 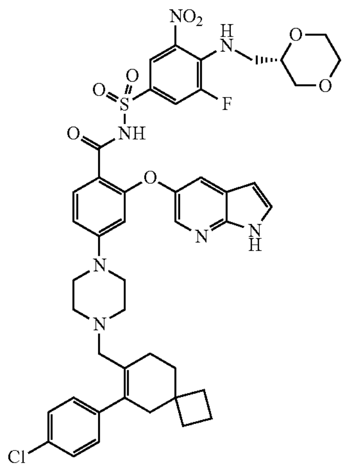 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 41 | 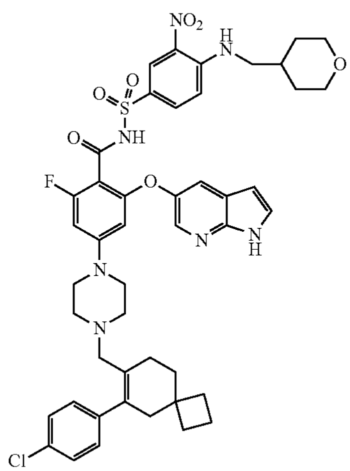 [SMILES: O=C(NS(=O)(=O)c1ccc(NCC2CCOCC2)c([N+](=O)[O-])c1)c1c(F)cc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-6-fluoro-N-((3-nitro-4-(((tetrahydro-2H-pyran-4-yl)methyl)amino)phenyl)sulfonyl)benzamide |
| 42 | 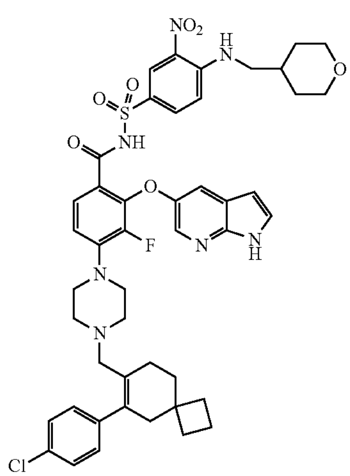 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CCC4)CC3)CC2)c(F)c1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((3-nitro-4-(((tetrahydro-2H-pyran-4-yl)methyl)amino)phenyl)sulfonyl)benzamide |

TABLE 1-A-continued

| Cpd. No. | Structure | Name |
|---|---|---|
| 43 | 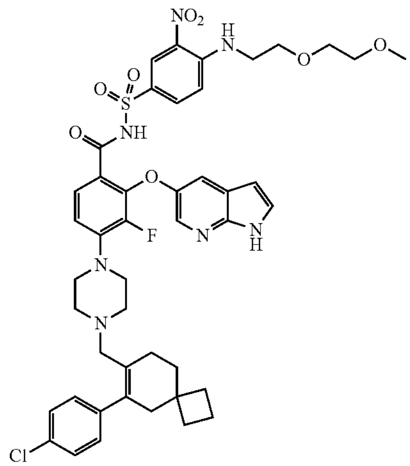 [SMILES: COCCOCCNc1ccc(S(=O)(=O)NC(=O)c2ccc(N3CCN(CC4=C(c5ccc(Cl)cc5)CC5(CCC5)CC4)CC3)c(F)c2Oc2cnc3[nH]ccc3c2)cc1[N+](=O)[O-]] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-3-fluoro-N-((4-((2-(2-methoxyethoxy)ethyl)amino)-3-nitrophenyl)sulfonyl)benzamide |
| 44 | 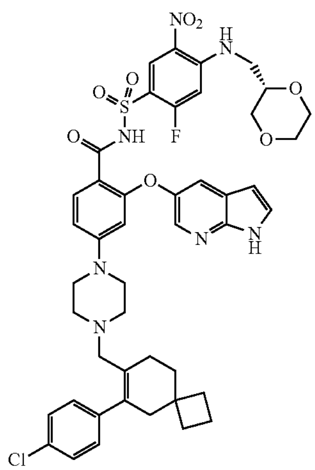 [SMILES: O=C(NS(=O)(=O)c1cc([N+](=O)[O-])c(NC[C@H]2COCCO2)cc1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |
| 45 | 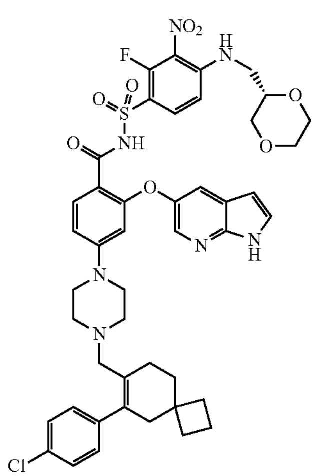 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1] | (S)-N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide |

TABLE 1-A-continued

| Cpd. No. | Structure | Name |
|---|---|---|
| 46 | 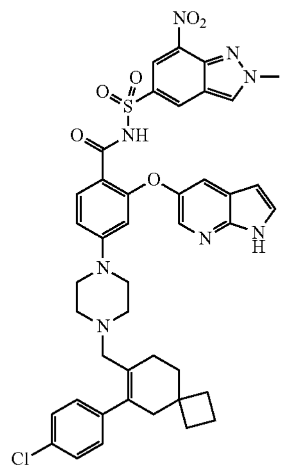 [SMILES: Cn1cc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide |
| 47 | 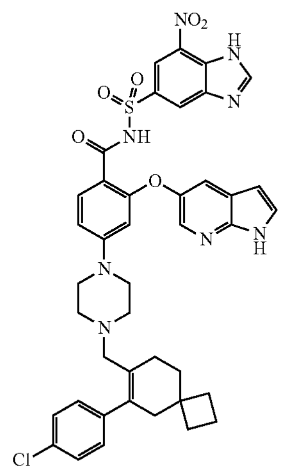 [SMILES: O=C(NS(=O)(=O)c1cc([N+](=O)[O-])c2[nH]cnc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl)sulfonyl)benzamide |
| 48 | 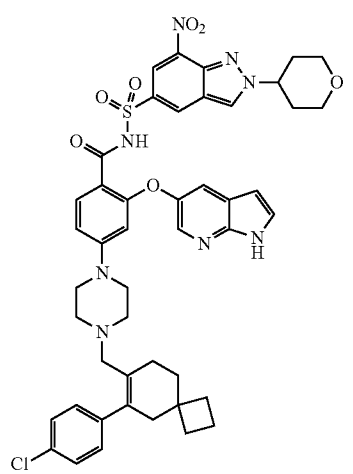 [SMILES: O=C(NS(=O)(=O)c1cc([N+](=O)[O-])c2nn(C3CCOCC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide |

TABLE 1-A-continued

| Cpd. No. | Structure | Name |
|---|---|---|
| 49 | 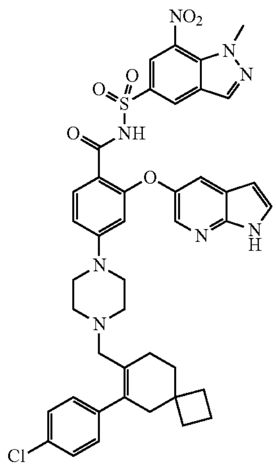 [SMILES: Cn1ncc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide |
| 50 | 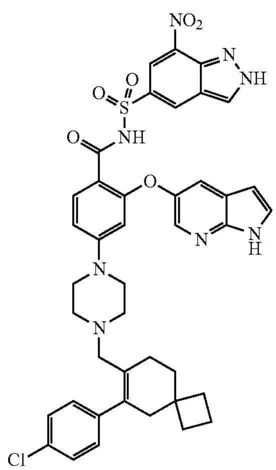 [SMILES: O=C(NS(=O)(=O)c1cc([N+](=O)[O-])c2n[nH]cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide |
| 51 | 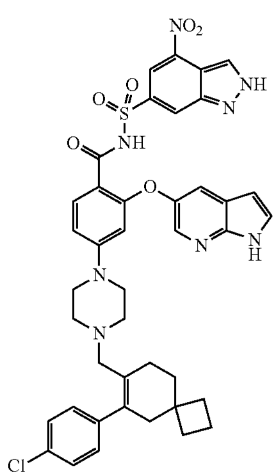 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide |

TABLE 1-A-continued

| Cpd. No. | Structure | Name |
|---|---|---|
| 52 | 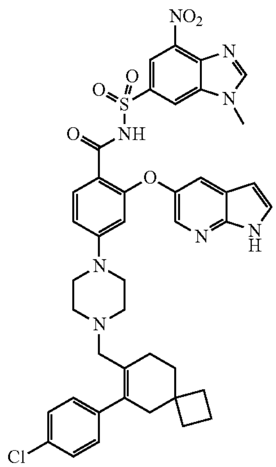 [SMILES: Cn1cnc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc21] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide |
| 53 | 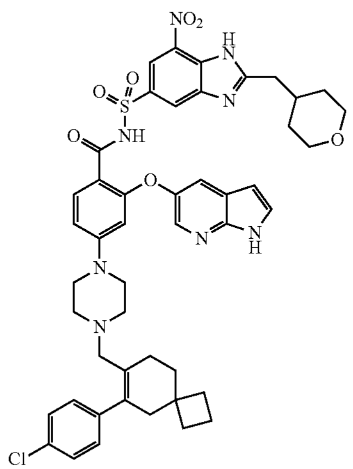 [SMILES: O=C(NS(=O)(=O)c1cc([N+](=O)[O-])c2[nH]c(CC3CCOCC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide |
| 54 | 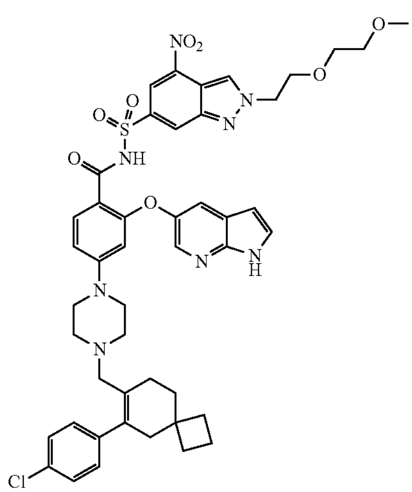 [SMILES: COCCOCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide |

TABLE 1-A-continued

| Cpd. No. | Structure | Name |
|---|---|---|
| 55 | 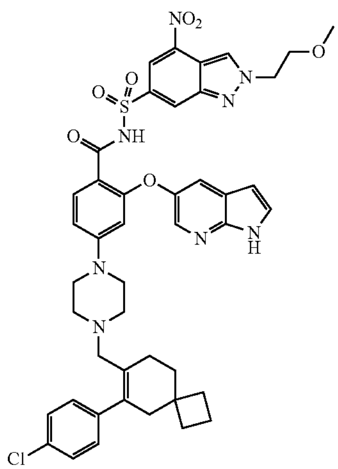 [SMILES: COCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide |
| 56 | 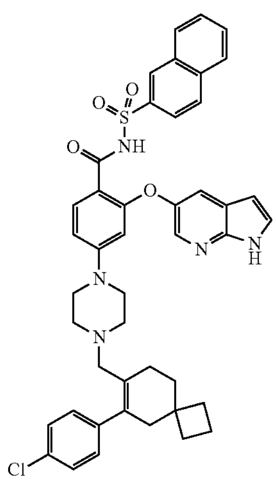 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide |

In another embodiment, a Compound of the Disclosure is the compound of Table 1-B, or a pharmaceutically acceptable salt or solvate thereof.

TABLE 1-B

| Cpd. No. | Structure | Name |
|---|---|---|
| 57 | 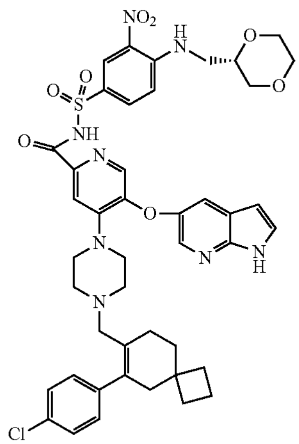 [SMILES: O=C(NS(=O)(=O)c1ccc(NC[C@H]2COCCO2)c([N+](=O)[O-])c1)c1cc(N2CCN(CC3=C(c4ccc(Cl)cc4)CC4(CCC4)CC3)CC2)c(Oc2cnc3[nH]ccc3c2)cn1] | (S)-N-((4-(((1,4-dioxan-2-yl)methyl)amino)-3-nitrophenyl)sulfonyl)-5-((1H-pyrrolo[2,3-b]pyridin-5-yl)oxy)-4-(4-((6-(4-chlorophenyl)spiro[3.5]non-6-en-7-yl)methyl)piperazin-1-yl)picolinamide |

In another embodiment, Compounds of the Disclosure are compounds selected from one or more of the compounds of Table 1-C, or a pharmaceutically acceptable salt or solvate thereof.

TABLE 1-C

| Cpd. No. | Structure | Name |
|---|---|---|
| 58 | 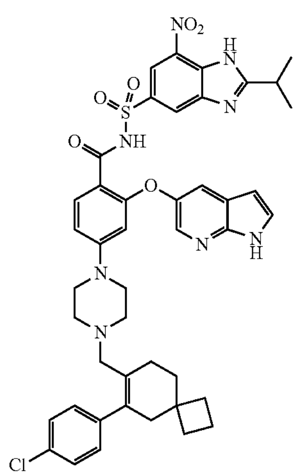 [SMILES: CC(C)c1nc2cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc([N+](=O)[O-])c2[nH]1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-isopropyl-7-nitro-1H-benzo[d]imidazol-5-yl)sulfonyl)benzamide |

TABLE 1-C-continued

| Cpd. No. | Structure | Name |
|---|---|---|
| 59 | 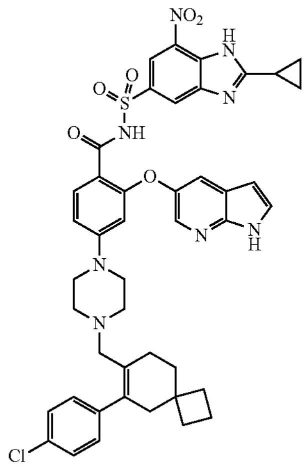 [SMILES: O=C(NS(=O)(=O)c1cc([N+](=O)[O-])c2[nH]c(C3CC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-cyclopropyl-7-nitro-1H-benzo[d]imidazol-5-yl)sulfonyl)benzamide |
| 60 | 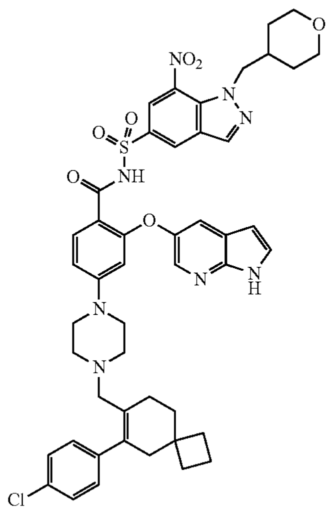 [SMILES: O=C(NS(=O)(=O)c1cc([N+](=O)[O-])c2c(cnn2CC2CCOCC2)c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1-((tetrahydro-2H-pyran-4-yl)methyl)-1H-indazol-5-yl)sulfonyl)benzamide |
| 61 | 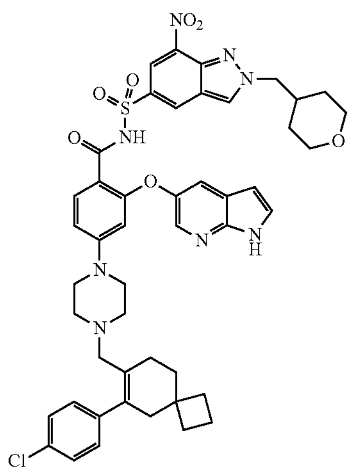 [SMILES: O=C(NS(=O)(=O)c1cc([N+](=O)[O-])c2nn(CC3CCOCC3)cc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-2H-indazol-5-yl)sulfonyl)benzamide |

TABLE 1-C-continued

| Cpd. No. | Structure | Name |
|---|---|---|
| 62 | 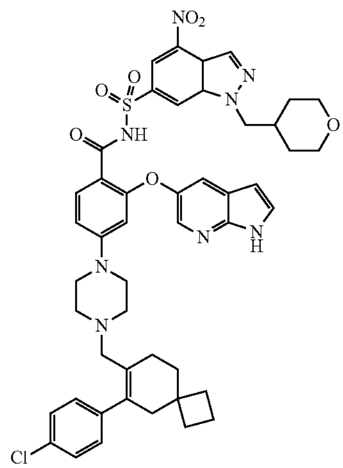 [SMILES: O=C(NS(=O)(=O)C1=CC2C(C=NN2CC2CCOCC2)C([N+](=O)[O-])=C1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-1-((tetrahydro-2H-pyran-4-yl)methyl)-3a,7a-dihydro-1H-indazol-6-yl)sulfonyl)benzamide |
| 63 | 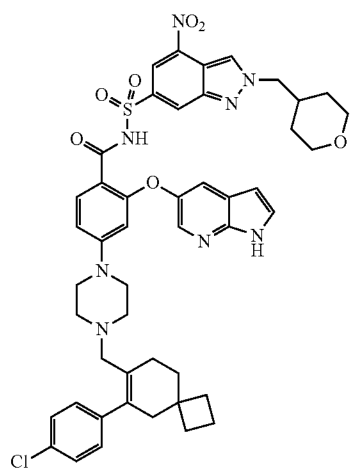 [SMILES: O=C(NS(=O)(=O)c1cc([N+](=O)[O-])c2cn(CC3CCOCC3)nc2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-((tetrahydro-2H-pyran-4-yl)methyl)-2H-indazol-6-yl)sulfonyl)benzamide |
| 64 | 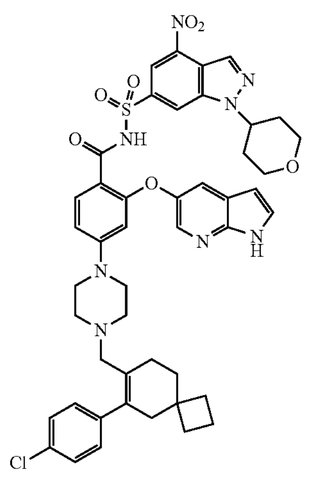 [SMILES: O=C(NS(=O)(=O)c1cc([N+](=O)[O-])c2cnn(C3CCOCC3)c2c1)c1ccc(N2CCN(CC3=C(c4ccc(Cl)cc4)CC4(CCC4)CC3)CC2)cc1Oc1cnc2[nH]ccc2c1] | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-1-(tetrahydro-2H-pyran-4-yl)-3a,7a-dihydro-1H-indazol-6-yl)sulfonyl)benzamide |

TABLE 1-C-continued
| Cpd. No. | Structure | Name |
|---|---|---|
| 65 | 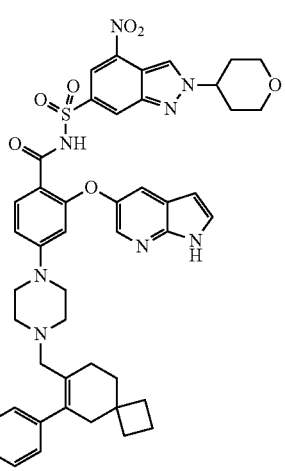 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2-(tetrahydro-2H-pyran-4-yl)-2H-indazol-6-yl)sulfonyl)benzamide |
| 66 | 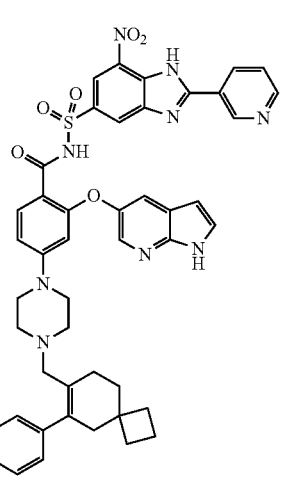 | 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(pyridin-4-yl)-1H-benzo[d]imidazol-5-yl)sulfonyl)benzamide |

In another embodiment, Compounds of the Disclosure are selected from the group consisting of:
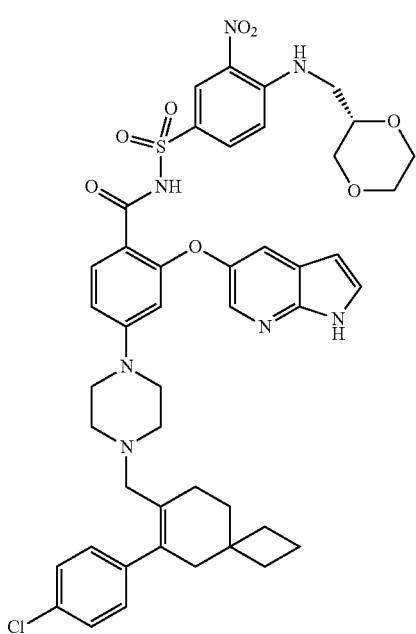
and
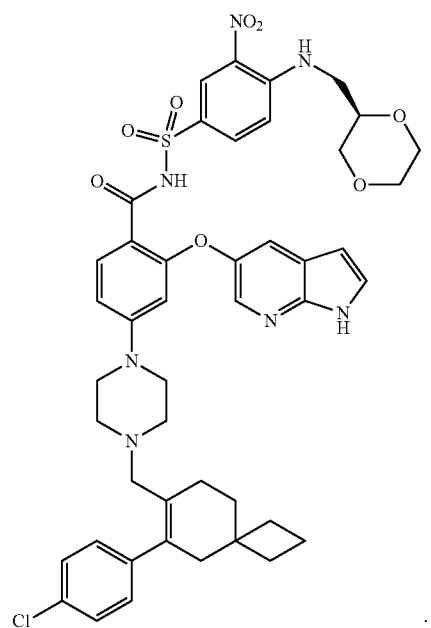 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]
or a pharmaceutically acceptable salt or solvate thereof.
In another embodiment, Compounds of the Disclosure are selected from the group consisting of:
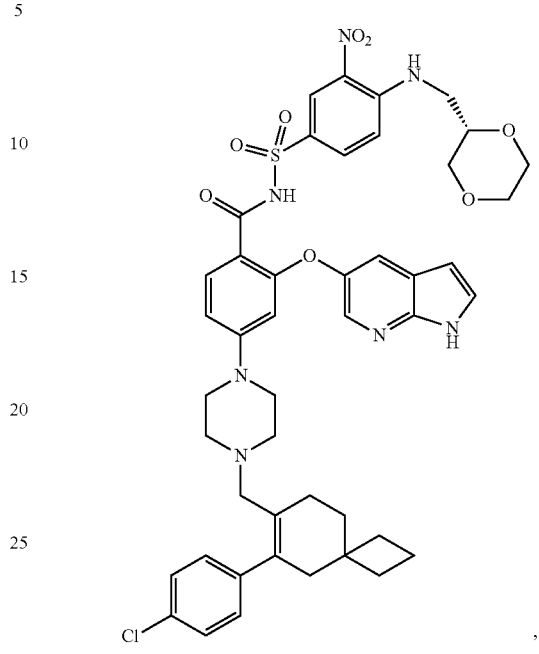
,
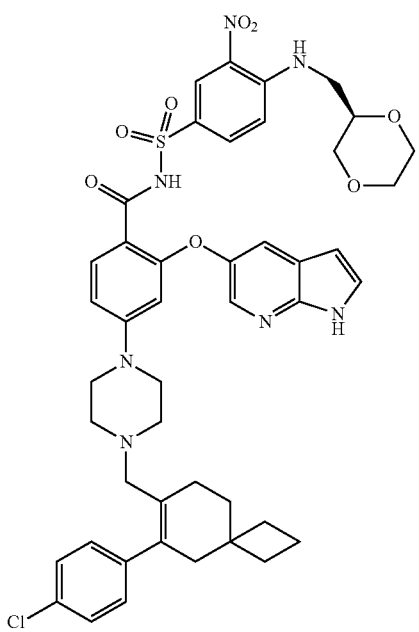
and

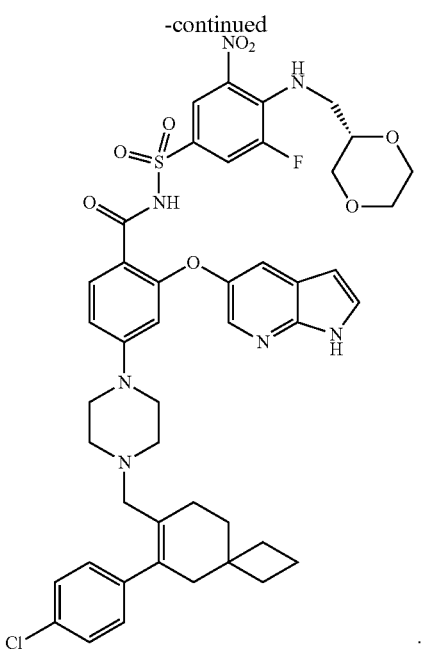

or a pharmaceutically acceptable salt or solvate thereof.

In another embodiment, a Compound of the Disclosure is:

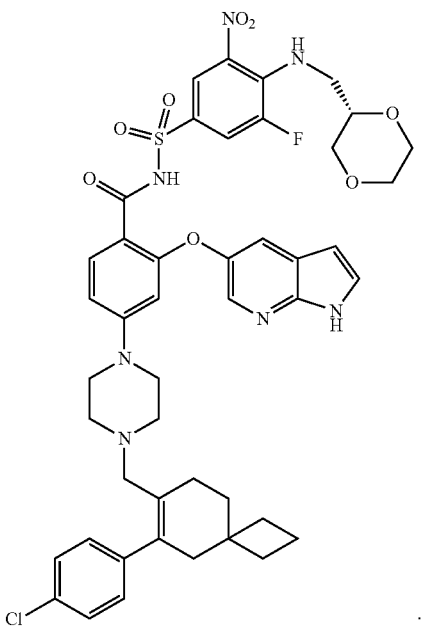 [SMILES: O=C(NS(=O)(=O)c1cc(F)c(NC[C@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

or a pharmaceutically acceptable salt or solvate thereof.

In another embodiment, the disclosure provides a pharmaceutical composition comprising a Compound of the Disclosure, or a pharmaceutically acceptable salt or solvate thereof, and a pharmaceutically acceptable carrier.

Definitions

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "amino" as used by itself or as part of another group refers to —NH$_2$.

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl group is a straight chain $C_{1-6}$ alkyl group. In another embodiment, the alkyl group is a branched chain $C_{3-6}$ alkyl group. In another embodiment, the alkyl group is a straight chain $C_{1-4}$ alkyl group. In another embodiment, the alkyl group is a branched chain $C_{3-4}$ alkyl group. In another embodiment, the alkyl group is a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-12}$ alkyl groups include methyl, —CD$_3$, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl. Non-limiting exemplary $C_{1-4}$ groups include methyl, ethyl, propyl, isopropyl, and tert-butyl.

In the present disclosure, the term "optionally substituted alkyl" as used by itself or as part of another group refers to an alkyl that is unsubstituted or substituted with one, two, or three substituents independently selected from the group consisting of halo, nitro, cyano, hydroxy, alkoxy, amino, alkylamino, dialkylamino, and optionally substituted aryl. In one embodiment, the optionally substituted alkyl is substituted with two substituents. In another embodiment, the optionally substituted alkyl is substituted with one substituent. In another embodiment, the optionally substituted alkyl is unsubstituted. Non-limiting exemplary optionally substituted alkyl groups include —CH$_2$Ph, —CH$_2$CH$_2$NO$_2$, —CH$_2$CH$_2$OH, —CH$_2$CH$_2$OCH$_3$, and —CH$_2$CH$_2$F.

In the present disclosure, the term "cycloalkyl" as used by itself or as part of another group refers to unsubstituted saturated or partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl group is a $C_{3-8}$ cycloalkyl. In another embodiment, the cycloalkyl group is a $C_{3-6}$ cycloalkyl. In another embodiment, the cycloalkyl group is a $C_{3-5}$ cycloalkyl. The term "cycloalkyl" is meant to include groups wherein a ring —CH$_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclopentanone, spiro[3.3]heptane, and bicyclo[3.3.1]nonane.

In the present disclosure, the term "optionally substituted cycloalkyl" as used by itself or as part of another group refers to a cycloalkyl that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo. In one embodiment, the optionally substituted cycloalkyl is substituted with two substituents. In another embodiment, the optionally substituted cycloalkyl is substituted with one substituent. In another embodiment, the optionally substituted cycloalkyl is unsubstituted.

In the present disclosure, the term "haloalkyl" as used by itself or as part of another group refers to an alkyl substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl attached to a terminal oxygen atom. In one embodiment, the alkoxy group is a $C_{1-6}$ alkyl attached to a terminal oxygen atom. In another embodiment, the alkoxy group is a $C_{1-4}$ alkyl attached to a terminal oxygen atom. Non-limiting exemplary alkoxy groups include methoxy, ethoxy, and ter t-butoxy.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, alkyl, alkoxy, amino, alkylamino, dialkylamino, haloalkyl, and heterocyclo. In one embodiment, the optionally substituted aryl is an optionally substituted phenyl. In another embodiment, the optionally substituted phenyl has one substituent. In another embodiment, the optionally substituted phenyl is unsubstituted. Non-limiting exemplary substituted aryl groups include 2-methylphenyl, 2-methoxyphenyl, 2-fluorophenyl, and 4-chlorophenyl.

In the present disclosure, the term "heterocyclo" as used by itself or as part of another group refers to unsubstituted saturated and partially unsaturated, e.g., containing one or two double bonds, cyclic groups containing one, two, or three rings having from three to fourteen ring members, i.e., a 3- to 14-membered heterocyclo, wherein at least one carbon atom of one of the rings is replaced with a heteroatom. The term "heterocyclo" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. In one embodiment, the heterocyclo group is a 4-, 5-, 6-, 7- or 8-membered cyclic group containing one ring and one or two oxygen and/or nitrogen atoms. In one embodiment, the heterocyclo group is a 5- or 6-membered cyclic group containing one ring and one or two nitrogen atoms. In one embodiment, the heterocyclo group is an 8-, 9-, 10-, 11-, or 12-membered cyclic group containing two rings and one or two nitrogen atoms. In one embodiment, the heterocyclo group is a 4- or 5-membered cyclic group containing one ring and one oxygen atom. The heterocyclo can be optionally linked to the rest of the molecule through a carbon or nitrogen atom. Non-limiting exemplary heterocyclo groups include 1,4-dioxane, 2-oxopyrrolidin-3-yl, 2-imidazolidinone, piperidinyl, morpholinyl, piperazinyl, pyrrolidinyl, 8-azabicyclo[3.2.1]octane (nortropane), 6-azaspiro[2.5]octane, 6-azaspiro[3.4]octane, indolinyl, indolinyl-2-one, and 1,3-dihydro-2H-benzo[d]imidazol-2-one.

In the present disclosure, the term "optionally substituted heterocyclo" as used herein by itself or part of another group refers to a heterocyclo that is either unsubstituted or substituted with one, two, or three substituents independently selected from the group consisting of halo, nitro, cyano, hydroxy, alkyl, alkoxy, amino, alkylamino, dialkylamino, haloalkyl, and heterocyclo. Non-limiting exemplary optionally substituted heterocyclo groups include:

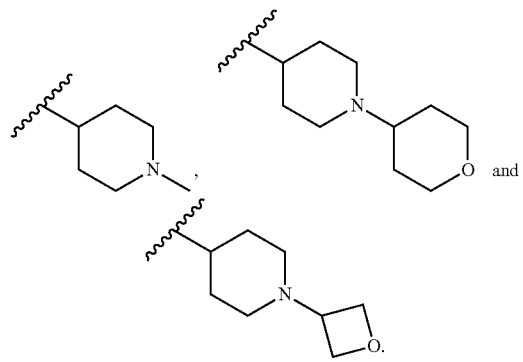

In the present disclosure, the term "alkylamino" as used by itself or as part of another group refers to $-NHR^{10}$, wherein $R^{10}$ is $C_{1-6}$ alkyl. In one embodiment, $R^{10}$ is $C_{1-4}$ alkyl. Non-limiting exemplary alkylamino groups include $-N(H)CH_3$ and $-N(H)CH_2CH_3$.

In the present disclosure, the term "dialkylamino" as used by itself or as part of another group refers to $-NR^{11a}R^{11b}$, wherein $R^{11a}$ and $R^{11b}$ are each independently $C_{1-6}$ alkyl. In one embodiment, $R^{11a}$ and $R^{11b}$ are each independently $C_{1-4}$ alkyl. Non-limiting exemplary dialkylamino groups include $-N(CH_3)_2$ and $-N(CH_3)CH_2CH(CH_3)_2$.

In the present disclosure, the term "(cycloalkyl)alkyl" as used by itself or as part of another group refers to an alkyl substituted with one optionally substituted cycloalkyl group. In one embodiment, the (cycloalkyl)alkyl is a $C_{1-4}$ alkyl substituted with one optionally substituted $C_{3-6}$ cycloalkyl. In one embodiment, the optionally substituted cycloalkyl group is substituted with a heterocyclo group. Non-limiting exemplary (cycloalkyl)alkyl groups include:

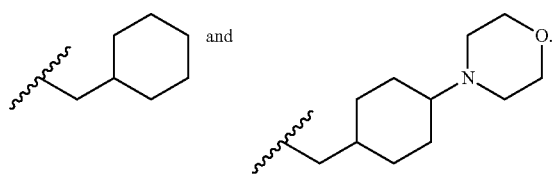 [SMILES: *CC1CCCCC1 ; *CC1CCC(N2CCOCC2)CC1]

In the present disclosure, the term "(heterocyclo)alkyl" as used by itself or as part of another group refers to an alkyl substituted with one optionally substituted heterocyclo group. In one embodiment, the (heterocyclo)alkyl is a $C_{1-4}$ alkyl substituted with one optionally substituted 4- to 6-membered heterocyclo group. The heterocyclo can be linked to the alkyl group through a carbon or nitrogen atom. Non-limiting exemplary (heterocyclo)alkyl groups include:

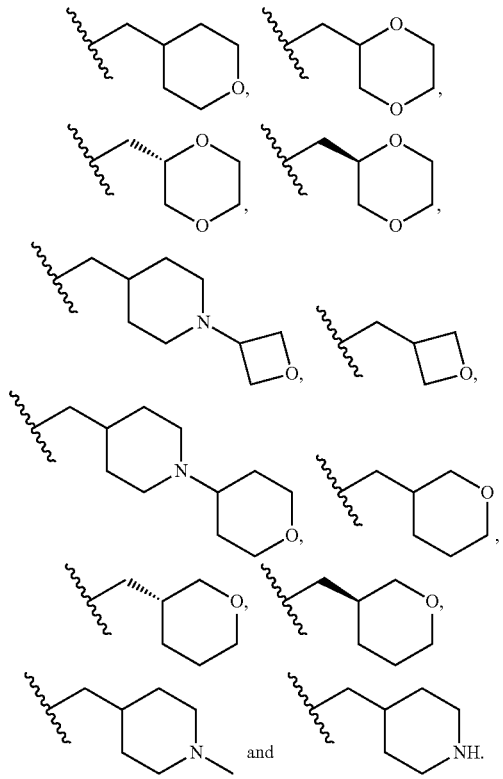

In the present disclosure, the term "heteroalkyl" as used by itself or part of another group refers to unsubstituted straight- or branched-chain aliphatic hydrocarbons containing from six to twelve chain atoms, i.e., 6- to 12-membered heteroalkyl, or the number of chain atoms designated, wherein at least two —CH$_2$— groups are independently replaced with —O—, —N(H)—, or —S—. The —O—, —N(H)—, or —S— can independently be placed at any interior position of the aliphatic hydrocarbon chain so long as each —O—, N(H)—, or —S— group is separated by at least two —CH$_2$— groups. In one embodiment, two —CH$_2$— groups are replaced with two —O— groups. In another embodiment, three —CH$_2$— groups are replaced with three —O— groups. Non-limiting exemplary heteroalkyl groups include —CH$_2$CH$_2$OCH$_2$CH$_2$OCH$_3$, —CH$_2$CH$_2$OCH$_2$CH$_2$N(H)CH$_3$, and —CH$_2$CH$_2$OCH$_2$CH$_2$OCH$_2$CH$_2$OCH$_3$.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, and $^{14}$C. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number. Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms including racemic and resolved forms, and mixtures thereof. The individual stereoisomers, e.g., enantiomers, can be separated according to methods known in the art in view of the present disclosure. When the compounds described herein contain olefinic double bonds or other centers of geometric asymmetry, and unless specified otherwise, it is intended that they include both E and Z geometric isomers. All tautomers are also intended to be encompassed by the present disclosure.

As used herein, the term "stereoisomers" or "stereoisomeric forms" are general terms for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in Pure & Appl. Chem 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as ($[α]_{obs}/[α]_{max}$)*100, where $[α]_{obs}$ is the optical rotation of the mixture of enantiomers and $[α]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense. In one embodiment, Compounds of the Disclosure having one or more chiral centers are enantiopure.

The terms "enantiomerically enriched" or "enantioenriched" refer to a sample of a chiral substance whose enantiomeric excess is greater than 50%, e.g., about 60% or more, about 70% or more, about 80% or more, about 90% or more, about 95% or more, about 98% or more, or about 99% or more. Enantiomerically enriched compounds may be enantiomerically pure. In one embodiment, Compounds of the Disclosure having one or more chiral centers are enantioenriched.

The terms "a" and "an" refer to one or more.

The term "about," as used herein, includes the recited number ±10%. Thus, "about 10" means 9 to 11.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. The term "pharmaceutically acceptable salt" as used herein, refers to any salt, e.g., obtained by reaction with an acid or a base, of a Compound of the Disclosure that is physiologically tolerated in the target patient (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g., a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure.

In one embodiment, the solvate is a hydrate. A "hydrate" relates to a particular subgroup of solvates where the solvent molecule is water. Solvates typically can function as pharmacological equivalents. Preparation of solvates is known in the art. See, for example, M. Caira et al, J. Pharmaceut. Sci., 93(3):601-611 (2004), which describes the preparation of solvates of fluconazole with ethyl acetate and with water. Similar preparation of solvates, hemisolvates, hydrates, and the like are described by E. C. van Tonder et al., AAPS Pharm. Sci. Tech., 5(1):Article 12 (2004), and A. L. Bingham et al., Chem. Commun. 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Compounds of the Disclosure are inhibitors of Bcl-2 proteins, such as Bcl-2, and/or Bcl-$X_L$, and thus a number of diseases, conditions, or disorders mediated by Bcl-2 proteins can be treated or prevented by administering these compounds to a subject. The present disclosure is thus directed generally to a method for treating or preventing a disease, condition, or disorder responsive to the inhibition of Bcl-2 proteins, such as Bcl-2, and/or Bcl-$X_L$, in an animal suffering from, or at risk of suffering from, the disease, condition, or disorder The method comprises administering to the animal an effective amount of one or more Compounds of the Disclosure.

The present disclosure is further directed to a method of inhibiting Bcl-2 proteins in an animal, e.g., a human, in need thereof, the method comprising administering to the animal a therapeutically effective amount of at least one Compound of the Disclosure.

The present disclosure is further directed to a method of inhibiting Bcl-2 in an animal, e.g., a human, in need thereof, the method comprising administering to the animal a therapeutically effective amount of at least one Compound of the Disclosure.

The present disclosure is further directed to a method of inhibiting Bcl-$X_L$ in an animal, e.g., a human, in need thereof, the method comprising administering to the animal a therapeutically effective amount of at least one Compound of the Disclosure.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

In the present disclosure, the term "Bcl-2 proteins" or "Bcl-2 family of proteins" refers to any one or more of the following proteins: Bax, Bak, Bid, Bcl-2, Bcl-xL, Mcl-1, Bcl-w, Bfl-1/A1, Bim, Puma, Bad, Bik/Blk, Noxa, Bmf, Hrk/DP5, and Beclin-1. See Cold Spring Harb Perspect Biol 2013;5:a008714.

The term "disease" or "condition" or "disorder" denotes disturbances and/or anomalies that as a rule are regarded as being pathological conditions or functions, and that can manifest themselves in the form of particular signs, symptoms, and/or malfunctions. Compounds of the Disclosure inhibit Bcl-2 proteins, such as Bcl-2 and/or Bcl-xL, and can be used in treating or preventing diseases, conditions, or disorders such as hyperproliferative diseases, wherein inhibition of Bcl-2 proteins provides a benefit.

The term "hyperproliferative disease" refers to any condition in which a localized population of proliferating cells in an animal is not governed by the usual limitations of normal growth. In one embodiment, the hyperproliferative disease is cancer.

In some embodiments, the Compounds of the Disclosure can be used to treat a "Bcl-2 protein mediated disorder," e.g., a Bcl-2-mediated disorder and/or a Bcl-xL-mediated disorder. A Bcl-2 protein mediated disorder is any pathological condition in which a Bcl-2 protein is known to play a role. In one embodiment, a Bcl-2 mediated disorder is a hyperproliferative disease. In one embodiment, a Bcl-2 mediated disorder is cancer.

In one embodiment, Compounds of the Disclosure have a Bcl-2 and/or Bcl-xL $IC_{50}$ of less than about 10 μM. In another embodiment, Compounds of the Disclosure have a Bcl-2 and/or Bcl-xL $IC_{50}$ of less than about 5 μM. In another embodiment, Compounds of the Disclosure have a Bcl-2 and/or Bcl-xL $IC_{50}$ of less than about 1 μM. In another embodiment, Compounds of the Disclosure have a Bcl-2 and/or Bcl-xL $IC_{50}$ of less than about 0.5 μM. In another embodiment, Compounds of the Disclosure have a Bcl-2 and/or Bcl-xL $IC_{50}$ of less than about 0.1 μM. In another embodiment, Compounds of the Disclosure have a Bcl-2 and/or Bcl-xL $IC_{50}$ of less than about 0.05 μM. In another embodiment, Compounds of the Disclosure have a Bcl-2 and/or Bcl-xL $IC_{50}$ of less than about 0.025 μM. In another embodiment, Compounds of the Disclosure have a Bcl-2 and/or Bcl-xL $IC_{50}$ of less than about 0.010 μM. In another embodiment, Compounds of the Disclosure have a Bcl-2 and/or Bcl-xL $IC_{50}$ of less than about 0.005 μM. In another embodiment, Compounds of the Disclosure have a Bcl-2 and/or Bcl-xL $IC_{50}$ of less than about 0.0025 μM. In another embodiment, Compounds of the Disclosure have a Bcl-2 and/or Bcl-xL $IC_{50}$ of less than about 0.001 μM.

In one embodiment, the present disclosure provides a method of treating or preventing a hyperproliferative disease in a subject, e.g., a human, comprising administering a therapeutically effective amount of a Compound of the Disclosure.

In another embodiment, the present disclosure provides a method of treating or preventing cancer in a subject comprising administering a therapeutically effective amount of a Compound of the Disclosure. While not being limited to a specific mechanism, in some embodiments, Compounds of the Disclosure can treat or prevent cancer by inhibiting Bcl-2 proteins, e.g., Bcl-2 and/or Bcl-xL. Examples of treatable cancers include, but are not limited to, any one or more of the cancers of Table 2.

TABLE 2 adrenal cancer
acinic cell carcinoma
acoustic neuroma
acral lentigious melanoma
acrospiroma
acute eosinophilic leukemia
acute erythroid leukemia
acute lymphoblastic leukemia
acute megakaryoblastic leukemia
acute monocytic leukemia
acute promyelocytic leukemia
adenocarcinoma
adenoid cystic carcinoma
adenoma
adenomatoid odontogenic tumor
adenosquamous carcinoma
adipose tissue neoplasm
adrenocortical carcinoma
adult T-cell leukemia/lymphoma
aggressive NK-cell leukemia
AIDS-related lymphoma
alveolar rhabdomyosarcoma
alveolar soft part sarcoma
ameloblastic fibroma
anaplastic large cell lymphoma
anaplastic thyroid cancer
angioimmunoblastic T-cell lymphoma,
angiomyolipoma
angiosarcoma
astrocytoma
atypical teratoid rhabdoid tumor
B-cell chronic lymphocytic leukemia
B-cell prolymphocytic leukemia
B-cell lymphoma
basal cell carcinoma
biliary tract cancer
bladder cancer
blastoma
bone cancer
Brenner tumor
Brown tumor
Burkitt's lymphoma
breast cancer
brain cancer
carcinoma
carcinoma in situ TABLE 2-continued carcinosarcoma
cartilage tumor
cementoma
myeloid sarcoma
chondroma
chordoma
choriocarcinoma
choroid plexus papilloma
clear-cell sarcoma of the kidney
craniopharyngioma
cutaneous T-cell lymphoma
cervical cancer
colorectal cancer
Degos disease
desmoplastic small round cell tumor
diffuse large B-cell lymphoma
dysembryoplastic neuroepithelial tumor,
dysgerminoma
embryonal carcinoma
endocrine gland neoplasm
endodermal sinus tumor
enteropathy-associated T-cell lymphoma
esophageal cancer
fetus in fetu
fibroma
fibrosarcoma
follicular lymphoma
follicular thyroid cancer
ganglioneuroma
gastrointestinal cancer
germ cell tumor
gestational choriocarcinoma
giant cell fibroblastoma
giant cell tumor of the bone
glial tumor
glioblastoma multiforme
glioma
gliomatosis cerebri
glucagonoma
gonadoblastoma
granulosa cell tumor
gynandroblastoma
gallbladder cancer
gastric cancer
hairy cell leukemia
hemangioblastoma
head and neck cancer
hemangiopericytoma
hematological malignancy
hepatoblastoma
hepatosplenic T-cell lymphoma
Hodgkin's lymphoma
non-Hodgkin's lymphoma
invasive lobular carcinoma
intestinal cancer
kidney cancer
laryngeal cancer
lentigo maligna
lethal midline carcinoma
leukemia
leydig cell tumor
liposarcoma
lung cancer
lymphangioma
lymphangiosarcoma
lymphoepithelioma
lymphoma
acute lymphocytic leukemia
acute myelogeous leukemia
chronic lymphocytic leukemia
liver cancer
small cell lung cancer
non-small cell lung cancer
MALT lymphoma
malignant fibrous histiocytoma
malignant peripheral nerve sheath tumor
malignant triton tumor
mantle cell lymphoma
marginal zone B-cell lymphoma
mast cell leukemia TABLE 2-continued mediastinal germ cell tumor
medullary carcinoma of the breast
medullary thyroid cancer,
medulloblastoma
melanoma,
meningioma,
merkel cell cancer
mesothelioma
metastatic urothelial carcinoma
mixed Mullerian tumor
mucinous tumor
multiple myeloma
muscle tissue neoplasm
mycosis fungoides
myxoid liposarcoma
myxoma
myxosarcoma
nasopharyngeal carcinoma
neurinoma
neuroblastoma
neurofibroma
neuroma
nodular melanoma
ocular cancer
oligoastrocytoma
oligodendroglioma
oncocytoma
optic nerve sheath meningioma
optic nerve tumor
oral cancer
osteosarcoma
ovarian cancer
Pancoast tumor
papillary thyroid cancer
paraganglioma
pinealoblastoma
pineocytoma
pituicytoma
pituitary adenoma
pituitary tumor
plasmacytoma
polyembryoma
precursor T-lymphoblastic lymphoma
primary central nervous system lymphoma
primary effusion lymphoma
preimary peritoneal cancer
prostate cancer
pancreatic cancer
pharyngeal cancer
pseudomyxoma periotonei
renal cell carcinoma
renal medullary carcinoma
retinoblastoma
rhabdomyoma
rhabdomyosarcoma
Richter's transformation
rectal cancer
sarcoma
Schwannomatosis
seminoma
Sertoli cell tumor
sex cord-gonadal stromal tumor
signet ring cell carcinoma
skin cancer
small blue round cell tumors
small cell carcinoma
soft tissue sarcoma
somatostatinoma
soot wart
spinal tumor
splenic marginal zone lymphoma
squamous cell carcinoma
synovial sarcoma
Sezary's disease
small intestine cancer
squamous carcinoma
stomach cancer
T-cell lymphoma
testicular cancer
thecoma TABLE 2-continued thyroid cancer
transitional cell carcinoma
throat cancer
urachal cancer
urogenital cancer
urothelial carcinoma
uveal melanoma
uterine cancer
verrucous carcinoma
visual pathway glioma
vulvar cancer
vaginal cancer
Waldenstrom's macroglobulinemia
Warthin's tumor
Wilms' tumor In another embodiment, the cancer is breast, cervix, colon, kidney, liver, head and neck, skin, pancreas, ovary, esophagus, or prostate cancer.

In another embodiment, the cancer is a hematologic malignancy such as acute myeloid leukemia (AML), B- and T-acute lymphoblastic leukemia (ALL), chronic lymphocytic leukemia (CLL), or mantle cell lymphoma (MCL).

In another embodiment, the cancer is esophageal squamous cell carcinoma (ESCC), bladder carcinoma, or cervical carcinoma.

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is adrenocortical carcinoma, bladder urothelial carcinoma, breast invasive carcinoma, colorectal adenocarcinoma, diffuse large B-cell lymphoma, head and neck squamous cell carcinoma, hepatocellular carcinoma, lung adenocarcinoma, lung squamous cell carcinoma, ovarian serous cystadenocarcinoma, pancreatic adenocarcinoma, prostate adenocarcinoma, renal clear cell carcinoma, skin cutaneous melanoma, stomach adenocarcinoma, uterine carcinosarcoma, or uterine corpus endometrial carcinoma.

In another embodiment, the present disclosure provides a therapeutic method of modulating gene expression, cell proliferation, cell differentiation and/or apoptosis in vivo in a cancer, e.g., in the cancers mentioned above, by administering a therapeutically effective amount of a Compound of the Disclosure to a subject in need of such therapy.

Compounds of the Disclosure can be administered to a subject in the form of a raw chemical without any other components present. Compounds of the Disclosure can also be administered to a subject as part of a pharmaceutical composition containing the compound combined with one or more suitable pharmaceutically acceptable carriers. Such carriers can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A Compound of the Disclosure or a pharmaceutical composition comprising a Compound of the Disclosure can be administered to any patient or subject that may experience the beneficial effects of a Compound of the Disclosure. Foremost among such patients or subject are mammals, e.g., humans and companion animals, although the disclosure is not intended to be so limited. In one embodiment, the patient or subject is a human.

A Compound of the Disclosure or a pharmaceutical composition comprising a Compound of the Disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a Compound of the Disclosure or a pharmaceutical composition comprising a Compound of the Disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a Compound of the Disclosure or a pharmaceutical composition comprising a Compound of the Disclosure can be administered rectally, and is formulated in suppositories.

Alternatively, a Compound of the Disclosure or a pharmaceutical composition comprising a Compound of the Disclosure can be administered by injection.

Alternatively, a Compound of the Disclosure or a pharmaceutical composition comprising a Compound of the Disclosure can be administered transdermally.

Alternatively, a Compound of the Disclosure or a pharmaceutical composition comprising a Compound of the Disclosure can be administered by inhalation or by intranasal or transmucosal administration.

Alternatively, a Compound of the Disclosure or a pharmaceutical composition comprising a Compound of the Disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a Compound of the Disclosure (or a pharmaceutical composition comprising a Compound of the Disclosure) packaged in a manner that facilitates their use to practice methods of the present disclosure. In one embodiment, the kit includes a Compound of the Disclosure (or a pharmaceutical composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

In another embodiment, a Compound of the Disclosure is administered to a subject in conjunction with a second therapeutic agent. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DM1, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as P1-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SUlOl, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, $C_{1-1033}$, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortexolone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

General Synthesis of Compounds

Compounds of the Disclosure are prepared using methods known to those skilled in the art in view of this disclosure, or by the illustrative methods shown in the General Schemes below. In the General Schemes, $R^2$ and $R^{4a}$ are as defined in connection with Formula I, and Y is as defined in connection with Formula II.

General Scheme 1

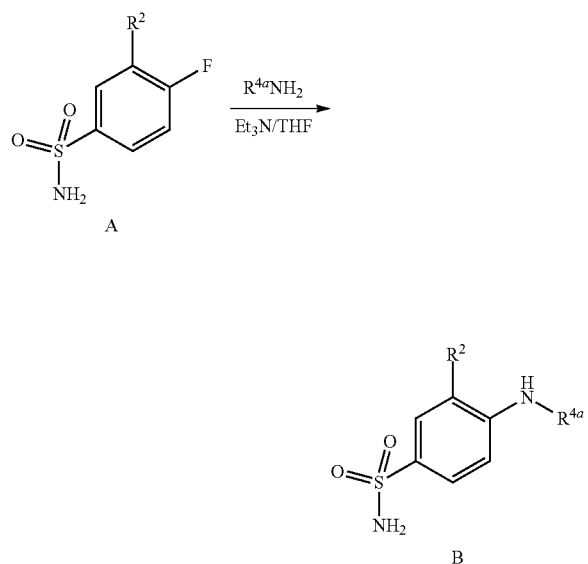

In General Scheme 1, Compound A is reacted with $R^{4a}NH_2$ in the presence of a base, e.g., triethylamine, to give Compound B.

General Scheme 2

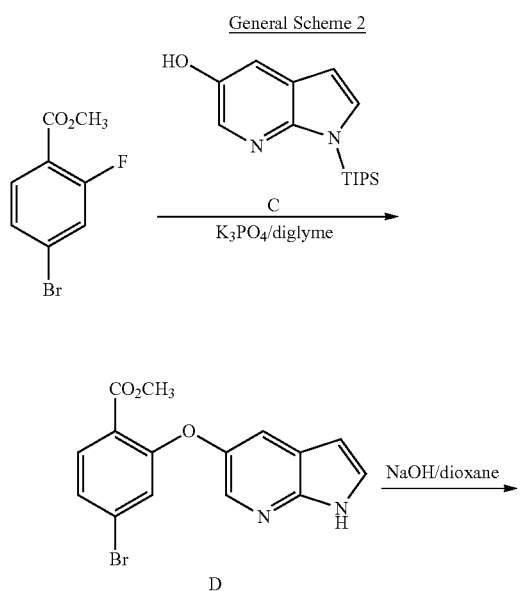

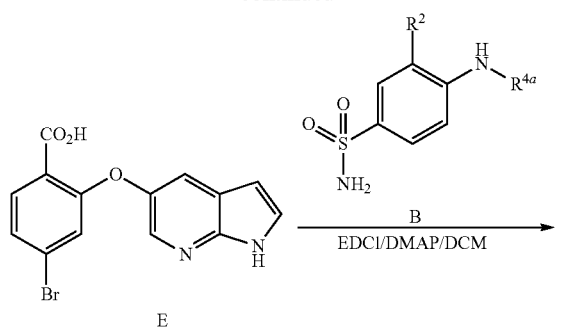

In General Scheme 2, methyl 4-bromo-2-fluorobenzoate is reacted with Compound C to give Compound D, and the ester of Compound D is hydrolyzed to give Compound E. Compound E is coupled with Compound B from General Scheme 1 to give Compound F.

General Scheme 3

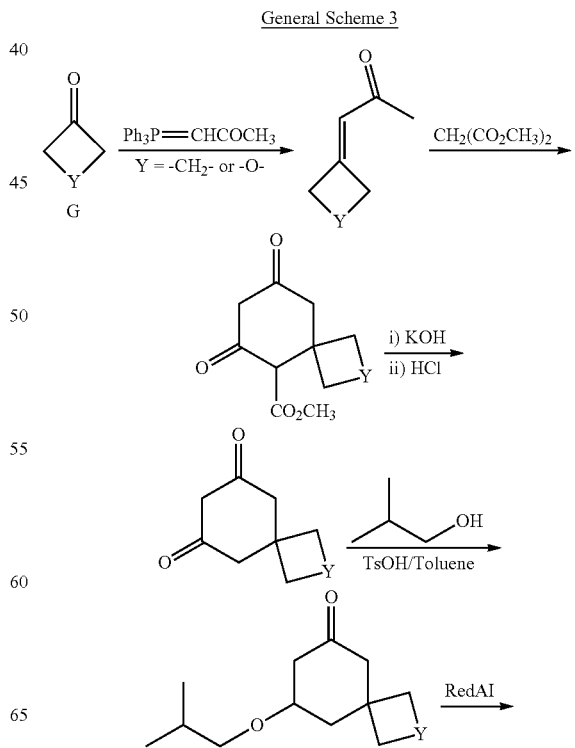

87
-continued
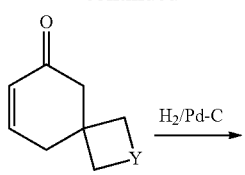
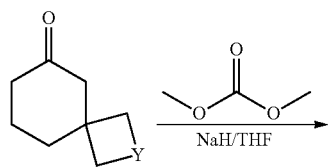
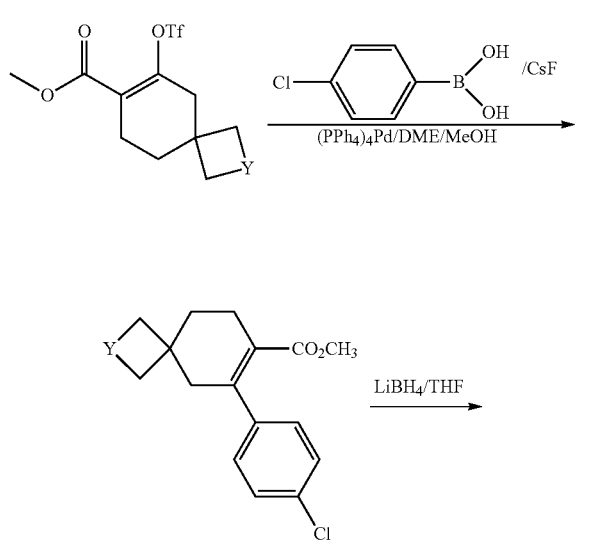
88
-continued
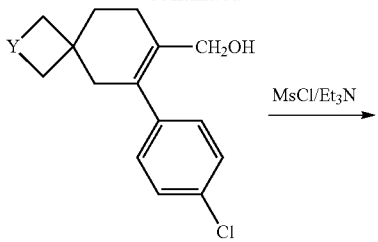
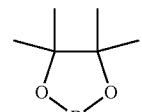
In General Scheme 3, Compound G is transformed Compound H.
General Scheme 4
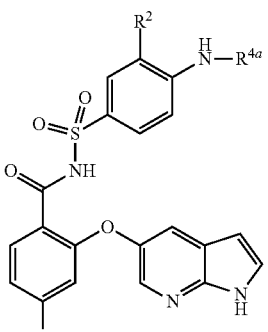

89
-continued
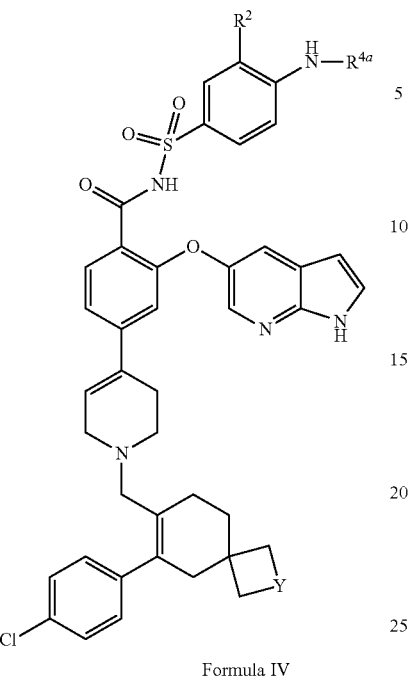
Formula IV
In General Scheme 4, Compound H from General Scheme 3 is reacted with 4-(4,4,5,5-tetramethyl-1,3,2-dioxaborolan-2-yl)-1,2,3,6-tetrahydropyridine to give Compound I. Compound I is coupled with Compound F from General Scheme 2 to give a compound having Formula IV.
General Scheme 5
90
-continued
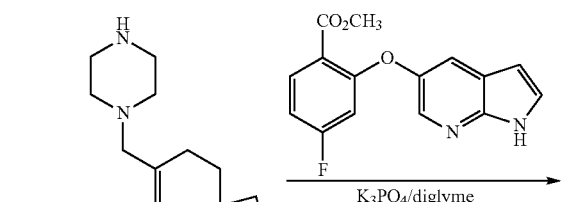
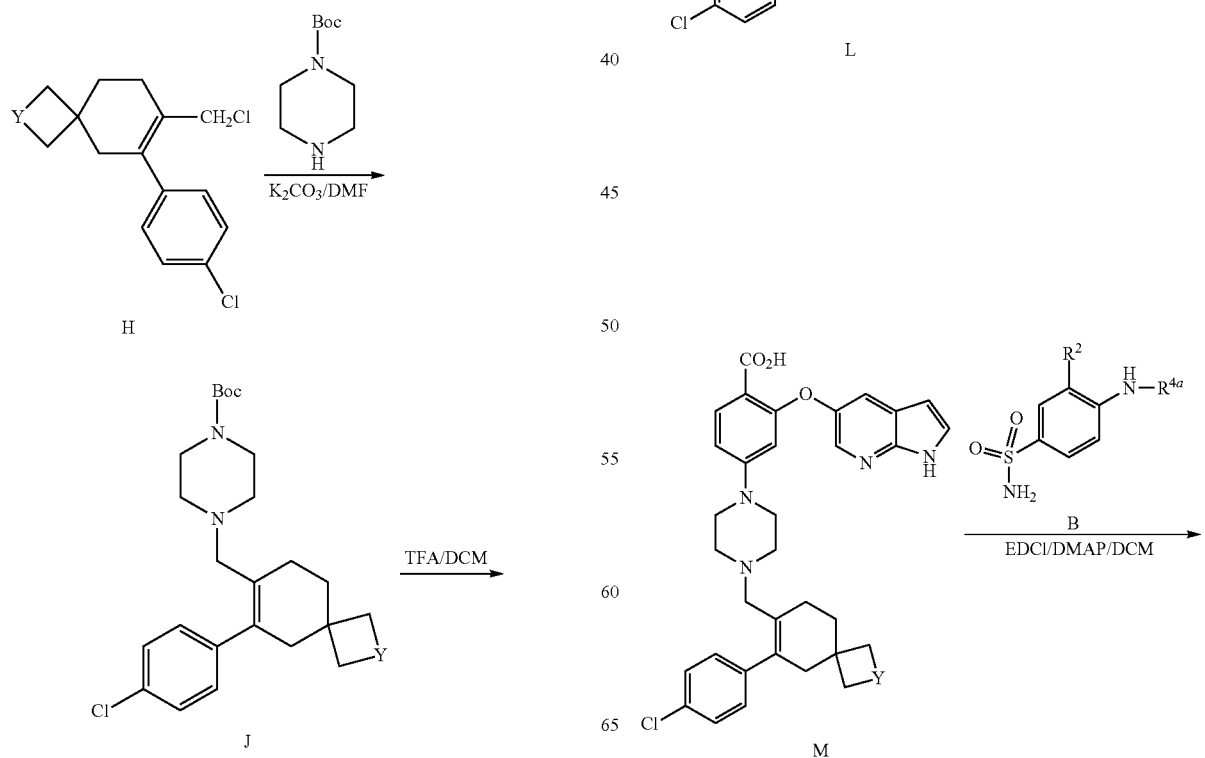

91

-continued

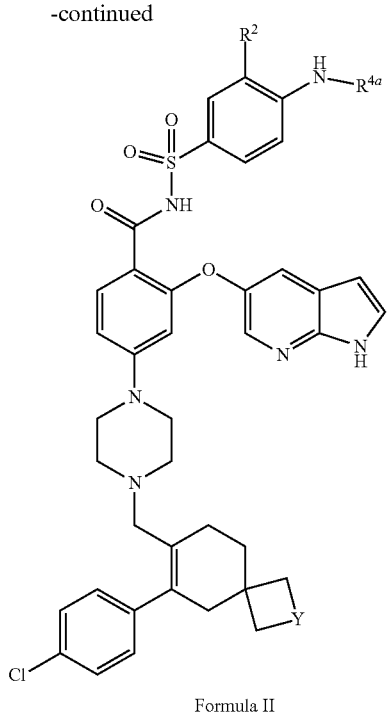

Formula II

In general Scheme 5, Compound H from General Scheme 3 is reacted with Boc-protected piperidine to give Compound J, and the Boc group is removed to give Compound K. Compound K is reacted with methyl 2-((1H-pyrrolo[2,3-b]pyridin-5-yl)oxy)-4-fluorobenzoate to give Compound L, and the ester of Compound L is hydrolyzed to give Compound M. Compound M is coupled with Compound B from General Scheme 1 to give a compound having Formula II.

EXAMPLES

Example 1

Synthetic Intermediates

Intermediate 1: Synthesis of 1-cyclobutylidenepropan-2-one

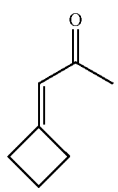

To a solution of cyclobutanone (5.0 g, 71.4 mmol) in toluene (200 ml) was added 1-(triphenylphosphoranylidene)-2-propanone (22.7 g, 71.4 mmol) and the mixture was refluxed overnight. Solvent was removed under reduced pressure and the residue was purified by silica gel column chromatography (ethyl acetate/hexane 1/10-1/5) to afford 1-cyclobutylidenepropan-2-one (5.0 g) as yellow oil. $^1$H NMR (400 MHz, CDCl$_3$) δ 5.95-5.93 (m, 1H), 3.19-3.13 (m, 2H), 2.91-2.84 (m, 2H), 2.21 (s, 3H), 2.21-2.11 (m, 2H).

92

Intermediate 2: Synthesis of Spiro[3.5]nonane-6,8-dione

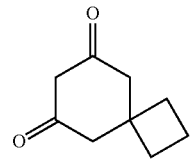 [SMILES: O=C1CC(=O)CC2(CCC2)C1]

To a solution of 1-cyclobutylidenepropan-2-one (23.1 g, 0.21 mol) and methyl malonate (30.3 g, 0.23 mol) in methanol (150 ml) was added sodium methoxide (41.4 g, 30% in methanol). The mixture was heated to reflux under N$_2$ for 4 h and concentrated. The resulting residue was hydrolyzed in 2 N potassium hydroxide (200 ml) at 70° C. for 4 h. The mixture was extracted with ethyl acetate (100 ml), then titrated to pH 3-5 with 1N hydrochloride. The resulting solution was heated to 70° C. for 5 h and extracted with ethyl acetate (100 ml×3). The combined organic layers were dried over magnesium sulfate and concentrated to afford spiro[3.5]nonane-6,8-dione (19.8 g, 62.3%) as yellow solid. This product was used directly in the next step without further purification. $^1$H NMR (400 MHz, DMSO-d6) δ 11.05 (s, 1H), 5.17 (s, 1H), 2.50-2.35 (m, 4H), 1.92-1.79 (m, 2H), 1.79-1.72 (m, 4H).

Intermediate 3: 8-Isobutoxyspiro[3.5]non-7-en-6-one

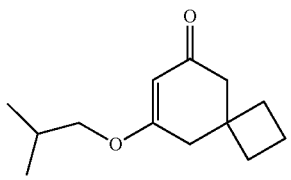

To a solution of spiro[3.5]nonane-6,8-dione (19.8 g, 0.13 mol) in toluene (150 ml) was added 4-toluenesulfonic acid (248 mg, 0.0013 mol) and iso-butyl alcohol (14.5 g, 0.2 mol). The mixture was heated to reflux and water was removed by azeotropic distillation. Solvent was removed under vacuum and the residue was purified by silica gel column chromatography (ethyl acetate/petrol ether 1/10-1/3) to afford 8-isobutoxyspiro[3.5]non-7-en-6-one (25.0 g, 92.7%) as light yellow oil. $^1$H NMR (400 MHz, CDCl$_3$) δ 5.31 (s, 1H), 3.59 (d, J=6.8 Hz, 2H), 2.51 (s, 2H), 2.45 (s, 2H), 2.12-1.96 (m, 1H), 1.93-1.83 (m, 6H), 0.99 (d, J=6.8 Hz, 6H).

Intermediate 4: Synthesis of Spiro[3.5]non-7-en-6-one

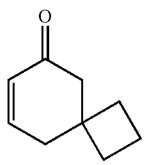

To a solution of 8-isobutoxyspiro[3.5]non-7-en-6-one (25.0 g, 0.12 mol) in toluene (100 ml) was added Red-Al® (40 ml, 70% in toluene, 0.18 mol) dropwise at room temperature. The mixture was heated to 45° C. for 4 h, then quenched by 1N hydrochloride. The mixture was filtered and the filtrate was concentrated and purified by silica gel column chromatography (ethyl acetate/petrol ether 1/10) to afford spiro[3.5]non-7-en-6-one (9.0 g, 55%) as light yellow oil.

Intermediate 5: Synthesis of Spiro[3.5]nonan-6-one

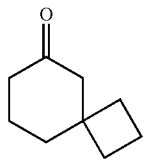

Spiro[3.5]non-7-en-6-one (9.0 g) was hydrogenated under 1 atm $H_2$ catalyzed by 10% Pd/C (1.0 g) in methanol (80 ml) for 5.5 h. Pd/C was removed by filtration and the filtrate was concentrated to afford spiro[3.5]nonan-6-one (8.8 g, 96.4%) as colorless oil which was used directly in the next step without further purification. $^1$H NMR (400 MHz, $CDCl_3$) δ 2.38 (s, 2H), 2.23-2.20 (m, 2H), 1.89-1.75 (m, 10H).

Intermediate 6: Synthesis of Methyl 6-oxospiro[3.5]nonane-7-carboxylate

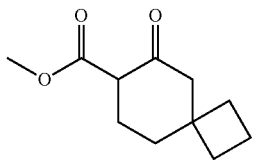

To a suspension of sodium hydride (5.1 g, 0.13 mol) in tetrahydrogen furan (150 ml) was added methyl carbonate (28.7 g, 0.32 mol) at room temperature, followed by spiro[3.5]nonan-6-one in tetrahydrogen furan (30 ml). The mixture was refluxed for 2 h. The reaction was quenched by saturated aqueous ammonium chloride and extracted with ethyl acetate (100 ml×3). The combined organic layers were washed with brine and concentrated. The resulting residue was purified by silica gel column chromatography to afford methyl 6-oxospiro[3.5]nonane-7-carboxylate (4.0 g, 32%) as light yellow oil.

Intermediate 7: Synthesis of Methyl 6-(((trifluoromethyl)sulfonyl)oxy) spiro[3.5]non-6-ene-7-carboxylate

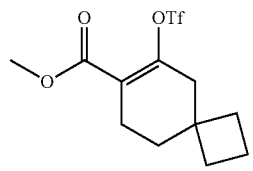 [SMILES: COC(=O)C1=C(OS(=O)(=O)C(F)(F)F)CC2(CCC2)CC1]

To a solution of methyl 6-oxospiro[3.5]nonane-7-carboxylate (4.0 g, 0.02 mol) in tetrahydrogen furan (25 ml) were added potassium carbonate (5.6 g, 0.04 mol) and N,N-bis(trifluoromethylsulfonyl)aniline (7.9 g, 0.022 mol). The mixture was stirred at room temperature overnight, diluted with water, and extracted with ethyl acetate (100 ml×3). The combined organic layers were washed with saturated brine, dried over magnesium sulfate and concentrated. The resulting residue was purified by silica gel column chromatography (ethyl acetate/petrol ether 1/50-1/10) to afford methyl 6-(((trifluoromethyl)sulfonyl)oxy)spiro[3.5]non-6-ene-7-carboxylate (5.0 g, 76%) as light yellow oil.

Intermediate 8: Synthesis of Methyl 6-(4-chlorophenyl)spiro[3.5]non-6-ene-7-carboxylate

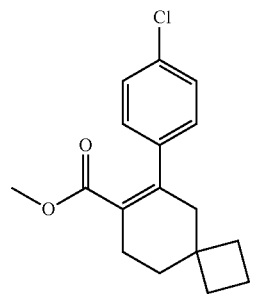 [SMILES: COC(=O)C1=C(c2ccc(Cl)cc2)CC2(CCC2)CC1]

The mixture of methyl 6-(((trifluoromethyl)sulfonyl)oxy)spiro[3.5]non-6-ene-7-carboxylate (5.0 g, 0.015 mol), 4-chlorophenyl boronic acid (2.58 g, 0.017 mol), CsF (4.63 g, 0.03 mol) and Pd(PPh$_3$)$_4$ (173 mg, 0.15 mol) in 1,2-dimethoxy-ethan (30 ml) and methanol (15 ml) was heated to 70° C. under $N_2$ for 2 h. Solvents were removed under reduced pressure and the residue was purified by silica gel column chromatography (ethyl acetate/petrol ether 1/10) to afford methyl 6-(4-chlorophenyl)spiro[3.5]non-6-ene-7-carboxylate (4.0 g, 92%) as colorless oil. $^1$H NMR (400 MHz, $CDCl_3$) δ 7.30 (d, J=8.5 Hz, 2H), 7.06 (d, J=8.5 Hz, 2H), 3.48 (s, 3H), 2.50-2.44 (m, 2H), 2.43 (t, J=2.3(2.3 or 6.3?) Hz, 2H), 2.02-1.80 (m, 6H), 1.74 (t, J=6.3 Hz, 2H).

Intermediate 9: Synthesis of (6-(4-Chlorophenyl)spiro[3.5]non-6-en-7-yl)methanol

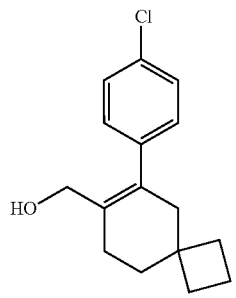 [SMILES: OCC1=C(c2ccc(Cl)cc2)CC2(CCC2)CC1]

To a solution methyl 6-(4-chlorophenyl)spiro[3.5]non-6-ene-7-carboxylate (4.0 g, 0.014 mol) in tetrahydrogen furan (20 ml) was added a solution of LiBH$_4$ (910 mg, 0.042 mol) in tetrahydrogen furan (10 ml). The mixture was stirred at room temperature overnight, quenched by 1N aqueous hydrochloride and extracted with ethyl acetate (100 ml×3). The combined organic layers were washed with brine, dried over magnesium sulfate and concentrated. The resulting residue was purified by silica gel column chromatography (ethyl acetate/petrol ether 1/10-1/3) to afford (6-(4-chlorophenyl)spiro[3.5]non-6-en-7-yl)methanol (3.0 g, 81.7%) as white solid. $^1$H NMR (400 MHz, CDCl$_3$) δ 7.31 (d, J=8.4 Hz, 2H), 7.09 (d, J=8.4 Hz, 2H), 3.93 (d, J=4.2 Hz, 2H), 2.37-2.26 (m, 2H), 2.01-1.77 (m, 8H), 1.74 (t, J=6.3 Hz, 2H).

Intermediate 10: Synthesis of 7-(Chloromethyl)-6-(4-chlorophenyl)spiro[3.5]non-6-ene

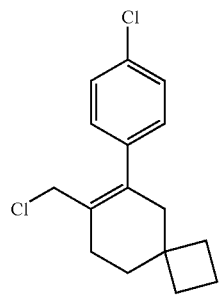 [SMILES: ClCC1=C(c2ccc(Cl)cc2)CC2(CCC2)CC1]

To a solution of (6-(4-chlorophenyl)spiro[3.5]non-6-en-7-yl)methanol (3.5 g, 0.013 mol) and trimethylamine (2.7 g, 0.026 mol) in dichloromethane (20 ml) was added methylsulfonyl chloride (3.0 g, 0.026 mol) dropwise. The mixture was stirred at room temperature for 5 h. Solvent was removed under reduced pressure and the residue was purified by silica gel column chromatography to afford 7-(chloromethyl)-6-(4-chlorophenyl)spiro[3.5]non-6-ene (2.75 g, 75.5%) as yellow oil. $^1$H NMR (400 MHz, CDCl$_3$) δ 7.31 (d, J=8.4 Hz, 2H), 7.09 (d, J=8.5 Hz, 2H), 3.93 (s, 2H), 2.34-2.25 (m, 4H), 1.97-1.78 (m, 6H), 1.74 (t, J=6.3 Hz, 2H).

Intermediate 11: Synthesis of Ethyl 2-((1H-pyrrolo[2,3-b]pyridin-5-yl)oxy)-4-fluorobenzoate

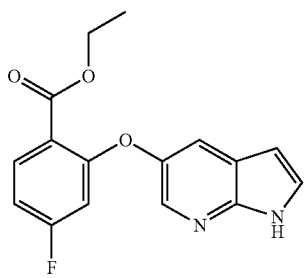 [SMILES: CCOC(=O)c1ccc(F)cc1Oc1cnc2[nH]ccc2c1]

A mixture of 1-(triisopropylsilyl)-1H-pyrrolo[2,3-b]pyridin-5-ol (2.2 g), ethyl 2,4-difluorobenzoate (1.96 g), and K$_3$PO$_4$ (2.14 g) in diglyme (20 mL) was stirred at 115° C. for 1 h. The reaction was cooled, diluted with ethyl acetate (100 mL), and washed with water, brine, and concentrated. The residue was purified by silica gel chromatography (ethyl acetate/hexane 1/3) to afford ethyl 2-((1H-pyrrolo[2,3-b]pyridin-5-yl)oxy)-4-fluorobenzoate (1.9 g) as white solid.

$^1$H NMR (400 MHz, CDCl$_3$) δ 10.13-10.08 (m, 1H), 8.23 (d, J=2.6 Hz, 1H), 7.98 (dd, J=8.8, 6.6 Hz, 1H), 7.67 (d, J=2.6 Hz, 1H), 7.44 (dd, J=3.5, 2.5 Hz, 1H), 6.84 (ddd, J=8.8, 7.6, 2.4 Hz, 1H), 6.55 (dd, J=10.3, 2.4 Hz, 1H), 6.52 (dd, J=3.5, 2.0 Hz, 1H), 4.38 (q, J=7.1 Hz, 2H), 1.36 (t, J=7.1 Hz, 3H).

Intermediate 12: Synthesis of Methyl 2-((1H-pyrrolo[2,3-b]pyridin-5-yl)oxy)-4-bromobenzoate

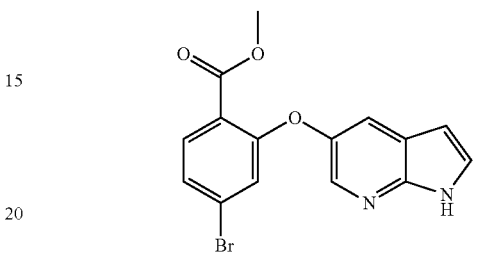

A mixture of 1-(triisopropylsilyl)-1H-pyrrolo[2,3-b]pyridin-5-ol (1.91 g), methyl 4-bromo-2-fluorobenzoate (1.70 g), and K$_3$PO$_4$ (1.86 g) in diglyme (20 mL) was stirred at 115° C. for 1 h. The reaction was cooled, diluted with ethyl acetate (100 mL), and washed with water, brine, and concentrated. The residue was purified by silica gel chromatography (ethyl acetate/hexane 1/3) to afford methyl 2-((1H-pyrrolo[2,3-b]pyridin-5-yl)oxy)-4-bromobenzoate (1.8 g) as white solid. $^1$H NMR (400 MHz, CDCl$_3$) δ 9.28 (s, 1H), 8.18 (d, J=2.5 Hz, 1H), 7.79 (d, J=8.4 Hz, 1H), 7.62 (d, J=2.5 Hz, 1H), 7.40-6.96 (m, 2H), 6.96 (d, J=1.7 Hz, 1H), 6.51-6.48 (m, 1H), 3.89 (s, 3H).

Intermediate 13: Synthesis of 2-((1H-pyrrolo[2,3-b]pyridin-5-yl)oxy)-4-bromobenzoic Acid

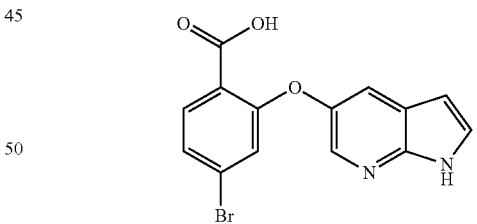

To a solution of methyl 2-((1H-pyrrolo[2,3-b]pyridin-5-yl)oxy)-4-bromobenzoate (300 mg, 0.867 mmol) in dioxane (10 mL) was added 1 N NaOH (2.2 mL, 2.2 mmol) and the mixture was stirred at room temperature for 2 h. The mixture was acidified by 1 N HCl and extracted with ethyl acetate, washed with brine, and dried over anhydrous MgSO$_4$. Evaporation under reduced pressure afforded crude 2((1H-pyrrolo[2,3-b]pyridin-5-yl)oxy)-4-bromobenzoic acid as a colorless oil. This product was used directly in the next step without further purification.

Intermediate 14: Synthesis of 2-((1H-pyrrolo[2,3-b]pyridin-5-yl)oxy)-4-bromo-N-((3-nitro-4-(((tetrahydro-2H-pyran-4-yl)methyl)amino)phenyl) sulfonyl) benzamide

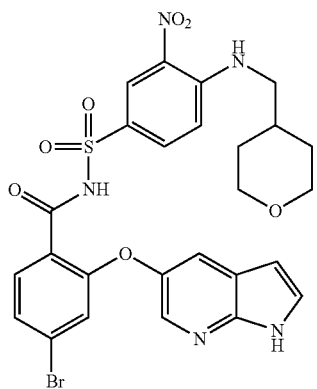 [SMILES: O=C(NS(=O)(=O)c1ccc(NCC2CCOCC2)c([N+](=O)[O-])c1)c1ccc(Br)cc1Oc1cnc2[nH]ccc2c1]

To a solution of 2-((1H-pyrrolo[2,3-b]pyridin-5-yl)oxy)-4-bromobenzoic acid (100 mg, 0.3 mmol) in DCM (10 mL) were added 3-nitro-4-(((tetrahydro-2H-pyran-4-yl)methyl)amino)benzenesulfonamide (95 mg, 0.3 mmol), DMAP (55 mg, 0.45 mmol) and EDCI (115 mg, 0.6 mmol) and the mixture was stirred at room temperature for 24 h. Solvent was removed under reduced pressure and the residue was purified by silica gel chromatography (DCM/MeOH 95/5) to afford 2-((1H-pyrrolo[2,3-b]pyridin-5-yl)oxy)-4-bromo-N-((3-nitro-4-(((tetrahydro-2H-pyran-4-yl)methyl)amino)phenyl) sulfonyl)benzamide as a yellow oil (80 mg). MS m/z 630 [M+H]$^+$.

Intermediate 15: Synthesis of (S)—N-((4-(((1,4-Dioxan-2-yl)methyl)amino)-3-nitrophenyl)sulfonyl)-2-((1H-pyrrolo[2,3-b]pyridin-5-yl)oxy)-4-bromobenzamide

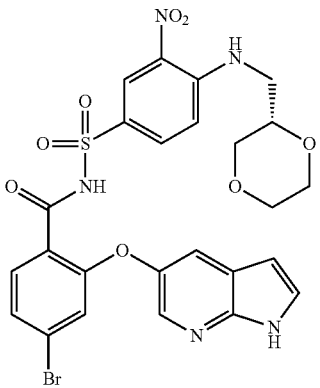 [SMILES: O=C(NS(=O)(=O)c1ccc(NC[C@H]2COCCO2)c([N+](=O)[O-])c1)c1ccc(Br)cc1Oc1cnc2[nH]ccc2c1]

The title compound was prepared using a procedure similar to the one described for INTERMEDIATE 14, and purified by silica gel chromatography (DCM/MeOH 95/5). $^1$H NMR (400 MHz, DMSO-d6) δ 11.79 (s, 1H), 8.59-8.52 (m, 2H), 8.05 (d, J=2.6 Hz, 1H), 7.85 (dd, J=9.2, 2.4 Hz, 1H), 7.66 (d, J=2.6 Hz, 1H), 7.59-7.49 (m, 1H), 7.48 (d, J=8.2 Hz, 1H), 7.34 (dd, J=8.2, 1.8 Hz, 1H), 7.12 (d, J=9.2 Hz, 1H), 6.88 (d, J=1.8 Hz, 1H), 6.50-6.40 (m, 1H), 3.83-3.37 (m, 2H), 3.72-3.56 (m, 2H), 3.56-3.42 (m, 2H), 3.37-3.01 (m, 3H).

Intermediate 16: Synthesis of (R)—N-((4-(((1,4-dioxan-2-yl)methyl)amino)-3-nitrophenyl) sulfonyl)-2-((1H-pyrrolo[2,3-b]pyridin-5-yl)oxy)-4-bromobenzamide

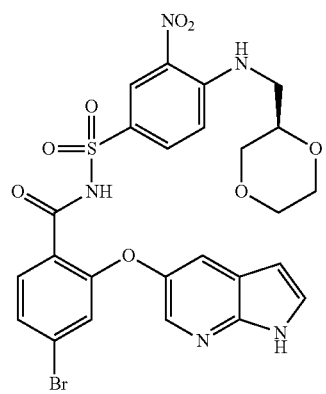 [SMILES: O=C(NS(=O)(=O)c1ccc(NC[C@@H]2COCCO2)c([N+](=O)[O-])c1)c1ccc(Br)cc1Oc1cnc2[nH]ccc2c1]

The title compound was prepared using a procedure similar to the one described for INTERMEDIATE 14, and purified by silica gel chromatography (DCM/MeOH 95/5). $^1$H NMR (400 MHz, DMSO-d6) δ 11.79 (s, 1H), 8.59-8.52 (m, 2H), 8.05 (d, J=2.6 Hz, 1H), 7.85 (dd, J=9.2, 2.4 Hz, 1H), 7.66 (d, J=2.6 Hz, 1H), 7.59-7.49 (m, 1H), 7.48 (d, J=8.2 Hz, 1H), 7.34 (dd, J=8.2, 1.8 Hz, 1H), 7.12 (d, J=9.2 Hz, 1H), 6.88 (d, J=1.8 Hz, 1H), 6.50-6.40 (m, 1H), 3.83-3.37 (m, 2H), 3.72-3.56 (m, 2H), 3.56-3.42 (m, 2H), 3.37-3.01 (m, 3H).

Intermediate 17: Synthesis of 2-((1H-pyrrolo[2,3-b]pyridin-5-yl)oxy)-4-bromo-N-((3-nitro-4-(((1-(oxetan-3-yl)piperidin-4-yl)methyl)amino)phenyl)sulfonyl)benzamide

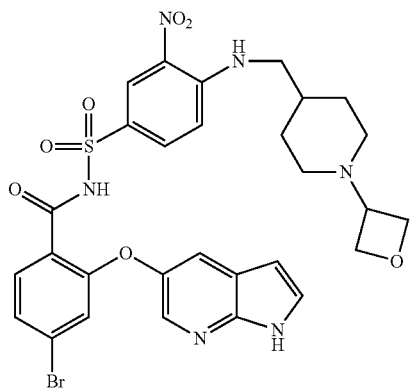 [SMILES: O=C(NS(=O)(=O)c1ccc(NCC2CCN(C3COC3)CC2)c([N+](=O)[O-])c1)c1ccc(Br)cc1Oc1cnc2[nH]ccc2c1]

The title compound was prepared using a procedure similar to the one described for INTERMEDIATE 14, and purified by silica gel chromatography (DCM/MeOH 95/5). MS m/z 685 [M+H]$^+$.

Intermediate 18: Synthesis of 2-((1H-pyrrolo[2,3-b]pyridin-5-yl)oxy)-4-bromo-N-((4-(((4-morpholinocyclohexyl)methyl)amino)-3-nitrophenyl)sulfonyl)benzamide

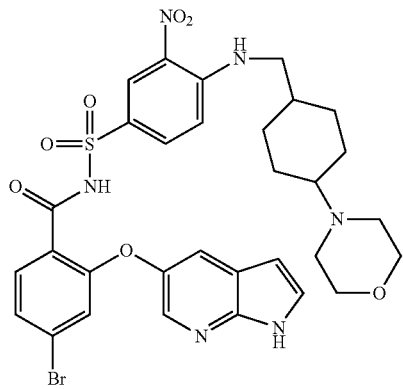

The title compound was prepared using a procedure similar to the one described for INTERMEDIATE 14, and purified by silica gel chromatography (DCM/MeOH 95/5). MS m/z 713 [M+H]+.

Intermediate 19: Synthesis of 2-((1H-pyrrolo[2,3-b]pyridin-5-yl)oxy)-4-bromo-N-((3-nitro-4-(((1-(tetrahydro-2H-pyran-4-yl)piperidin-4-yl)methyl)amino)phenyl)sulfonyl)benzamide

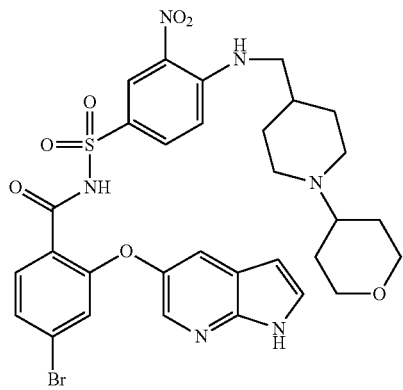 [SMILES: O=C(NS(=O)(=O)c1ccc(NCC2CCC(N3CCOCC3)CC2)c([N+](=O)[O-])c1)c1ccc(Br)cc1Oc1cnc2[nH]ccc2c1]

The title compound was prepared using a procedure similar to the one described for INTERMEDIATE 14, and purified by silica gel chromatography (DCM/MeOH 95/5). MS m/z 713 [M+H]+.

Intermediate 20: Synthesis of 2-((1H-pyrrolo[2,3-b]pyridin-5-yl)oxy)-4-bromo-N-((3-nitro-4-(((tetrahydro-2H-pyran-3-yl)methyl)amino)phenyl)sulfonyl) benzamide

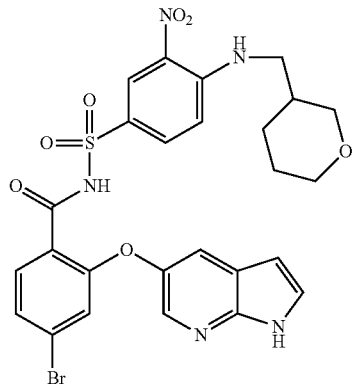 [SMILES: O=C(NS(=O)(=O)c1ccc(NCC2CCCOC2)c([N+](=O)[O-])c1)c1ccc(Br)cc1Oc1cnc2[nH]ccc2c1]

The title compound was prepared using a procedure similar to the one described for INTERMEDIATE 14, and purified by silica gel chromatography (DCM/MeOH 95/5). MS m/z 630 [M+H]+.

Intermediate 21: Synthesis of 2-((1H-pyrrolo[2,3-b]pyridin-5-yl)oxy)-4-bromo-N-((4-(((1-methylpiperidin-4-yl)methyl)amino)-3-nitrophenyl)sulfonyl) benzamide

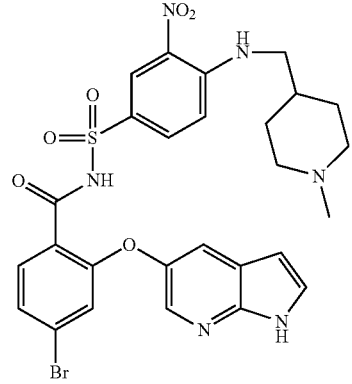 [SMILES: CN1CCC(CNc2ccc(S(=O)(=O)NC(=O)c3ccc(Br)cc3Oc3cnc4[nH]ccc4c3)cc2[N+](=O)[O-])CC1]

The title compound was prepared using a procedure similar to the one described for INTERMEDIATE 14, and purified by silica gel chromatography (DCM/MeOH 95/5). MS m/z 643 [M+H]+.

Intermediate 23: Synthesis of tert-Butyl-4-(3-((1H-pyrrolo[2,3-b]pyridin-5-yl)oxy)-4-(ethoxycarbonyl)phenyl)piperazine-1-carboxylate

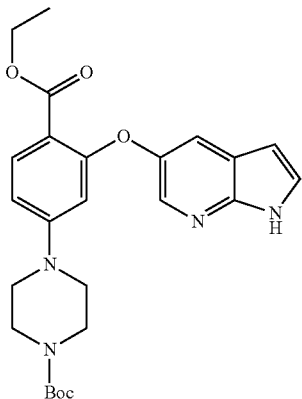 [SMILES: CCOC(=O)c1ccc(N2CCN(C(=O)OC(C)(C)C)CC2)cc1Oc1cnc2[nH]ccc2c1]

The mixture of ethyl 2-((1H-pyrrolo[2,3-b]pyridin-5-yl)oxy)-4-fluorobenzoate (2.1 g, 7 mmol), N-Boc-piperazine (2.61 g, 0.014 mol) and dipotassium hydrogenphosphate (2.44 g, 0.014 mol) in dimethyl sulfoxide was heated to 135° C. overnight. Water was added to the reaction mixture and the mixture was extracted with ethyl acetate (50 ml×3). The combined organic layers were washed with brine, concentrated and purified by silica gel column chromatography to afford tert-butyl 4-(3-((1H-pyrrolo[2,3-b]pyridin-5-yl)oxy)-4-(ethoxycarbonyl)phenyl)piperazine-1-carboxylate (2.4 g, 73%) as white solid. $^1$H NMR (400 MHz, CDCl$_3$) δ 9.42 (br s, 1H), 8.20 (d, J=2.5 Hz, 1H), 7.95 (d, J=8.9 Hz, 1H), 7.53 (d, J=2.5 Hz, 1H), 7.37 (dd, J=3.5, 2.5 Hz, 1H), 6.66 (dd, J=8.9, 2.5 Hz, 1H), 6.46 (dd, J=3.5, 2.0 Hz, 1H), 6.36 (d, J=2.5 Hz, 1H), 4.28 (q, J=7.1 Hz, 2H), 3.55-3.50 (m, 4H), 3.21-3.17 (m, 4H), 1.47 (s, 9H), 1.26 (t, J=7.1 Hz, 3H).

Intermediate 24: Synthesis of Ethyl 2-((1H-pyrrolo[2,3-b]pyridin-5-yl)oxy)-4-(piperazin-1-yl)benzoate

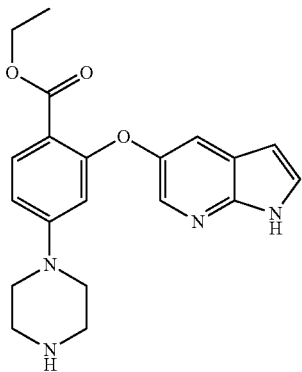

Trifluoroacetic acid (6 ml) was added to a solution of tert-butyl 4-(3-((1H-pyrrolo[2,3-b]pyridin-5-yl)oxy)-4-(ethoxycarbonyl)phenyl)piperazine-1-carboxylate (2.1 g) in dichloromethane (10 ml) and the mixture was stirred at room temperature for 3 h. Solvent was removed under reduced pressure and the crude ethyl 2-((1H-pyrrolo[2,3-b]pyridin-5-yl)oxy)-4-(piperazin-1-yl)benzoate (2.5 g) was used directly in the next step without further purification.

Intermediate 25: Synthesis of Ethyl 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoate

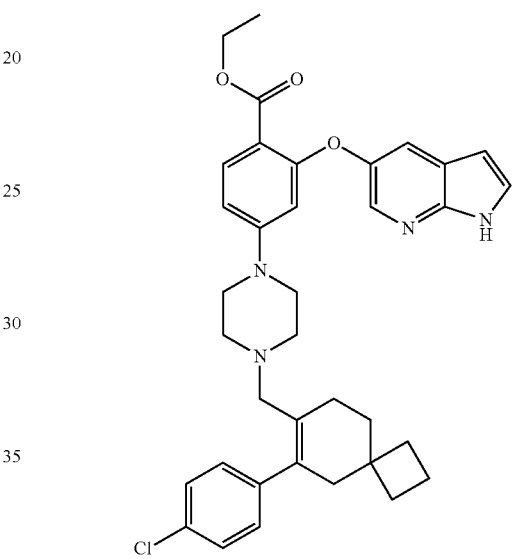

To a solution of 7-(chloromethyl)-6-(4-chlorophenyl)spiro[3.5]non-6-ene (851 mg, 3 mmol) in N,N-dimethylformamide (10 ml) were added potassium carbonate (1.26 g, 9 mmol), potassium iodide (100 mg, 0.6 mmol) and ethyl 2-((1H-pyrrolo[2,3-b]pyridin-5-yl)oxy)-4-(piperazin-1-yl)benzoate (1.53 g, 3.3 mmol). The mixture was stirred at room temperature overnight. The reaction mixture was diluted with water and extracted with ethyl acetate (50 ml×3). The combined organic layers were washed with brine, concentrated and purified by silica gel column chromatography (ethyl acetate/petrol ether 1/5-1/1) to afford ethyl 2-((1H-pyrrolo[2,3-b]pyridin-5-yl)oxy)-4-(4-((6-(4-chlorophenyl)spiro[3.5]non-6-en-7-yl)methyl) piperazin-1-yl)benzoate (1.3 g, 71%) as white solid. $^1$H NMR (400 MHz, CDCl$_3$) δ 9.98 (s, 1H), 8.20 (d, J=2.6 Hz, 1H), 7.91 (d, J=9.0 Hz, 1H), 7.51 (d, J=2.6 Hz, 1H), 7.38 (t, J=3.5 Hz, 1H), 7.28 (d, J=8.3 Hz, 2H), 6.97 (d, J=8.3 Hz, 2H), 6.62 (dd, J=9.0, 2.5 Hz, 1H), 6.45 (dd, J=3.5, 2.0 Hz, 1H), 6.32 (d, J=2.5 Hz, 1H), 4.26 (q, J=7.1 Hz, 2H), 3.20-3.12 (m, 4H), 2.77 (s, 2H), 2.31-2.17 (m, 8H), 1.98-1.72 (m, 6H), 1.68 (t, J=6.3 Hz, 2H), 1.25 (t, J=7.1 Hz, 3H).

Intermediate 26: Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid

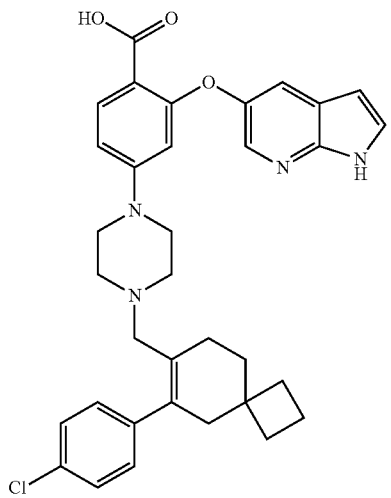

The solution of ethyl 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoate (1.3 g, 2.1 mmol) and 2N potassium hydroxide (12 ml, 0.042 mol) in dioxane (15 ml) was heated to 60° C. overnight. The mixture was neutralized with 1N aqueous hydrochloride to pH 7 and extracted with ethyl acetate (50 ml×3). The combined organic layers were washed with brine, dried over magnesium sulfate, and concentrated to afford 2-((1H-pyrrolo[2,3-b]pyridin-5-yl)oxy)-4-(4-((6-(4-chlorophenyl) spiro[3.5]non-6-en-7-yl)methyl)piperazin-1-yl)benzoic acid (1.1 g, 88.7%) as white solid. $^1$H NMR (400 MHz, CDCl$_3$) δ 10.34 (s, 1H), 8.19 (d, J=2.6 Hz, 1H), 8.02 (d, J=9.0 Hz, 1H), 7.63 (d, J=2.6 Hz, 1H), 7.38-7.34 (m, 1H), 7.27 (d, J=8.3 Hz, 2H), 6.96 (d, J=8.3 Hz, 2H), 6.63 (dd, J=9.0, 2.4 Hz, 1H), 6.44 (dd, J=3.5, 1.5 Hz, 1H), 6.22 (d, J=2.4 Hz, 1H), 3.81 (s, 2H), 3.17-3.10 (m, 4H), 2.80 (s, 2H), 2.30-2.20 (m, 6H), 1.98-1.72 (m, 6H), 1.67 (t, J=6.3 Hz, 2H).

Intermediate 27: Synthesis of 1-(Oxetan-3-ylidene)propan-2-one

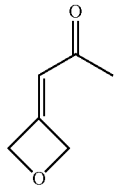

To a solution of oxetan-3-one (20.6 g, 0.28 mol) in DCM (300 mL) was added 1-(triphenylphosphoranylidene)propan-2-one (98.6 g, 0.31 mol). The mixture was stirred at room temperature overnight. DCM was removed under reduced pressure until solid was precipitated. The solid was removed by filtration and the filtrate was concentrated and purified by silica gel column chromatography (ethyl acetate/heptane 1/5-1/3) to afford 1-(oxetan-3-ylidene)propan-2-one (23.3 g, 74.3%) as yellow oil.

Intermediate 28: Synthesis of 2-Oxaspiro[3.5]nonane-6,8-dione

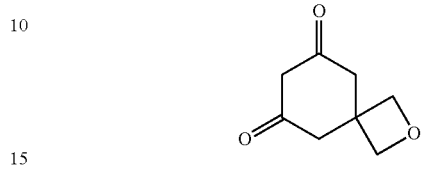

To a solution of 1-(oxetan-3-ylidene)propan-2-one (23.3 g, 0.21 mol) and methyl malonate (30.2 g, 0.23 mol) in methanol (150 mL) was added sodium methoxide (41.3 g, 30% MeOH solution). The mixture was heated to reflux under N$_2$ for 1 h. Solvent was removed under reduced pressure to afford methyl 6-hydroxy-8-oxo-2-oxaspiro[3.5]non-6-ene-5-carboxylate which was used in the next step directly without purification. To an aqueous solution of KOH (2 mol/L, 200 ml) was added methyl 6-hydroxy-8-oxo-2-oxaspiro[3.5]non-6-ene-5-carboxylate. After stirring at room temperature for 30 min, the aqueous solution was extracted with ethyl acetate (150 ml×3). The aqueous layer was adjusted to pH 3-5 with 1 N hydrochloride and heated at 50° C. for 4 h. Water was removed under reduced pressure and the residue was purified by silica gel column chromatography to afford 2-oxaspiro[3.5]nonane-6,8-dione (2.5 g, 77.0%) as light yellow solid. This product was used directly in the next step without further purification.

Intermediate 29: Synthesis of 8-Isobutoxy-2-oxaspiro[3.5]non-7-en-6-one

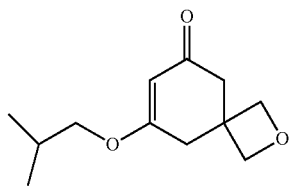

To a solution of 2-oxaspiro[3.5]nonane-6,8-dione (25 g, 0.16 mol) in toluene (150 ml) were added TsOH (238 mg, 0.0016 mol) and isobutyl alcohol (18 g, 0.24 mol). The reaction was completed after stirring at room temperature for 1 h. Solvent was removed under reduced pressure and the residue was purified by silica gel column chromatography (ethyl acetate/petrol ether 1/5-1/3) to afford 8-isobutoxy-2-oxaspiro[3.5]non-7-en-6-one (6 g, 43%) as light yellow oil. $^1$H NMR (400 MHz, CDCl$_3$) δ 5.34 (s, 1H), 4.47 (d, J=6.1 Hz, 2H), 4.45 (d, J=6.1 Hz, 2H), 3.60 (d, J=6.8 Hz 2H), 2.80 (s, 2H), 2.68 (s, 2H), 2.09-2.01 (m, 1H), 0.98 (d, J=6.8 Hz, 6H).

Intermediate 30: Synthesis of 2-Oxaspiro[3.5]non-7-en-6-one

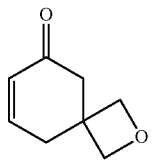

To a solution of 8-isobutoxy-2-oxaspiro[3.5]non-7-en-6-one (14.7 g, 0.07 mol) in toluene (100 ml) was added Red-Al® (40.4 g, 70% in Toluene) dropwise. The mixture was heated to 45° C. for 2 h and quenched by 1N HCl solution. The mixture was concentrated and purified by silica gel column chromatography (ethyl acetate/petrol ether 1/10-1/5) to afford 2-oxaspiro[3.5]non-7-en-6-one (8.8 g, 91%) as colorless oil. This product was used directly in the next step without further purification.

Intermediate 31: Synthesis of 2-Oxaspiro[3.5]nonan-6-one

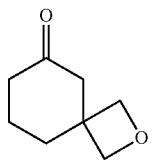

To a solution of 2-oxaspiro[3.5]non-7-en-6-one (8.8 g) in tetrahydrogen furan (80 ml) was added Pd/C (1 g). The mixture was hydrogenated under 1 atm $H_2$ at room temperature for 2 h. After the reaction was completed, Pd/C was removed by filtration and the solution was concentrated to afford 2-oxaspiro[3.5]nonan-6-one (8.0 g, 89.6%) as colorless oil. This product was used directly in the next step without further purification.

Intermediate 32: Synthesis of Methyl 6-oxo-2-oxaspiro[3.5]nonane-7-carboxylate

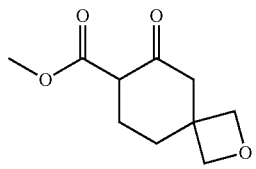

To a suspension of sodium hydride (4.6 g, 0.11 mol) in tetrahydrogen furan (150 ml) under $N_2$ was added methyl carbonate (25.7 g, 0.28 mol) dropwise. After dropping was completed, the mixture was heated to reflux. A solution of 2-oxaspiro[3.5]nonan-6-one (11.2 g, 0.057 mol) in tetrahydrogen furan (30 ml) was then added. The reaction was heated at reflux for 2 h and quenched by saturated aqueous ammonium chloride, and extracted with ethyl acetate (100 ml×3). The combined organic layer was washed with brine, concentrated under reduced pressure and the residue was purified by silica gel column chromatography to afford methyl 6-oxo-2-oxaspiro[3.5]nonane-7-carboxylate (4.5 g, 69%) as colorless oil. This product was used directly in the next step without further purification.

Intermediate 33: Synthesis of Methyl 6-(((trifluoromethyl)sulfonyl)oxy)-2-oxaspiro[3.5]non-6-ene-7-carboxylate

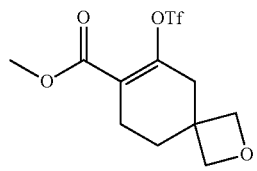 [SMILES: COC(=O)C1=C(OS(=O)(=O)C(F)(F)F)CC2(CC1)COC2]

To a suspension of methyl 6-oxo-2-oxaspiro[3.5]nonane-7-carboxylate (4.5 g, 0.02 mol) and potassium carbonate (6.3 g, 0.046 mol) in DMF (30 ml) was added N,N-bis(trifluoromethylsulfonyl)aniline (8.9 g, 0.025 mol). The mixture was stirred at room temperature overnight, diluted with water, and extracted with ethyl acetate (100 ml×3). The combined organic layer was washed with brine, dried over $MgSO_4$, and concentrated under reduced pressure. The residue was purified by silica gel column chromatography (ethyl acetate/Petrol ether 1/10-1/3) to afford methyl 6-(((trifluoromethyl)sulfonyl)oxy)-2-oxaspiro[3.5]non-6-ene-7-carboxylate (6.6 g, 86%) as light yellow oil. This product was used directly in the next step without further purification.

Intermediate 34: Synthesis of Methyl 6-(4-chlorophenyl)-2-oxaspiro[3.5]non-6-ene-7-carboxylate

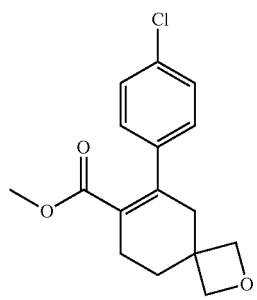 [SMILES: COC(=O)C1=C(c2ccc(Cl)cc2)CC2(CC1)COC2]

To a solution of methyl 6-(((trifluoromethyl)sulfonyl)oxy)-2-oxaspiro[3.5]non-6-ene-7-carboxylate (6.6 g, 0.02 mol) in 1,2-dimethoxy-ethan (30 ml) and methanol (10 ml) were added 4-chloro-phenyl boronic acid (3.13 g, 0.02 mol), CsF (6.08 g, 0.04 mol) and Pd(PPh$_3$)$_4$ (231 mg, 0.2 mmol) and the mixture was heated to 70° C. under $N_2$ for 30 min. Solvents were removed under reduced pressure and the residue was purified by silica gel column chromatography (ethyl acetate/petrol ether 1/5-1/3) to afford methyl 6-(4-chlorophenyl)-2-oxaspiro[3.5]non-6-ene-7-carboxylate (5.1 g, 87.3%) as light yellow solid. $^1$H NMR (400 MHz, CDCl$_3$) 7.33 (d, J=8.4 Hz, 2H), 7.07 (d, J=8.4 Hz, 2H), 4.54 (d, J=5.6 Hz, 2H), 4.48 (d, J=5.6 Hz, 2H), 3.48 (s, 3H), 2.74-2.70 (m, 2H), 2.55-2.50 (m, 2H), 2.04 (t, J=6.4 Hz, 2H).

Intermediate 35: Synthesis of (6-(4-Chlorophenyl)-2-oxaspiro[3.5]non-6-en-7-yl)methanol

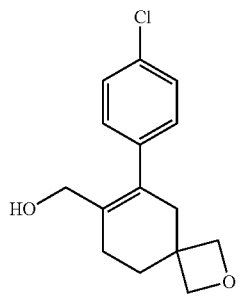 [SMILES: OCC1=C(c2ccc(Cl)cc2)CC2(CC1)COC2]

To a solution of methyl 6-(4-chlorophenyl)-2-oxaspiro[3.5]non-6-ene-7-carboxylate (2.1 g, 0.0072 mol) in tetrahydrogen furan (20 ml) was added LiBH$_4$ (475 mg, 0.022 mol) in tetrahydrogen furan (10 ml) dropwise at room temperature. The mixture was stirred at room temperature for 4 h, quenched by 1N HCl solution, and extracted with ethyl acetate (100 ml×3). The combined organic layers were washed with brine, dried over MgSO$_4$ and concentrated. The residue was purified by silica gel column chromatography (ethyl acetate/petrol ether 1/5-1/1) to afford (6-(4-chlorophenyl)-2-oxaspiro[3.5]non-6-en-7-yl)methanol (1.5 g, 78.9%) as white solid. $^1$H NMR (400 MHz, CDCl$_3$) 7.34 (d, J=8.4 Hz, 2H), 7.07 (d, 2H, J=8.4 Hz), 4.54 (d, 2H, J=6.0 Hz), 4.46 (d, 2H, J=5.6 Hz), 3.93 (s, 2H), 2.62 (s, 2H), 2.40-2.33 (m, 2H), 2.03 (t, 2H, J=6.4 Hz).

Intermediate 36: Synthesis of 7-(Chloromethyl)-6-(4-chlorophenyl)-2-oxaspiro[3.5]non-6-ene

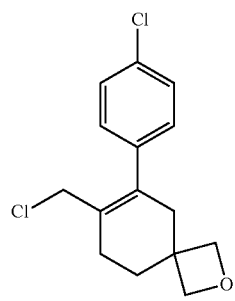 [SMILES: ClCC1=C(c2ccc(Cl)cc2)CC2(CC1)COC2]

To a solution of (6-(4-chlorophenyl)-2-oxaspiro[3.5]non-6-en-7-yl)methanol (1.5 g, 5.7 mmol) and triethylamine (836 mg, 8.6 mmol) in dichloromethane (15 ml) was added methylsulfonyl chloride (980 mg, 8.6 mmol) and the mixture was stirred at room temperature for 3.5 h. Solvent was removed under reduced pressure and the residue was purified by silica gel column chromatography to afford 7-(chloromethyl)-6-(4-chlorophenyl)-2-oxaspiro[3.5]non-6-ene (1.4 g, 87.0%) as white solid. $^1$H NMR (400 MHz, CDCl$_3$) 7.35 (d, 2H, J=8.4 Hz), 7.16 (d, 2H, J=8.4 Hz), 4.53 (d, 2H, J=6.0 Hz), 4.45 (d, 2H, J=5.6 Hz), 3.86 (s, 2H), 2.64 (s, 2H), 2.40-2.33 (m, 2H), 2.03 (t, 2H, J=6.4 Hz).

Intermediate 37: Synthesis of Ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate

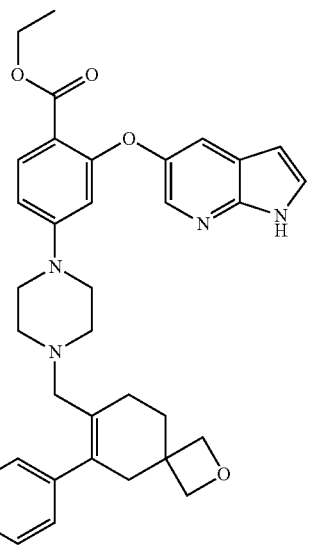

To a solution of ethyl 2-((1H-pyrrolo[2,3-b]pyridin-5-yl)oxy)-4-(piperazin-1-yl)benzoate (382 mg, 0.82 mmol) in DMF (10 ml) were added 7-(chloromethyl)-6-(4-chlorophenyl)-2-oxaspiro[3.5]non-6-ene (200 mg, 0.75 mmol), potassium carbonate (310 mg, 2.25 mmol), DIPEA (290 mg, 2.25 mmol) and potassium iodide (24.9 mg, 0.15 mmol) and the mixture was stirred at room temperature overnight. The mixture was diluted with water and extracted with ethyl acetate (50 ml×3). The combined organic layers were washed with brine, concentrated and purified by silica gel column chromatography (ethyl acetate/petrol ether 1/5-1/1) to afford ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate (370 mg, 80.6%) as white solid. MS m/z 613 [M+H]±.

Intermediate 38: Synthesis of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid

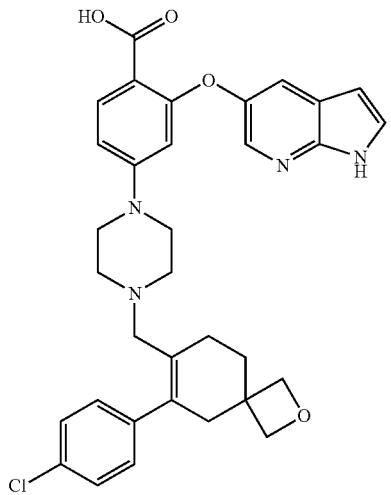

To a solution of ethyl 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoate (370 mg, 0.6 mmol) in dioxane (10 ml) was added 2 N potassium hydroxide (6 ml, 12 mmol) and the mixture was stirred at 60° C. overnight. The solution was neutralized with 1 N hydrochloride to pH 7 and extracted with ethyl acetate (100 ml×3). The combined organic layers were washed with brine, dried over magnesium sulfate and concentrated to afford 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (1.1 g, 88.7%) as white solid. MS m/z 585 [M+H]+.

Intermediate 55: Synthesis of Methyl 2-((1H-pyrrolo[2,3-b]pyridin-5-yl)oxy)-4-(1-((6-(4-chlorophenyl)spiro[3.5]non-6-en-7-yl)methyl)piperidin-4-yl)benzoate

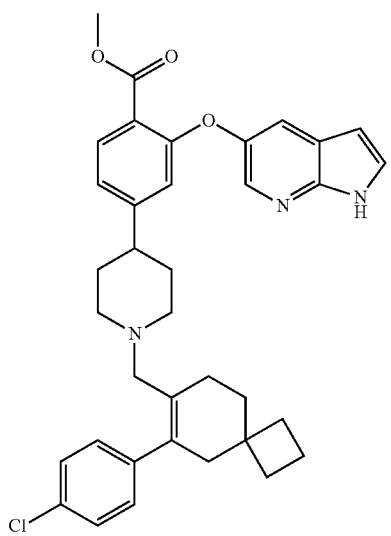 [SMILES: COC(=O)c1ccc(C2CCN(CC3=C(c4ccc(Cl)cc4)CC4(CCC4)CC3)CC2)cc1Oc1cnc2[nH]ccc2c1]

To as solution of 7-(chloromethyl)-6-(4-chlorophenyl)spiro[3.5]non-6-ene (850 mg, 3.04 mmol) in N,N-dimethylformamide (10 ml) were added potassium carbonate (1.26 g, 2.2 mmol), potassium iodide (100 mg, 0.61 mmol), and methyl 2-((1H-pyrrolo[2,3-b]pyridin-5-yl)oxy)-4-(piperidin-4-yl)benzoate (1.0 g, 3.34 mmol) the mixture was stirred at room temperature overnight. Then the mixture was diluted with water and extracted with ethyl acetate. The combined organic layers were washed with brine, concentrated. The resulting residue was purified by silica gel column chromatography to afford methyl 2-((1H-pyrrolo[2,3-b]pyridin-5-yl)oxy)-4-(1-((6-(4-chlorophenyl)spiro[3.5]non-6-en-7-yl)methyl)piperidin-4-yl)benzoate (1.0 g, 55.2%) as light yellow solid. $^1$H NMR (400 MHz, CDCl$_3$) δ 9.39 (br s, 1H), 8.19 (d, J=2.6 Hz, 1H), 7.87 (d, J=8.1 Hz, 1H), 7.57 (d, J=2.6 Hz, 1H), 7.39 (dd, J=3.5, 2.5 Hz, 1H), 7.30-7.23 (m, 2H), 7.04-6.93 (m, 3H), 6.72 (d, J=1.6 Hz, 1H), 6.49 (dd, J=3.5, 2.0 Hz, 1H), 3.87 (s, 3H), 2.81-2.75 (m, 2H), 2.73-2.71 (m, 2H), 2.28 (s, 2H), 2.25-2.15 (m, 2H), 1.98-1.76 (m, 6H), 1.75-1.51 (m, 9H).

Example 2

Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide

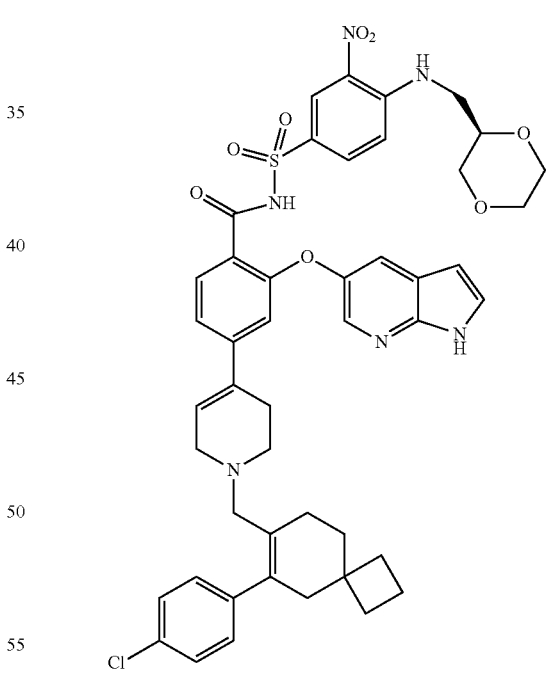

To a solution of (R)—N-((4-(((1,4-dioxan-2-yl)methyl)amino)-3-nitrophenyl) sulfonyl)-2-((1H-pyrrolo[2,3-b]pyridin-5-yl)oxy)-4-bromobenzamide in 1,2-dimethoxy-ethan (10 ml) and water (1 ml) were added 1-((6-(4-chlorophenyl)spiro[3.5]non-6-en-7-yl)methyl)-4-(4,4,5,5-tetramethyl-1,3,2-dioxaborolan-2-yl)-1,2,3,6-tetrahydropyridine, Pd(dppf)Cl$_2$, and K$_2$CO$_3$, and the mixture was stirred at 80° C. for 12 h. The reaction was cooled to room temperature and diluted with water. The mixture was extracted with ethyl acetate (30 mL×3), dried over anhydrous MgSO$_4$, and concentrated.

The residue was purified by C18 reversed phase preparative HPLC to give (R)—N-((4-(((1,4-dioxan-2-yl)methyl)amino)-3-nitrophenyl) sulfonyl)-2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)benzamide. $^1$H NMR (400 MHz, Methanol-d$_4$) δ 8.68 (d, J=2.3 Hz, 1H), 7.97 (d, J=2.6 Hz, 1H), 7.88 (dd, J=9.3, 2.3 Hz, 1H), 7.63 (d, J=8.2 Hz, 1H), 7.50 (d, J=2.6 Hz, 1H), 7.46 (d, J=3.5 Hz, 1H), 7.30 (d, J=8.4 Hz, 2H), 7.16 (dd, J=8.2, 1.7 Hz, 1H), 7.10 (d, J=8.4 Hz, 2H), 6.94 (d, J=9.3 Hz, 1H), 6.85 (d, J=1.7 Hz, 1H), 6.41 (d, J=3.5 Hz, 1H), 5.94-5.90 (m, 1H), 3.95-3.40 (m, 14H), 3.15-3.03 (m, 1H), 2.68-2.45 (m, 2H), 2.43 (s, 2H), 2.30-2.20 (m, 2H), 2.03-1.77 (m, 8H)

Example 3

2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide

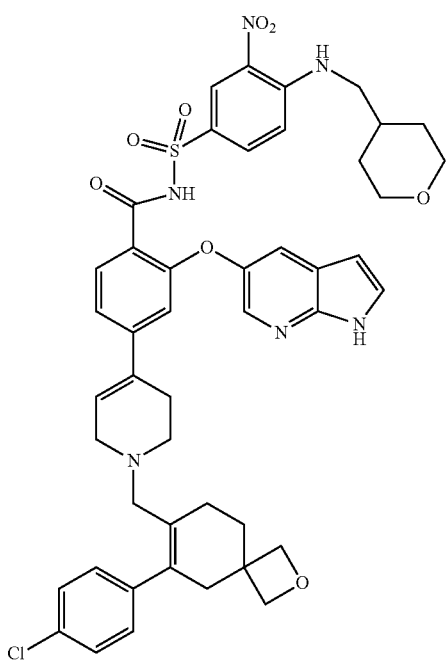 [SMILES: O=C(NS(=O)(=O)c1ccc(NCC2CCOCC2)c([N+](=O)[O-])c1)c1ccc(C2=CCN(CC3=C(c4ccc(Cl)cc4)CC4(CC3)COC4)CC2)cc1Oc1cnc2[nH]ccc2c1]

The title compound was prepared using a procedure similar to the one described for EXAMPLE 2. $^1$H NMR (400 MHz, Methanol-d$_4$) δ 8.70 (d, J=2.3 Hz, 1H), 7.99 (d, J=2.5 Hz, 1H), 7.90 (dd, J=9.2, 2.3 Hz, 1H), 7.61 (d, J=8.2 Hz, 1H), 7.57 (d, J=2.5 Hz, 1H), 7.48 (d, J=3.5 Hz, 1H), 7.31 (d, J=8.4 Hz, 2H), 7.20-7.10 (m, 3H), 6.96 (d, J=9.2 Hz, 1H), 6.82 (d, J=1.6 Hz, 1H), 6.44 (d, J=3.5 Hz, 1H), 5.93-5.86 (m, 1H), 4.53 (d, J=5.9 Hz, 2H), 4.49 (d, J=5.9 Hz, 2H), 4.00-3.90 (m, 2H), 3.77-3.33 (m, 7H), 3.26 (d, J=7.0 Hz, 2H), 3.15-3.00 (m, 1H), 2.70-2.65 (m, 2H), 2.63-2.25 (m, 4H), 2.07 (t, J=6.3 Hz, 2H), 2.00-1.85 (m, 1H), 1.75-1.65 (m, 2H), 1.46-1.30 (m, 2H).

Example 4

Synthesis of 2-((1H-pyrrolo[2,3-b]pyridin-5-yl)oxy)-4-(1-((6-(4-chlorophenyl)spiro[3.5]non-6-en-7-yl)methyl)-1,2,3,6-tetrahydropyridin-4-yl)-N-((3-nitro-4-(((tetrahydro-2H-pyran-4-yl)methyl)amino)phenyl)sulfonyl)benzamide

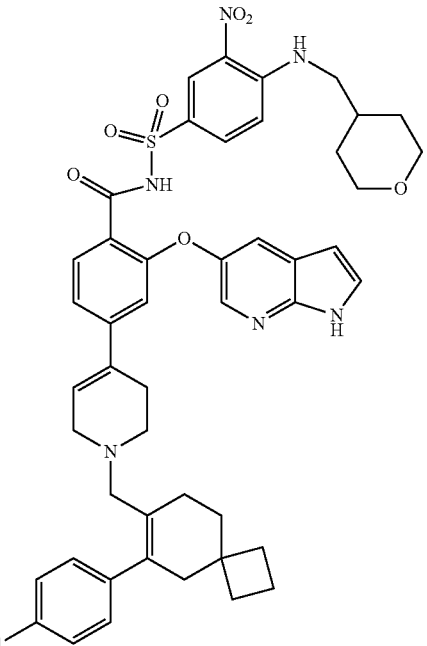

The title compound was prepared using a procedure similar to the one described for EXAMPLE 2. $^1$H NMR (400 MHz, Methanol-d$_4$) δ 8.71 (t, J=1.9 Hz, 1H), 8.00-7.95 (m, 1H), 7.90 (dd, J=9.3, 1.9 Hz, 1H), 7.63 (dd, J=8.1, 1.4 Hz, 1H), 7.56-7.50 (m, 1H), 7.46 (dd, J=3.5, 1.4 Hz, 1H), 7.33-7.26 (m, 2H), 7.18-7.06 (m, 3H), 6.96 (dd, J=9.3, 1.4 Hz, 1H), 6.81 (s, 1H), 6.43 (dd, J=3.5, 1.5 Hz, 1H), 5.93-5.86 (m, 1H), 4.00-3.94 (m, 2H), 3.83-3.36 (m, 7H), 3.26 (d, J=7.0 Hz, 2H), 3.10-3.04 (m, 1H), 2.67-2.40 (m, 4H), 2.30-2.24 (m, 2H), 2.02-1.77 (m, 9H), 1.74-1.67 (m, 2H), 1.45-1.30 (m, 2H).

Example 5

Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(1-((6-(4-chlorophenyl)-2-oxaspiro[3.5]non-6-en-7-yl)methyl)-1,2,3,6-tetrahydropyridin-4-yl)benzamide

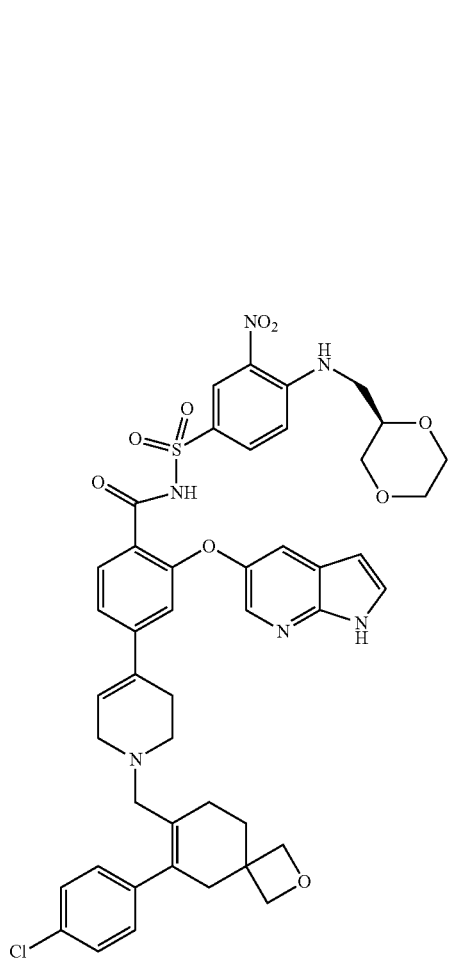 [SMILES: O=C(NS(=O)(=O)c1ccc(NC[C@@H]2COCCO2)c([N+](=O)[O-])c1)c1ccc(C2=CCN(CC3=C(c4ccc(Cl)cc4)CC4(CC3)COC4)CC2)cc1Oc1cnc2[nH]ccc2c1]

The title compound was prepared using a procedure similar to the one described for EXAMPLE 1. $^1$H NMR (400 MHz, Methanol-$d_4$) δ 8.68 (d, J=2.3 Hz, 1H), 7.99 (d, J=2.5 Hz, 1H), 7.89 (dd, J=9.2, 2.3 Hz, 1H), 7.65 (d, J=8.2 Hz, 1H), 7.54 (d, J=2.5 Hz, 1H), 7.48 (d, J=3.4 Hz, 1H), 7.33 (d, J=8.4 Hz, 2H), 7.21-7.16 (m, 1H), 7.13 (d, J=8.4 Hz, 2H), 6.95 (d, J=9.3 Hz, 1H), 6.86 (d, J=1.6 Hz, 1H), 6.43 (d, J=3.5 Hz, 1H), 5.94-5.90 (m, 1H), 4.60-4.43 (m, 4H), 3.95-3.40 (m, 14H), 3.15-3.00 (m, 1H), 2.80-2.60 (m, 4H), 2.38-2.25 (m, 2H), 2.08 (t, J=6.3 Hz, 2H).

Example 6

Synthesis of (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide

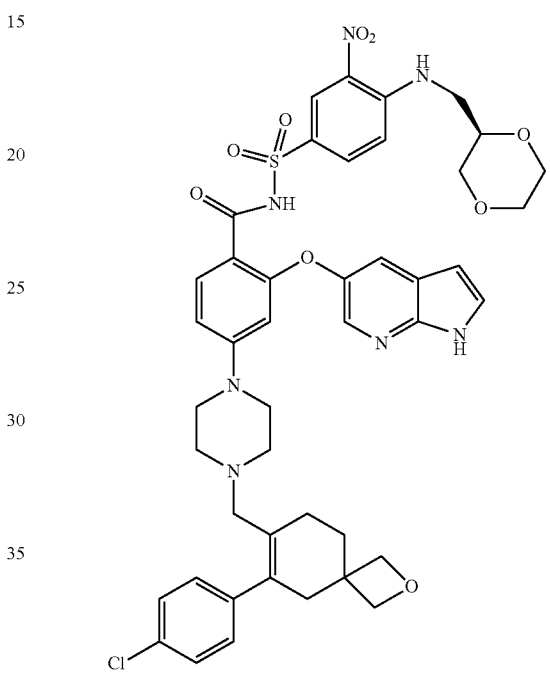

A mixture of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (290 mg, 0.5 mmol), (R)-4-(((1,4-dioxan-2-yl)methyl)amino)-3-nitrobenzenesulfonamide (236 mg, 0.75 mmol), EDCI (191 mg, 1 mmol), 4-(N,N-dimethylamino)pyridine (591 mg, 0.75 mmol) in dichloromethane (15 ml) was stirred at room temperature overnight. The solvent was removed under vacuum and the resulting residue was purified through a silica gel column to afford (R)—N-((4-(((1,4-dioxan-2-yl)methyl)amino)-3-nitrophenyl)sulfonyl)-2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzamide (150 mg, 34.1%) as yellow solid. $^1$H NMR (400 MHz, Methanol-$d_4$) δ 8.67 (d, J=2.3 Hz, 1H), 7.99 (d, J=2.3 Hz, 1H), 7.85 (dd, J=9.3, 2.3 Hz, 1H), 7.64 (d, J=8.8 Hz, 1H), 7.52 (d, J=2.3 Hz, 1H), 7.45 (d, J=3.5 Hz, 1H), 7.39 (d, J=8.4 Hz, 2H), 7.13 (d, J=8.4 Hz, 2H), 6.95 (d, J=9.3 Hz, 1H), 6.76 (dd, J=8.8, 2.4 Hz, 1H), 6.41 (d, J=3.5 Hz, 1H), 6.34 (d, J=2.4 Hz, 1H), 4.54 (d, J=5.9 Hz, 2H), 4.48 (d, J=5.9 Hz, 2H), 3.93-3.35 (m, 19H), 2.70-2.65 (m, 2H), 2.33 (s, 2H), 2.08 (t, J=6.3 Hz, 2H).

Example 7

Synthesis of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)-N-((3-nitro-4-(((tetrahydro-2H-pyran-4-yl)methyl)amino)phenyl)sulfonyl)benzamide

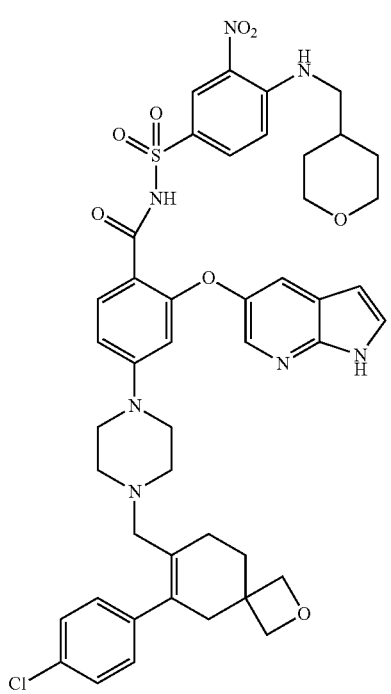 [SMILES: O=C(NS(=O)(=O)c1ccc(NCC2CCOCC2)c([N+](=O)[O-])c1)c1ccc(N2CCN(CC3=C(c4ccc(Cl)cc4)CC4(CC3)COC4)CC2)cc1Oc1cnc2[nH]ccc2c1]

A mixture of 2-((1H-pyrrolo[2,3-b]pyridin-5-yl)oxy)-4-(4-((6-(4-chlorophenyl)-2-oxaspiro[3.5]non-6-en-7-yl)methyl)piperazin-1-yl)benzoic acid (250 mg, 0.43 mmol), 3-nitro-4-(((tetrahydro-2H-pyran-4-yl)methyl)amino)benzenesulfonamide (202 mg, 0.64 mmol), EDCI (164 mg, 0.86 mmol), 4-(N,N-dimethylamino)pyridine (78 mg, 0.64 mmol) in dichloromethane (10 ml) was stirred at room temperature for overnight, followed by concentration. The resulting residue was purified through silica gel column to afford 2-((1H-pyrrolo[2,3-b]pyridin-5-yl)oxy)-4-(4-((6-(4-chlorophenyl)-2-oxaspiro[3.5]non-6-en-7-yl)methyl) piperazin-1-yl)-N-((3-nitro-4-(((tetrahydro-2H-pyran-4-yl)methyl)amino)phenyl) sulfonyl) benzamide (150 mg, 39.6%) as yellow solid. $^1$H NMR (400 MHz, Methanol-$d_4$) δ 8.70 (d, J=2.3 Hz, 1H), 8.01 (d, J=2.6 Hz, 1H), 7.87 (dd, J=9.2, 2.3 Hz, 1H), 7.66 (d, J=8.8 Hz, 1H), 7.56 (d, J=2.6 Hz, 1H), 7.47 (d, J=3.5 Hz, 1H), 7.39 (d, J=8.4 Hz, 2H), 7.13 (d, J=8.4 Hz, 2H), 6.97 (d, J=9.2 Hz, 1H), 6.76 (dd, J=8.8, 2.4 Hz, 1H), 6.43 (d, J=3.5 Hz, 1H), 6.32 (d, J=2.4 Hz, 1H), 4.54 (d, J=5.9 Hz, 2H), 4.48 (d, J=5.9 Hz, 2H), 4.03-3.94 (m, 2H), 3.67 (s, 2H), 3.55-3.27 (m, 12H), 2.69 (s, 2H), 2.35-2.25 (m, 2H), 2.08 (t, J=6.3 Hz, 2H), 2.05-1.93 (m, 1H), 1.76-1.69 (m, 2H), 1.45-1.35 (m, 2H).

Example 8

Synthesis of 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide

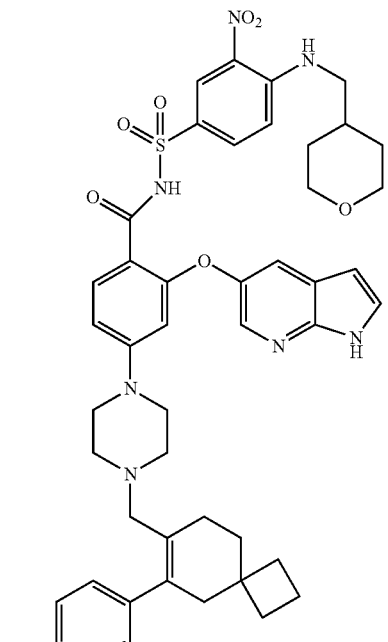

A mixture of 2-((1H-pyrrolo[2,3-b]pyridin-5-yl)oxy)-4-(4-((6-(4-chlorophenyl)spiro[3.5]non-6-en-7-yl)methyl)piperazin-1-yl)benzoic acid (1.75 g, 3 mmol), 3-nitro-4-(((tetrahydro-2H-pyran-4-yl)methyl)amino)benzene sulfonamide (1.43 g, 4.5 mmol), EDCI (1.15 g, 6 mmol) and 4-(N,N-dimethylamino)pyridine (550 mg, 4.5 mmol) and dichloromethane (40 ml) was reacted at room temperature for overnight, followed by adding water. The water layer was extracted with dichloromethane. The combined organic layers were washed with brine, concentrated and purified through silica gel column to afford 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((3-nitro-4-(((tetrahydro-2H-pyran-4-yl)methyl)amino)phenyl)sulfonyl)benzamide (1.7 g, 64.4%) as yellow solid. $^1$H NMR (400 MHz, Methanol-$d_4$) δ 8.70 (d, J=2.3 Hz, 1H), 8.01 (d, J=2.7 Hz, 1H), 7.87 (d, J=9.2, 2.3 Hz, 1H), 7.66 (d, J=8.9 Hz, 1H), 7.55 (d, J=2.7 Hz, 1H), 7.47 (d, J=3.4 Hz, 1H), 7.38 (d, J=8.4 Hz, 2H), 7.10 (d, J=8.4 Hz, 2H), 6.97 (d, J=9.2 Hz, 1H), 6.77 (dd, J=8.9, 2.4 Hz, 1H), 6.44 (d, J=3.4 Hz, 1H), 6.34 (d, J=2.4 Hz, 1H), 4.02-3.94 (m, 3H), 3.66 (s, 3H), 3.49-3.38 (m, 2H), 3.41-3.25 (m, 7H), 2.42 (s, 3H), 2.26 (s, 3H), 2.00-1.67 (m, 4H), 1.45-1.38 (m, 2H).

Example 9

Synthesis of (R)—N-((4-(((1,4-dioxan-2-yl)methyl)amino)-3-nitrophenyl) sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

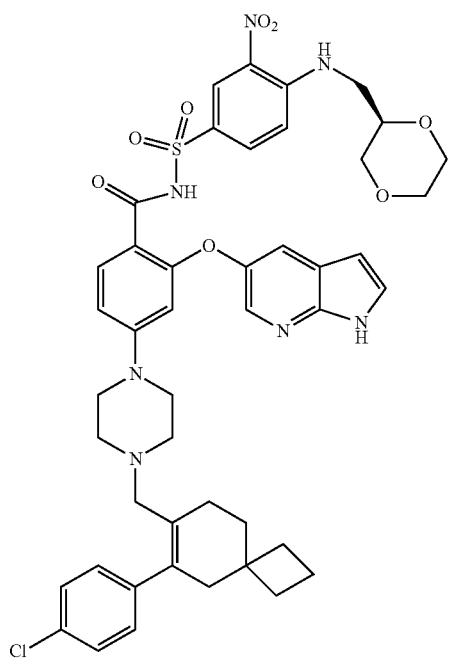 [SMILES: O=C(NS(=O)(=O)c1ccc(NC[C@@H]2COCCO2)c([N+](=O)[O-])c1)c1ccc(N2CCN(CC3=C(c4ccc(Cl)cc4)CC4(CCC4)CC3)CC2)cc1Oc1cnc2[nH]ccc2c1]

The title compound was prepared using a procedure similar to the one described for EXAMPLE 8. $^1$H NMR (400 MHz, Methanol-$d_4$) δ 8.66 (d, J=2.4 Hz, 1H), 7.99 (d, J=2.4 Hz, 1H), 7.84 (dd, J=9.2, 2.4 Hz, 1H), 7.64 (d, J=8.9 Hz, 1H), 7.51 (d, J=2.4 Hz, 2H), 7.45 (d, J=3.3 Hz, 1H), 7.37 (d, J=8.4 Hz, 2H), 7.10 (d, J=8.4 Hz, 2H), 6.94 (d, J=9.2 Hz, 1H), 6.76 (dd, J=8.9, 2.3 Hz, 1H), 6.40 (d, J=3.3 Hz, 1H), 6.36 (d, J=2.3 Hz, 1H), 3.87 (dd, J=11.8, 4.2 Hz, 3H), 3.83-3.70 (m, 3H), 3.67 (s, 2H), 3.62 (dd, J=11.7, 2.9 Hz, 1H), 3.51-3.41 (m, 2H), 3.40-3.35 (m, 1H), 3.29 (dq, J=3.2, 1.6 Hz, 1H), 2.41 (s, 2H), 2.26 (s, 2H), 2.00-1.77 (m, 6H).

Example 10

Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((3-nitrophenyl)sulfonyl)benzamide

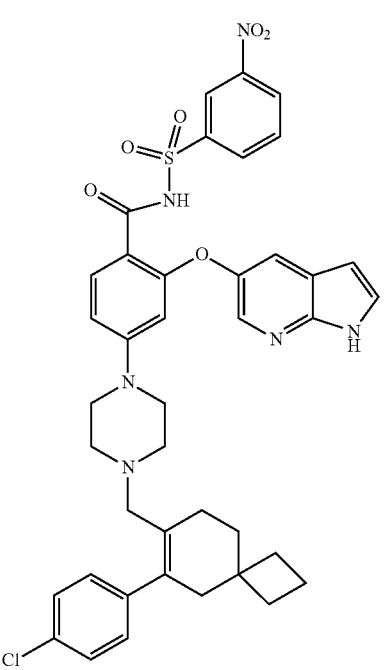 [SMILES: O=C(NS(=O)(=O)c1cccc([N+](=O)[O-])c1)c1ccc(N2CCN(CC3=C(c4ccc(Cl)cc4)CC4(CCC4)CC3)CC2)cc1Oc1cnc2[nH]ccc2c1]

The title compound was prepared using a procedure similar to the one described for EXAMPLE 8. $^1$H NMR (400 MHz, DMSO-$d_6$) δ 11.70 (s, 1H), 9.47 (s, 1H), 8.62 (d, J=2.2 Hz, 1H), 8.44 (d, J=8.3 Hz, 1H), 8.27 (d, J=7.9 Hz, 1H), 8.02-7.97 (m, 1H), 7.84-7.75 (m, 1H), 7.56-7.43 (m, 3H), 7.40 (d, J=8.3 Hz, 2H), 7.11 (d, J=8.3 Hz, 2H), 6.72 (d, J=8.9 Hz, 1H), 6.40-6.35 (m, 1H), 6.30 (s, 1H), 3.80-3.65 (m, 2H), 3.55 (s, 2H), 3.28-2.95 (m, 4H), 2.82-2.65 (m, 2H), 2.31 (s, 2H), 2.22-2.15 (m, 2H), 1.93-1.60 (m, 8H).

Example 11

Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((4-(methylamino)-3-nitrophenyl) sulfonyl)benzamide

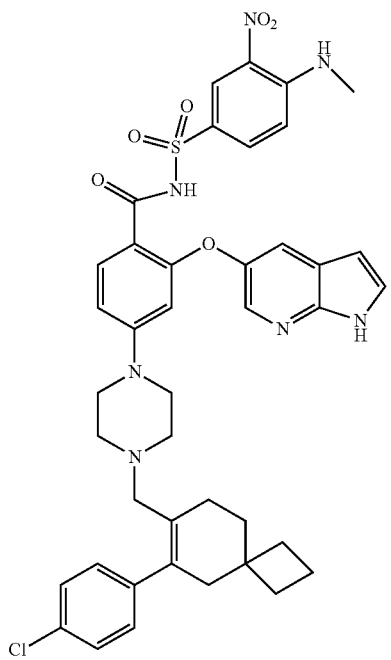 [SMILES: CNc1ccc(S(=O)(=O)NC(=O)c2ccc(N3CCN(CC4=C(c5ccc(Cl)cc5)CC5(CCC5)CC4)CC3)cc2Oc2cnc3[nH]ccc3c2)cc1[N+](=O)[O-]]

The title compound was prepared using a procedure similar to the one described for EXAMPLE 8. $^1$H NMR (400 MHz, Methanol-$d_4$) δ 8.78 (d, J=2.3 Hz, 1H), 8.05 (d, J=2.6 Hz, 1H), 7.96 (dd, J=9.2, 2.3 Hz, 1H), 7.80 (d, J=8.9 Hz, 1H), 7.61 (d, J=2.6 Hz, 1H), 7.46 (d, J=3.5 Hz, 1H), 7.34 (d, J=8.4 Hz, 2H), 7.01 (d, J=8.4 Hz, 2H), 6.90 (d, J=9.2 Hz, 1H), 6.68 (dd, J=8.9, 2.4 Hz, 1H), 6.46 (d, J=3.5 Hz, 1H), 6.18 (d, J=2.4 Hz, 1H), 3.60 (s, 2H), 3.50-3.12 (m, 8H), 3.06 (s, 3H), 2.38 (s, 2H), 2.30-2.16 (m, 2H), 1.97-1.73 (m, 8H).

Example 12

Synthesis of 2-((1H-pyrrolo[2,3-b]pyridin-5-yl)oxy)-4-(4-((6-(4-chlorophenyl) spiro[3.5]non-6-en-7-yl)methyl)piperazin-1-yl)-N-((4-(dimethylamino)-3-nitrophenyl) sulfonyl)benzamide

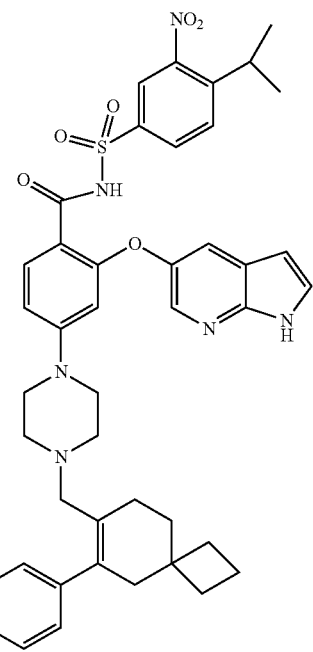

The title compound was prepared using a procedure similar to the one described for EXAMPLE 8. $^1$H NMR (400 MHz, Methanol-$d_4$) δ 8.41 (d, J=2.2 Hz, 1H), 8.08 (d, J=2.5 Hz, 1H), 7.91 (dd, J=9.4, 2.3 Hz, 1H), 7.81 (d, J=8.9 Hz, 1H), 7.68 (d, J=2.3 Hz, 1H), 7.48 (d, J=3.5 Hz, 1H), 7.34 (d, J=8.0 Hz, 2H), 7.04 (d, J=9.4 Hz, 1H), 7.01 (d, J=8.0 Hz, 2H), 6.71-6.63 (m, 1H), 6.51 (d, J=3.5 Hz, 1H), 6.15 (d, J=1.9 Hz, 1H), 3.59 (s, 2H), 3.52-3.20 (m, 8H), 2.98 (s, 6H), 2.38 (s, 2H), 2.25-2.17 (m, 2H), 1.96-1.72 (m, 8H).

Example 13

Synthesis of 2-((1H-pyrrolo[2,3-b]pyridin-5-yl)oxy)-4-(1-((6-(4-chlorophenyl) spiro[3.5]non-6-en-7-yl)methyl)piperidin-4-yl)-N-((3-nitro-4-((((tetrahydro-2H-pyran-4-yl)methyl)amino)phenyl)sulfonyl)benzamide

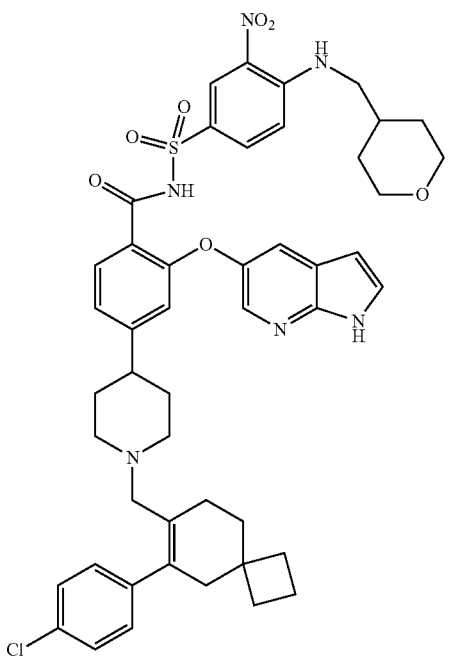 [SMILES: O=C(NS(=O)(=O)c1ccc(NCC2CCOCC2)c([N+](=O)[O-])c1)c1ccc(C2CCN(CC3=C(c4ccc(Cl)cc4)CC4(CCC4)CC3)CC2)cc1Oc1cnc2[nH]ccc2c1]

A mixture of 2-((1H-pyrrolo[2,3-b]pyridin-5-yl)oxy)-4-(1-((6-(4-chlorophenyl)spiro[3.5]non-6-en-7-yl)methyl)piperidin-4-yl)benzoic acid (200 mg, 0.34 mmol), 3-nitro-4-(((tetrahydro-2H-pyran-4-yl)methyl)amino)benzenesulfonamide (162 mg, 0.52 mmol), EDCI (130 mg, 0.68 mmol), 4-(N,N-dimethylamino)pyridine (63.4 mg, 0.52 mmol) in dichloromethane (15 ml) was stirred at room temperature for overnight, followed by purification by silica gel column chromatography to afford 2-((1H-pyrrolo[2,3-b]pyridin-5-yl)oxy)-4-(1-((6-(4-chlorophenyl)spiro[3.5]non-6-en-7-yl)methyl)piperidin-4-yl)-N-((3-nitro-4-(((tetrahydro-2H-pyran-4-yl)methyl)amino)phenyl)sulfonyl)benzamide (170 mg, 57.3%) as yellow solid. $^1$H NMR (400 MHz, DMSO-d$_6$) δ 11.94 (s, 1H), 11.64 (s, 1H), 8.50-8.42 (m, 2H), 7.97 (d, J=2.6 Hz, 1H), 7.76 (dd, J=9.2, 2.2 Hz, 1H), 7.52-7.36 (m, 5H), 7.11 (d, J=7.9 Hz, 2H), 6.99 (d, J=9.2 Hz, 1H), 6.91-6.86 (m, 1H), 6.55 (s, 1H), 6.37 (s, 1H), 3.89-3.79 (m, 2H), 3.35-2.90 (m, 10H), 2.32-2.10 (m, 5H), 1.95-1.15 (m, 17H).

Example 14

The following Compounds of the Disclosure were prepared using the methodologies described in Examples 1-13:

Cpd. No. 40: (S)—N-((4-(((1,4-dioxan-2-yl)methyl)amino)-3-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

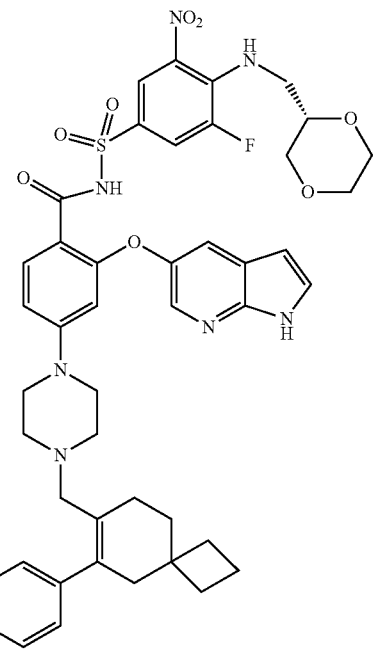

$^1$H NMR (400 MHz, methanol-d$_4$) δ 8.49-8.46 (m, 1H), 7.99 (d, J=2.6 Hz, 1H), 7.70 (dd, J=13.6, 2.3 Hz, 1H), 7.66 (d, J=8.8 Hz, 1H), 7.49 (d, J=2.6 Hz, 1H), 7.45 (d, J=3.4 Hz, 1H), 7.38 (d, J=8.5 Hz, 2H), 7.10 (d, J=8.5 Hz, 2H), 6.79 (dd, J=8.8, 2.3 Hz, 1H), 6.41-6.37 (m, 2H), 3.83-2.70 (m, 19H), 2.42 (s, 2H), 2.30-2.22 (m, 2H), 2.00-1.78 (m, 8H).

Cpd. No. 44: (S)—N-((4-(((1,4-dioxan-2-yl)methyl)amino)-2-fluoro-5-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

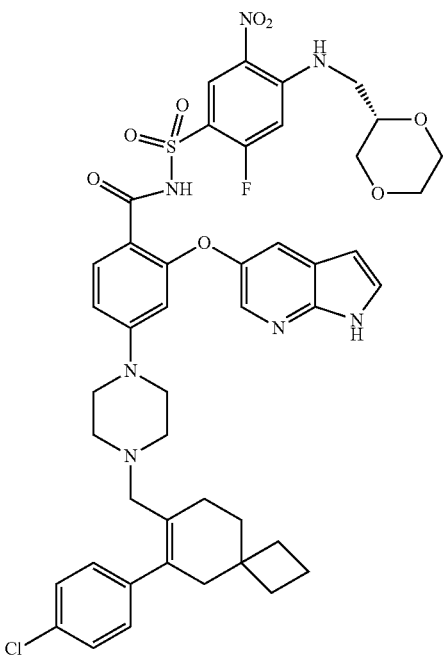 [SMILES: O=C(NS(=O)(=O)c1cc([N+](=O)[O-])c(NC[C@H]2COCCO2)cc1F)c1ccc(N2CCN(CC3=C(c4ccc(Cl)cc4)CC4(CCC4)CC3)CC2)cc1Oc1cnc2[nH]ccc2c1]

¹H NMR (400 MHz, methanol-d₄) δ 8.75 (d, J=7.5 Hz, 1H), 8.08-8.02 (m, 1H), 7.68 (d, J=2.4 Hz, 1H), 7.63 (d, J=8.8 Hz, 1H), 7.50 (d, J=3.4 Hz, 1H), 7.36 (d, J=8.4 Hz, 2H), 7.09 (d, J=8.4 Hz, 2H), 6.80-6.72 (m, 2H), 6.50 (d, J=3.4 Hz, 1H), 6.29 (d, J=2.2 Hz, 1H), 3.90-2.70 (m, 19H), 2.41 (s, 2H), 2.32-2.20 (m, 2H), 2.00-1.78 (m, 8H).

Cpd. No. 45: (S)—N-((4-(((1,4-dioxan-2-yl)methyl)amino)-2-fluoro-3-nitrophenyl)sulfonyl)-2-((1H-pyrrolo[2,3-b]pyridin-5-yl)oxy)-4-(4-((6-(4-chlorophenyl)spiro[3.5]non-6-en-7-yl)methyl)piperazin-1-yl)benzamide

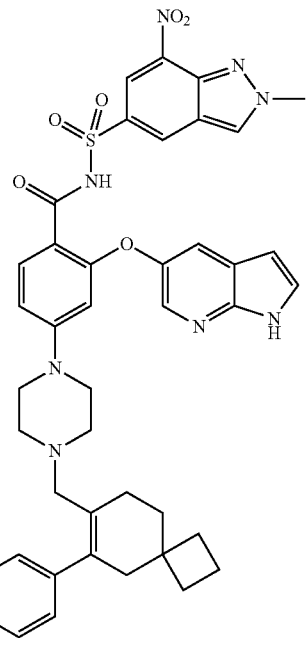

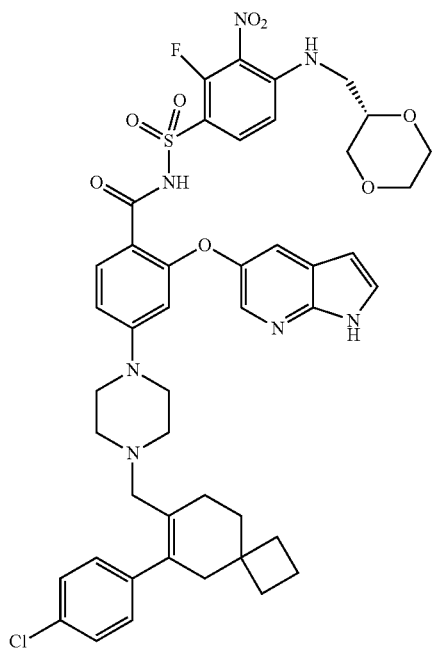 [SMILES: O=C(NS(=O)(=O)c1ccc(NC[C@H]2COCCO2)c([N+](=O)[O-])c1F)c1ccc(N2CCN(CC3=C(c4ccc(Cl)cc4)CC4(CCC4)CC3)CC2)cc1Oc1cnc2[nH]ccc2c1]

MS m/z=900 [M+H].

Cpd. No. 46: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-methyl-7-nitro-2H-indazol-5-yl)sulfonyl)benzamide ¹H NMR (400 MHz, methanol-d₄) δ 8.80 (d, J=1.6 Hz, 1H), 8.73 (d, J=1.6 Hz, 1H), 8.69 (s, 1H), 7.92 (d, J=2.5 Hz, 1H), 7.62 (d, J=8.9 Hz, 1H), 7.44 (d, J=2.6 Hz, 1H), 7.39 (d, J=3.4 Hz, 1H), 7.36 (d, J=8.5 Hz, 2H), 7.09 (d, J=8.5 Hz, 2H), 6.75 (dd, J=8.9, 2.3 Hz, 1H), 6.34 (d, J=2.3 Hz, 1H), 6.32 (d, J=3.4 Hz, 1H), 4.35 (s, 3H), 3.3.67-2.70 (m, 8H), 3.66 (s, 2H), 2.41 (s, 2H), 2.32-2.22 (m, 2H), 2.02-1.75 (m, 8H).

Cpd. No. 47: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-1H-benzo[d]imidazol-5-yl) sulfonyl)benzamide

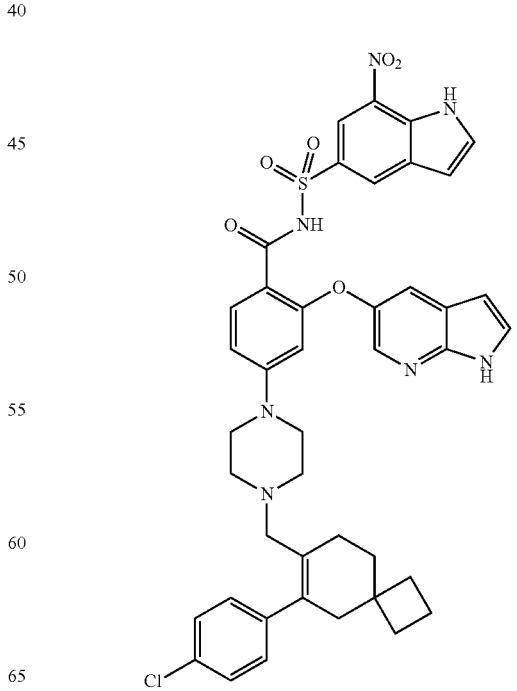

¹H NMR (400 MHz, methanol-d₄) δ 8.70 (d, J=1.3 Hz, 1H), 8.64 (d, J=1.3 Hz, 1H), 8.57 (s, 1H), 7.93 (d, J=1.9 Hz, 1H), 7.59 (d, J=8.9 Hz, 1H), 7.50 (d, J=2.5 Hz, 1H), 7.40 (d, J=3.4 Hz, 1H), 7.33 (d, J=8.4 Hz, 2H), 7.08 (d, J=8.4 Hz, 2H), 6.74 (dd, J=8.9, 2.2 Hz, 1H), 6.35 (d, J=2.2 Hz, 1H), 6.33 (d, J=3.4 Hz, 1H), 3.72-2.72 (m, 8H), 2.40 (s, 2H), 2.34-2.20 (m, 2H), 2.00-1.77 (m, 8H).

Cpd. No. 48: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-(tetrahydro-2H-pyran-4-yl)-2H-indazol-5-yl)sulfonyl)benzamide

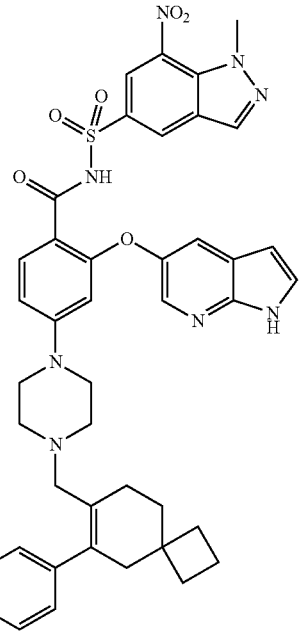

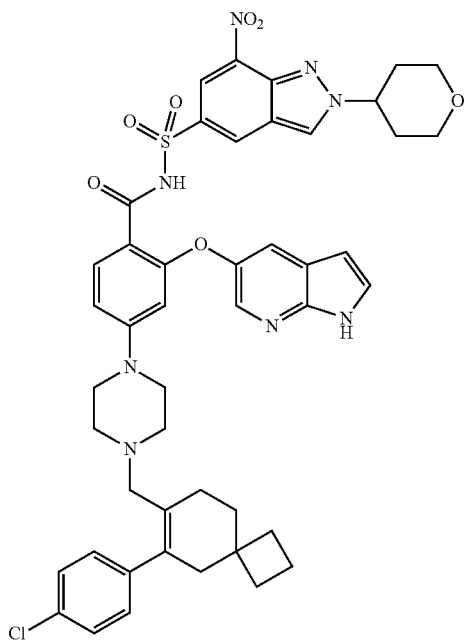 [SMILES: O=C(NS(=O)(=O)c1cc([N+](=O)[O-])c2nn(C3CCOCC3)cc2c1)c1ccc(N2CCN(CC3=C(c4ccc(Cl)cc4)CC4(CCC4)CC3)CC2)cc1Oc1cnc2[nH]ccc2c1]

¹H NMR (400 MHz, methanol-d₄) δ 8.87 (d, J=1.6 Hz, 1H), 8.84 (s, 1H), 8.75 (d, J=1.6 Hz, 1H), 7.96 (d, J=2.6 Hz, 1H), 7.64 (d, J=8.9 Hz, 1H), 7.50 (d, J=2.6 Hz, 1H), 7.41 (d, J=3.4 Hz, 1H), 7.38 (d, J=8.5 Hz, 2H), 7.09 (d, J=8.5 Hz, 2H), 6.75 (dd, J=8.9, 2.3 Hz, 1H), 6.35 (d, J=3.4 Hz, 1H), 6.31 (d, J=2.3 Hz, 1H). 4.20-4.14 (m, 2H), 3.75-2.70 (m, 13H), 2.41 (s, 2H), 2.32-1.76 (m, 14H).

Cpd. No. 49: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-7-nitro-1H-indazol-5-yl)sulfonyl)benzamide ¹H NMR (400 MHz, methanol-d₄) δ 8.71 (d, J=1.5 Hz, 1H), 8.63 (d, J=1.5 Hz, 1H), 8.33 (s, 1H), 7.95 (d, J=2.4 Hz, 1H), 7.63 (d, J=8.9 Hz, 1H), 7.50 (d, J=2.5 Hz, 1H), 7.42 (d, J=3.4 Hz, 1H), 7.37 (d, J=8.3 Hz, 2H), 7.09 (d, J=8.3 Hz, 2H), 6.76 (dd, J=8.9, 1.7 Hz, 1H), 6.36 (d, J=3.4 Hz, 1H), 6.34 (d, J=1.7 Hz, 1H), 4.20 (s, 3H), 3.75-2.70 (m, 8H), 3.70 (s, 2H), 2.41 (s, 2H), 2.30-2.23 (m, 2H), 2.00-1.76 (m, 8H).

Cpd. No. 50: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2H-indazol-5-yl)sulfonyl)benzamide

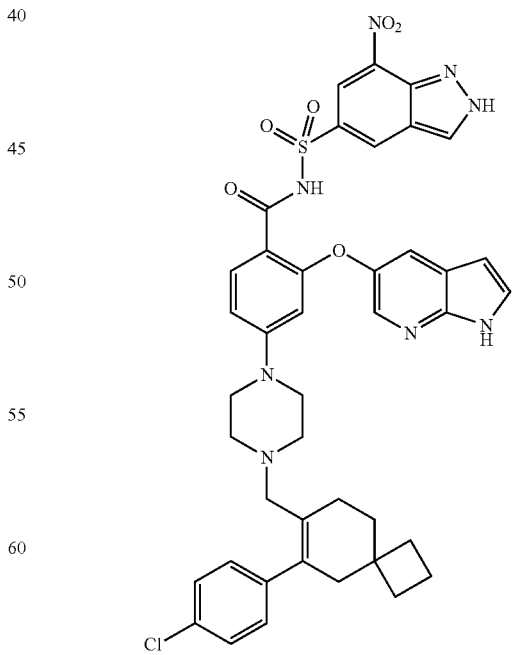

¹H NMR (400 MHz, methanol-d₄) δ 8.82 (s, 2H), 8.41 (s, 1H), 7.93 (d, J=2.5 Hz, 1H), 7.64 (d, J=9.0 Hz, 1H), 7.44 (d, J=2.5 Hz, 1H), 7.40-7.34 (m, 3H), 7.09 (d, J=8.4 Hz, 2H), 6.76 (dd, J=9.0, 2.3 Hz, 1H), 6.36 (d, J=2.3 Hz, 1H), 6.29 (d, J=3.4 Hz, 1H), 3.70-2.70 (m, 8H), 3.66 (s, 2H), 2.41 (s, 2H), 2.30-2.20 (m, 2H), 2.02-1.77 (m, 8H).

Cpd. No. 51: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((4-nitro-2H-indazol-6-yl)sulfonyl)benzamide

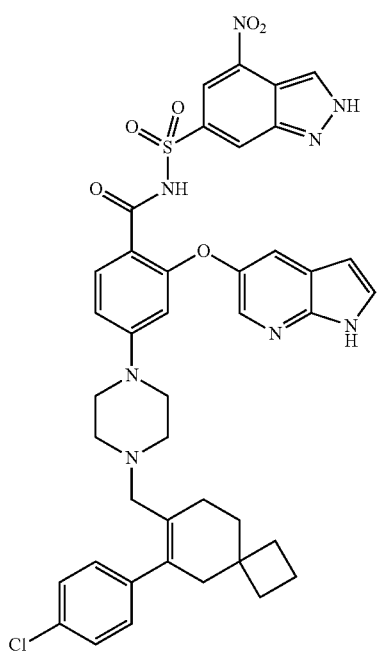 [SMILES: O=C(NS(=O)(=O)c1cc([N+](=O)[O-])c2c[nH]nc2c1)c1ccc(N2CCN(CC3=C(c4ccc(Cl)cc4)CC4(CCC4)CC3)CC2)cc1Oc1cnc2[nH]ccc2c1]

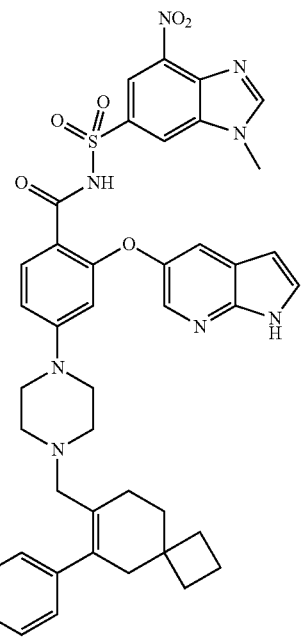

¹H NMR (400 MHz, methanol-d₄) δ 8.66 (d, J=1.6 Hz, 1H), 8.60 (s, 1H), 8.54 (d, J=1.6 Hz, 1H), 7.91 (d, J=2.6 Hz, 1H), 7.64 (d, J=8.9 Hz, 1H), 7.38 (d, J=8.5 Hz, 2H), 7.35 (d, J=2.6 Hz, 1H), 7.33 (d, J=3.5 Hz, 1H), 7.10 (d, J=8.5 Hz, 2H), 6.77 (dd, J=8.9, 2.3 Hz, 1H), 6.37 (d, J=2.3 Hz, 1H), 6.27 (d, J=3.5 Hz, 1H), 4.01 (s, 3H), 3.70-2.70 (m, 8H), 3.66 (s, 2H), 2.42 (s, 2H), 2.32-2.23 (m, 2H), 2.03-1.80 (m, 8H).

Cpd. No. 53: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((7-nitro-2-((tetrahydro-2H-pyran-4-yl)methyl)-1H-benzo[d]imidazol-5-yl)sulfonyl)benzamide

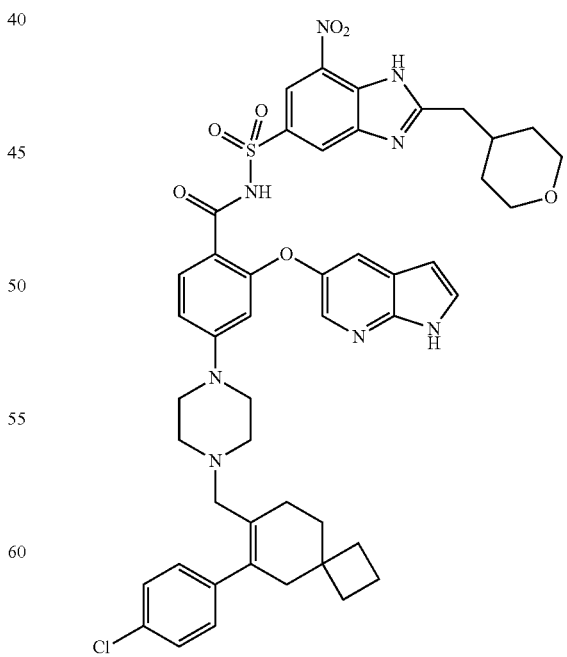

¹H NMR (400 MHz, methanol-d₄) δ 9.19 (s, 1H), 8.84 (s, 1H), 8.73 (d, J=1.2 Hz, 1H), 7.94 (d, J=2.5 Hz, 1H), 7.65 (d, J=2.5 Hz, 1H), 7.63 (d, J=8.7 Hz, 1H), 7.43-7.37 (m, 3H), 7.12 (d, J=8.4 Hz, 2H), 6.81 (dd, J=8.7, 2.1 Hz, 1H), 6.41 (d, J=3.4 Hz, 1H), 6.39 (d, J=2.1 Hz, 1H), 3.71-2.70 (m, 8H), 3.69 (s, 2H), 2.43 (s, 2H), 2.30-2.24 (m, 2H), 2.02-1.76 (m, 8H).

Cpd. No. 52: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((1-methyl-4-nitro-1H-benzo[d]imidazol-6-yl)sulfonyl)benzamide ¹H NMR (400 MHz, methanol-d₄) δ 8.67 (d, J=1.5 Hz, 1H), 8.56 (d, J=1.5 Hz, 1H), 7.94 (d, J=2.5 Hz, 1H), 7.63 (d, J=8.9 Hz, 1H), 7.48 (d, J=2.5 Hz, 1H), 7.41 (d, J=3.4 Hz, 1H), 7.36 (d, J=8.5 Hz, 2H), 7.09 (d, J=8.5 Hz, 2H), 6.74 (dd, J=8.9, 2.3 Hz, 1H), 6.34 (d, J=3.4 Hz, 1H), 6.30 (d, J=2.3 Hz, 1H), 4.00-3.85 (m, 2H), 3.70-2.70 (m, 10H), 3.65 (s, 2H), 2.98 (d, J=7.3 Hz, 2H), 2.41 (s, 2H), 2.35-2.20 (m, 3H), 2.02-1.40 (m, 12H).

Cpd. No. 54: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-(2-methoxyethoxy)ethyl)-4-nitro-2H-indazol-6-yl)sulfonyl)benzamide

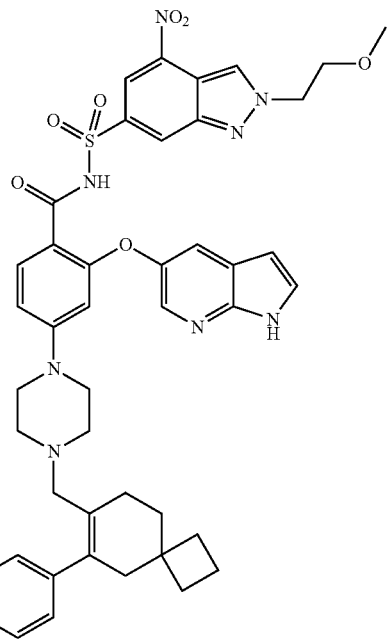

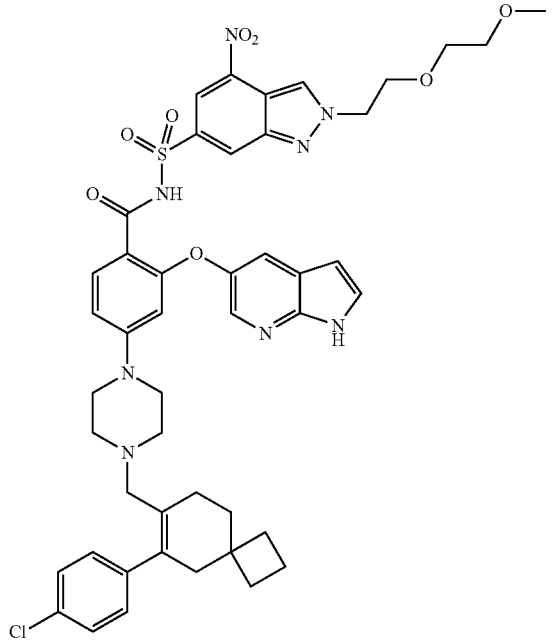 [SMILES: COCCOCCn1cc2c([N+](=O)[O-])cc(S(=O)(=O)NC(=O)c3ccc(N4CCN(CC5=C(c6ccc(Cl)cc6)CC6(CCC6)CC5)CC4)cc3Oc3cnc4[nH]ccc4c3)cc2n1]

¹H NMR (400 MHz, methanol-d₄) δ 8.80 (d, J=0.8 Hz, 1H), 8.74-8.72 (m, 1H), 8.54 (d, J=1.3 Hz, 1H), 7.93 (d, J=2.5 Hz, 1H), 7.65 (d, J=8.9 Hz, 1H), 7.42 (d, J=2.5 Hz, 1H), 7.40-7.35 (m, 3H), 7.10 (d, J=8.5 Hz, 2H), 6.78 (dd, J=8.9, 2.4 Hz, 1H), 6.36 (d, J=2.4 Hz, 1H), 6.30 (d, J=3.4 Hz, 1H), 4.79 (t, J=5.0 Hz, 2H), 3.99 (t, J=5.0 Hz, 2H), 3.70-2.70 (m, 8H), 3.67 (s, 2H), 3.38 (s, 3H), 2.42 (s, 2H), 2.32-2.25 (m, 2H), 2.02-1.76 (m, 8H).

Cpd. No. 25: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((5-nitro-1-((tetrahydro-2H-pyran-4-yl)methyl)-1H-pyrrol-3-yl)sulfonyl)benzamide

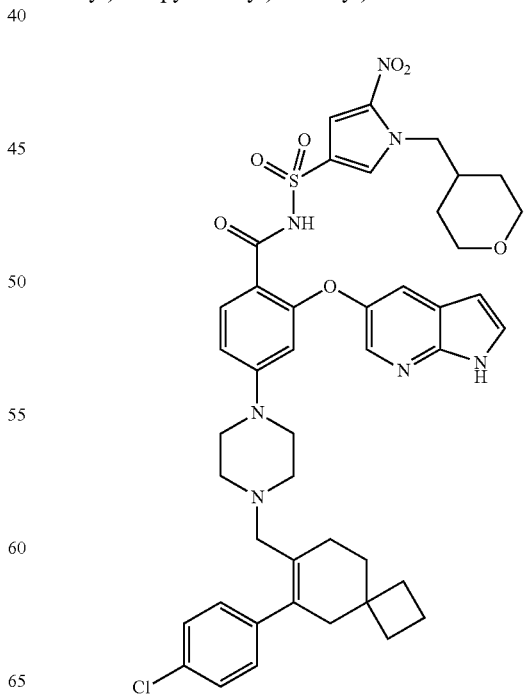

¹H NMR (400 MHz, methanol-d₄) δ 8.85 (s, 1H), 8.70 (s, 1H), 8.53 (d, J=1.2 Hz, 1H), 7.94 (d, J=2.5 Hz, 1H), 7.65 (d, J=8.9 Hz, 1H), 7.43 (d, J=2.5 Hz, 1H), 7.42-7.35 (m, 3H), 7.10 (d, J=8.4 Hz, 2H), 6.79 (dd, J=8.9, 2.3 Hz, 1H), 6.39 (d, J=2.3 Hz, 1H), 6.30 (d, J=3.4 Hz, 1H), 4.80 (t, J=5.0 Hz, 2H), 4.09 (t, J=5.0 Hz, 2H), 3.70-3.65 (m, 4H), 3.64-2.70 (m, 10H), 3.29 (s, 3H), 2.42 (s, 2H), 2.30-2.25 (m, 2H), 2.02-1.76 (m, 8H).

Cpd. No. 55: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-((2-(2-methoxyethyl)-4-nitro-2H-indazol-6-yl)sulfonyl)benzamide $^1$H NMR (400 MHz, methanol-$d_4$) δ 8.04 (d, J=2.5 Hz, 1H), 7.72-7.68 (m, 2H), 7.61 (d, J=2.5 Hz, 1H), 7.48 (d, J=3.5 Hz, 1H), 7.45 (d, J=2.2 Hz, 1H), 7.39 (d, J=8.5 Hz, 2H), 7.11 (d, J=8.5 Hz, 2H), 6.80 (dd, J=8.9, 2.3 Hz, 1H), 6.47 (d, J=3.5 Hz, 1H), 6.37 (d, J=2.3 Hz, 1H), 4.27 (d, J=7.2 Hz, 2H), 3.85-2.70 (m, 12H), 3.66 (s, 2H), 2.42 (s, 2H), 2.35-2.25 (m, 2H), 2.03-1.77 (m, 9H), 1.48-1.26 (m, 4H).

Cpd. No. 56: 2-((1H-pyrrolo[2,3-b]pyridin-5-yl)oxy)-4-(4-((6-(4-chlorophenyl)spiro[3.5]non-6-en-7-yl)methyl)piperazin-1-yl)-N-(naphthalen-2-ylsulfonyl)benzamide

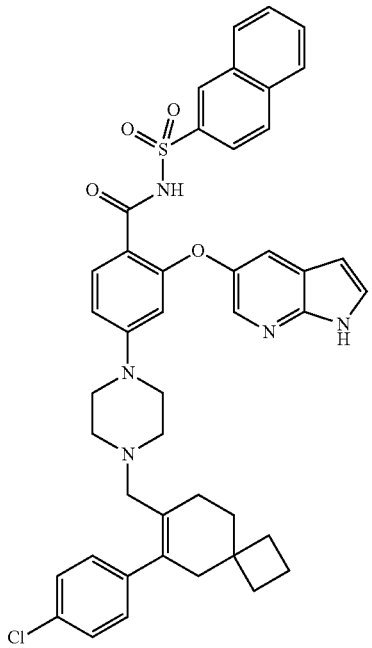 [SMILES: O=C(NS(=O)(=O)c1ccc2ccccc2c1)c1ccc(N2CCN(CC3=C(c4ccc(Cl)cc4)CC4(CCC4)CC3)CC2)cc1Oc1cnc2[nH]ccc2c1]

$^1$H NMR (400 MHz, methanol-$d_4$+CDCl$_3$) δ 8.61 (s, 1H), 8.07 (d, J=2.5 Hz, 1H), 7.92-7.70 (m, 4H), 7.78 (d, J=9.0 Hz, 1H), 7.68-7.57 (m, 3H), 7.47 (d, J=3.5 Hz, 1H), 7.32 (d, J=8.4 Hz, 2H), 6.98 ((d, J=8.4 Hz, 2H), 6.62 (dd, J=9.0, 2.3 Hz, 1H), 6.48 (d, J=3.5 Hz, 1H), 6.13 (d, J=2.3 Hz, 1H), 3.57 (s, 2H), 3.56-2.71 (m, 8H), 2.36 (s, 2H), 2.24-2.14 (m, 2H), 1.96-1.71 (m, 8H).

Example 15

Bcl-2 and Bcl-xL Inhibition: Fluorescein labeled BIM (81-106), BAK (72-87), and BID (79-99) peptides, named as Flu-BIM, Flu-BAK, and Flu-BID, respectively, were used as the fluorescent probes in FP assays for Bcl-2, Bcl-xL, and Mcl-1, respectively. By monitoring the total fluorescence polarization values of mixtures composed of fluorescent probes at fixed concentrations and proteins with increasing concentrations up to the full saturation, the $K_d$ values of Flu-BIM to Bcl-2, Flu-BAK to Bcl-xL and Flu-BID to Mcl-1 were determined to be 0.55±0.15, 4.4±0.8 and 6.9±0.9 nM, respectively. Fluorescence polarization values were measured using the Infinite M-1000 plate reader (Tecan U.S., Research Triangle Park, N.C.) in Microfluor 1 96-well, black, round-bottom plates (Thermo Scientific). To each well, 1 nM of Flu-BIM, or 2 nM of Flu-BAK or 2 nM of Flu-BID and increasing concentrations of Bcl-2, or Bcl-xL, or Mcl-1 were added to a final volume of 125 μl in the assay buffer (100 mM potassium phosphate, pH 7.5, 100 μg/ml bovine γ-globulin, 0.02% sodium azide, Invitrogen, with 0.01% Triton X-100 and 4% DMSO). Plates were mixed and incubated at room temperature for 1 hour with gentle shaking to assure equilibrium. The polarization values in millipolarization units (mP) were measured at an excitation wavelength of 485 nm and an emission wavelength of 530 nm. Equilibrium dissociation constants ($K_d$) were then calculated by fitting the sigmoidal dose-dependent FP increases as a function of protein concentrations using Graphpad Prism 5.0 software (Graphpad Software, San Diego, Calif.).

$K_i$ values of representative Compounds of the Disclosure to Bcl-2, Bcl-xL, and Mcl-1 were determined from competitive binding experiments in which serial dilutions of inhibitors were added into 96-well plates containing fixed concentration of the fluorescent probes and proteins in each well. Mixtures of 5 μl of the tested inhibitors in DMSO and 120 μl of pre-incubated protein/probe complexes in the assay buffer were added into assay plates and incubated at room temperature for 2 hours with gentle shaking. Final concentrations of the protein and probe are 1.5 nM and 1 nM for the Bcl-2 assay, 10 nM and 2 nM for the Bcl-xL assay, and 20 nM and 2 nM for Mcl-1 assay, respectively. Negative controls containing protein/probe complex only (equivalent to 0% inhibition), and positive controls containing free probe only (equivalent to 100% inhibition), were included in each assay plate. FP values were measured as described above. IC$_{50}$ values were determined by nonlinear regression fitting of the competition curves. The $K_i$ values of competitive inhibitors were calculated using an equation described in Nikolovska-Coleska et al., Analytical Biochemistry 332: 261-73 (2004), based upon the measured IC$_{50}$ values, the $K_d$ values of the probes to the proteins, and the concentrations of the proteins and probes in the competitive assays. $K_i$ values were also calculated using the equation of Huang, Journal of Biomolecular Screening 8:34-38 (2003).

The inhibitory activities of representative Compounds of the Disclosure against Bcl-2, Bcl-xL, and Mcl-1 are provided in Table 4.

TABLE 4

| Cpd. No. | Inhibitory activity IC$_{50}$ (nM) | | |
|---|---|---|---|
| | Bcl-2 | Bcl-xL | Mcl-1 |
| 1 | 1.4 | 9.2 | |
| 2 | 0.76 | 10.6 | |
| 3 | 1.2 | 13.7 | |
| 4 | 3.1 | 8.6 | |
| 5 | 2.1 | 14 | |
| 6 | 2.0 | 5.9 | >5000 |
| 7 | 2.4 | 15.7 | |
| 8 | 2.4 | 6.4 | >5000 |
| 9 | 1.9 | 20.6 | |
| 10 | 3.3 | 14.0 | |
| 11 | 11.9 | 77.8 | |
| 12 | 4.4 | 139 | |
| 13 | 1.3 | 14.8 | |
| 58 | 3.8 | 19.2 | |
| 59 | 5.0 | 20.7 | |
| 60 | 2.1 | 67.5 | |
| 61 | 2.1 | 13.1 | |
| 62 | 1.6 | 4.0 | |
| 63 | 1.3 | 7.1 | |
| 64 | 2.4 | 8.7 | |
| 65 | 1.4 | 9.9 | |
| 66 | 2.7 | 12.0 | |

Example 16

RS4;11 Inhibition

RS4;11 cells were obtained from American Type Culture Collection (ATCC). They were used within three months of thawing fresh vials. Cells were maintained in the recommended culture medium with 10% FBS at 37° C. and an atmosphere of 5% $CO_2$.

The effect of representative Compounds of the Disclosure on cell viability was determined using Cell Counting Kit-8 (CCK-8) assay (Dojindo, Rockville, Md.) according to the manufacturer's instructions. 200 μL of a RS4;11 cell suspension (10000 cells/well) in culture medium were seeded into 96-well plates and cultured overnight. Each tested compound was serially diluted in culture medium, and 20 μL of the compound dilution was added to the corresponding well of the cell plate. After the addition of the tested compound, the cells were incubated at 37° C. in an atmosphere of 5% $CO_2$ for 4 days. At the end of 4 days, 10 μL of CCK-8 solution was added to each well of the plate and incubated for 1-4 hours. The plates were read at 450 nm on the microplate spectrophotometer (Epoch2, BioTek). The readings were normalized to the vehicle cells, and the $IC_{50}$ was calculated by nonlinear regression analysis using GraphPad Prism 5 software.

The inhibitory activities of representative Compounds of the Disclosure against the RS4;11 cell line are provided in Table 5.

TABLE 5

| Cpd. No. | RS4;11 $IC_{50}$ (nM) (Bcl-2 dependent) |
|---|---|
| 1 | 3 |
| 2 | 5.5 |
| 3 | 26 |
| 4 | 427 |
| 5 | 22 |
| 6 | 5.5 |
| 7 | 35 |
| 8 | 3.7 |
| 9 | 28 |
| 10 | 32 |
| 11 | 61 |
| 12 | 78 |
| 13 | 2.8 |
| 22 | 20 |
| 23 | 19 |
| 25 | 1,090 |
| 27 | 5.2 |
| 28 | 968 |
| 29 | 12 |
| 30 | 19 |
| 31 | 34 |
| 32 | 1,381 |
| 34 | 552 |
| 35 | 611 |
| 36 | 13 |
| 37 | 68 |
| 38 | 66 |
| 39 | 31 |
| 40 | 1.4 |
| 41 | 52 |
| 42 | 111 |
| 43 | 80 |
| 44 | 7,157 |
| 58 | 35 |
| 59 | 65 |
| 60 | 252 |
| 61 | 43 |
| 62 | 46 |

TABLE 5-continued

| Cpd. No. | RS4;11 $IC_{50}$ (nM) (Bcl-2 dependent) |
|---|---|
| 63 | 55 |
| 64 | 37 |
| 65 | 11 |
| 66 | 243 |

Example 17

Molm13 Inhibition

Molm13 cells were obtained from Deutsche Sammlung von Mikroorganismen and Zellkulturen GmbH (DSMZ). They were used within three months of thawing fresh vials. Cells were maintained in the recommended culture medium with 10% FBS at 37° C. and an atmosphere of 5% $CO_2$.

The effect of representative Compounds of the Disclosure on cell viability was determined using Cell Counting Kit-8 (CCK-8) assay (Dojindo, Rockville, Md.) according to the manufacturer's instructions. 200 μL of a Molm13 cell suspension (10000 cells/well) in culture medium were seeded into 96-well plates and cultured overnight. Each tested compound was serially diluted in culture medium, and 20 μL of the compound dilution was added to the corresponding well of the cell plate. After the addition of the tested compound, the cells were incubated at 37° C. in an atmosphere of 5% $CO_2$ for 4 days. At the end of 4 days, 10 μL of CCK-8 solution was added to each well of the plate and incubated for 1-4 hours. The plates were read at 450 nm on the microplate spectrophotometer (Epoch2, BioTek). The readings were normalized to the vehicle cells, and the $IC_{50}$ was calculated by nonlinear regression analysis using GraphPad Prism 5 software.

The inhibitory activities of representative Compounds of the Disclosure against the Molm13 cell line are provided in Table 6.

TABLE 6

| Cpd. No. | Molm13 $IC_{50}$ (nM) (Bcl-2 dependent) |
|---|---|
| 1 | 47 |
| 2 | 85 |
| 6 | 6.4 |
| 10 | 182 |
| 11 | 1,024 |
| 12 | 253 |
| 13 | 1.8 |
| 58 | 250 |
| 59 | 468 |

Example 18

RS4;11 Xenograft Model

Figure 2:
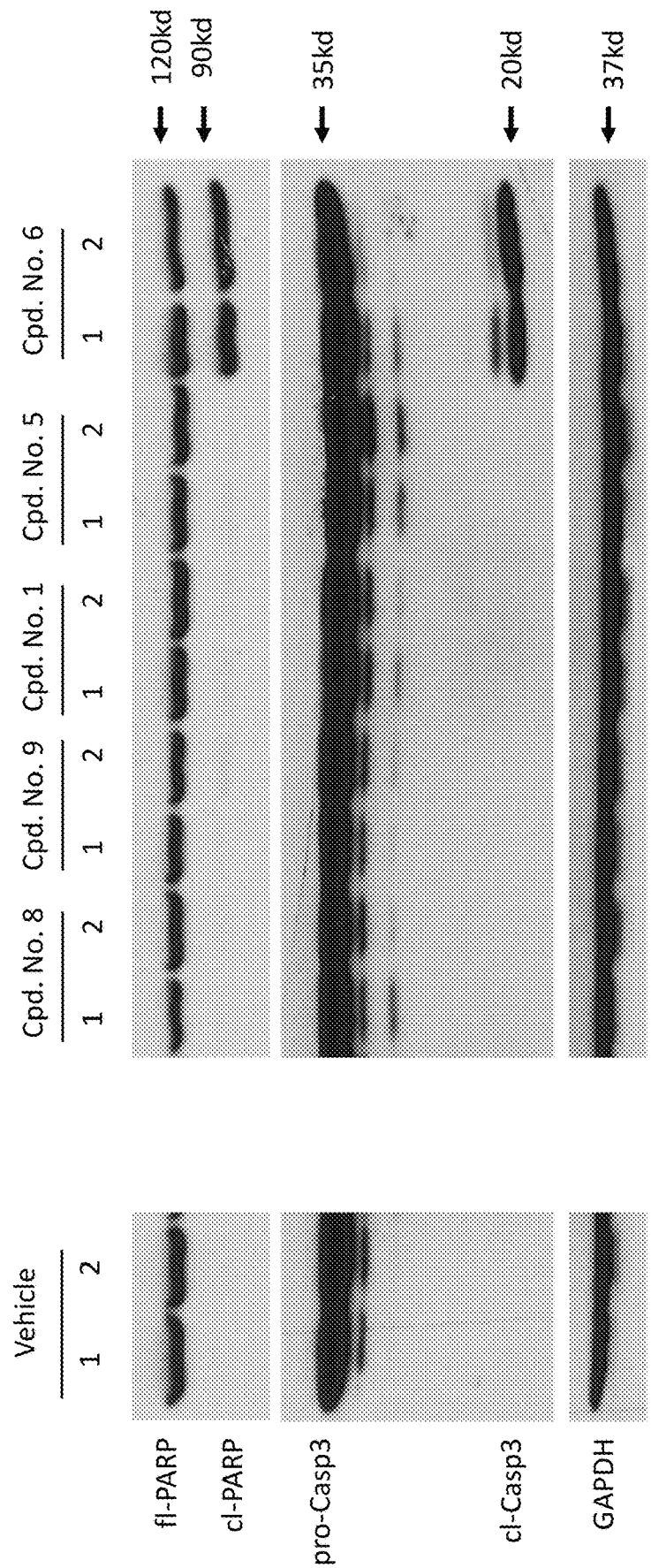
FIG. 2 is an illustration (Western blotting analysis) showing the expression of PARP and caspase-3 in RS4;11 xenograft tumor tissues obtained from mice following administration of Compounds of the Disclosure.

RS4;11 xenograft tumor tissues obtained from mice treated with Compounds of the Disclosure or ABT-199 at 25 mg/kg po, were examined for the expression of PARP, (Cell Signaling Technology (CST), #9523) caspase-3 (CST, #9661), and Bcl-2 (CST, #4223) by western blotting analysis. GAPDH was used as a loading control. The results are shown in FIG. 1 and FIG. 2.

Figure 3:
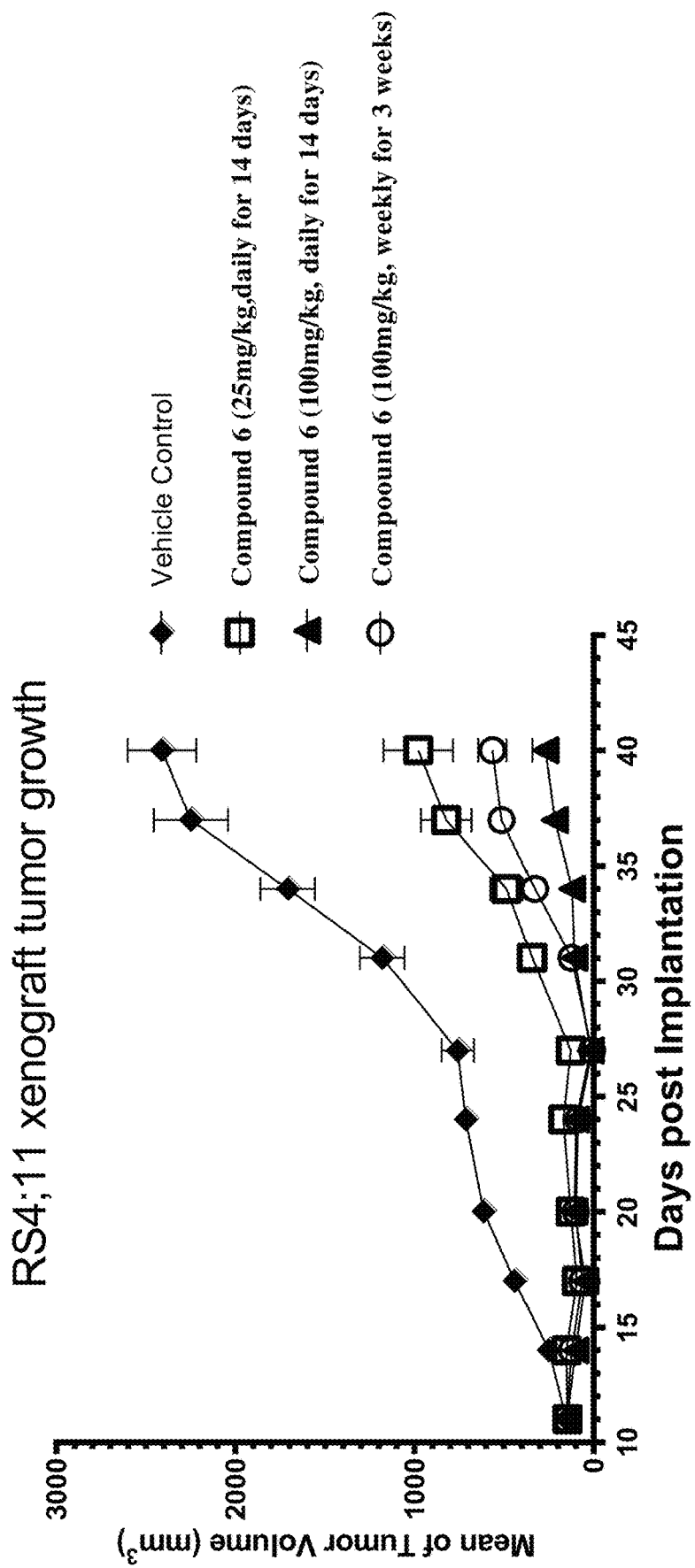
FIG. 3 is a line graph showing the antitumor activity of Cpd. No. 6 in the RS4;11 leukemia xenograft model.

The antitumor activity of Cpd. No. 6 (compound 6) was also studied in the RS4;11 leukemia xenograft model. Human RS4;11 tumor cells were injected into nude mice and treatment started on day 11 when the tumor size reached approximately 100 mm³. Cpd. No. 6 was administered via oral gavage at indicated doses and schedules. Cpd. No. 6 inhibits tumor growth (FIG. 3) and does not cause weight loss in mice (FIG. 4).

Example 19

Pharmacokinetics

The pharmacokinetics of ABT-199 and representative Compounds of the Disclosure were evaluated in rats at an IV dose of 2 mg/kg and an oral dose of 20 mg/kg. The results are shown in Table 3.

TABLE 3

| Compound | Tmax (h) | | Cmax(ng/mL) | | AUC0-t (ng·h/mL) | | AUC0-∞ (ng·h/mL) | | $t_{1/2}$ (h) | | CL (iv) (L/h/kg) | $V_{ss}$ (iv) (L/kg) | $MRT_{INF}$ (iv)(h) | F(AUC0-t) |
|---|---|---|---|---|---|---|---|---|---|---|---|---|---|---|
| | IV | PO | IV | PO | IV | PO | IV | PO | IV | PO | | | | |
| ABT-199 | 0.083 | 1.67 | 8737 | 5999 | 5435 | 20786 | 5446 | 20812 | 4.32 | 3.22 | 0.394 | 0.496 | 1.23 | 38.2% |
| Cpd. No. 3 | 0.083 | 2.00 | 4202 | 1318 | 2656 | 7630 | 2683 | 7775 | 4.94 | 4.46 | 0.769 | 1.86 | 2.37 | 29.0% |
| Cpd. No. 6 | 0.083 | 2.67 | 4174 | 2623 | 2899 | 13424 | 2915 | 13475 | 4.39 | 3.12 | 0.695 | 1.44 | 2.09 | 46.2% |

Example 20

MV4;11 Inhibition

The inhibitory activities of representative Compounds of the Disclosure against the MV4;11 cell line are provided in Table 7.

TABLE 7

| Cpd. No. | MV4;11 IC$_{50}$ (µM) |
|---|---|
| 22 | 0.05894 |
| 23 | 0.05457 |
| 24 | 243.0 |
| 25 | 5.154 |
| 26 | 6.711 |
| 27 | 0.01694 |
| 28 | 1.295 |
| 29 | 0.04819 |
| 30 | 0.02249 |
| 31 | 0.1161 |
| 34 | 5.674 |
| 35 | 3.598 |
| 36 | 0.04444 |
| 37 | 0.1544 |
| 38 | 0.1030 |
| 39 | 0.03374 |
| 40 | 0.002455 |
| 41 | 0.01811 |
| 42 | 0.08810 |
| 43 | 0.1260 |
| 66 | >1000 |

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound, or a pharmaceutically acceptable salt thereof, having Formula I-A:

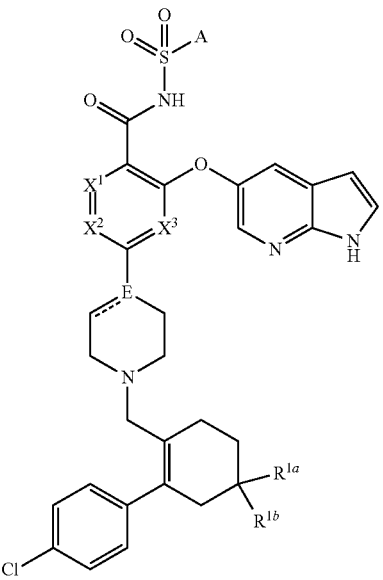

I-A wherein:
A is selected from the group consisting of:

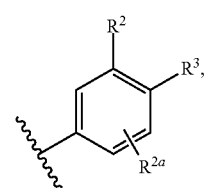

A-1

-continued

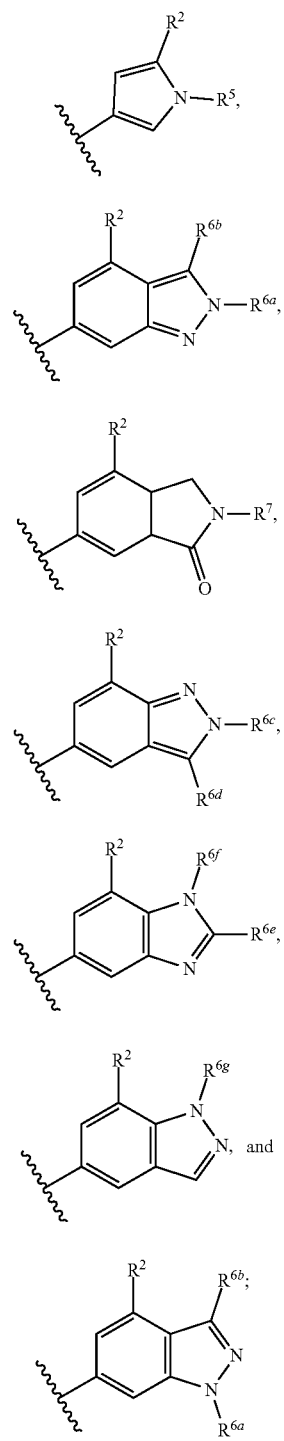

E is a carbon atom and the depicted dashed bond forms a double bond; or

E is a —C(H)— and the depicted dashed bond is absent to form a single bond; or

E is a nitrogen atom and the depicted dashed bond is absent to form a single bond;

$X^1$, $X^2$, and $X^3$ are each —$CR^8$=, or one of $X^1$, $X^2$, and $X^3$ is —N= and two $X^1$, $X^2$, and $X^3$ are each —$CR^8$;

$R^{1a}$ and $R^{1b}$ taken together with the carbon atom to which they are attached form

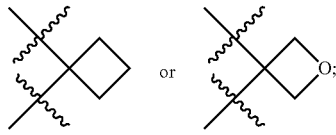 [SMILES: *C1(*)CCC1 ; *C1(*)COC1]

$R^2$ is selected from the group consisting of —$NO_2$, —$SO_2CH_3$, and —$SO_2CF_3$;

$R^3$ is selected from the group consisting of hydrogen, —CN, —C≡CH, and —$N(R^{4a})(R^{4b})$;

$R^{2a}$ is selected from the group consisting of hydrogen and halogen;

$R^{4a}$ is selected from the group consisting of optionally substituted $C_{1-6}$ alkyl, optionally substituted $C_{3-6}$ cycloalkyl, optionally substituted heterocyclo, optionally substitute heteroalkyl, optionally substituted (cycloalkyl)alkyl, and optionally substituted (heterocyclo)alkyl;

$R^{4b}$ is selected from the group consisting of hydrogen and $C_{1-4}$ alkyl;

$R^5$ is selected from the group consisting of is selected from the group consisting of optionally substituted $C_{1-6}$ alkyl, optionally substituted heterocyclo, optionally substituted heteroalkyl, optionally substituted (cycloalkyl)alkyl, and optionally substituted (heterocyclo)alkyl;

$R^{6a}$, $R^{6c}$, $R^{6e}$, $R^{6f}$, and $R^{6g}$ are each independently selected from the group consisting of hydrogen, optionally substituted $C_{1-6}$ alkyl, optionally substituted $C_{3-6}$ cycloalkyl, optionally substituted aryl, optionally substituted heteroaryl, optionally substituted heterocyclo, optionally substituted heteroalkyl, optionally substituted (cycloalkyl)alkyl, and optionally substituted (heterocyclo)alkyl;

$R^{6b}$ and $R^{6d}$ are each independently selected from the group consisting of hydrogen, $C_{1-4}$ alkyl, and halogen;

$R^7$ is selected from the group consisting of optionally substituted $C_{1-6}$ alkyl, optionally substituted heterocyclo, optionally substituted heteroalkyl, optionally substituted (cycloalkyl)alkyl, and optionally substituted (heterocyclo)alkyl; and $R^8$ is selected from the group consisting of hydrogen and halogen.

2. The compound of claim 1, wherein A is

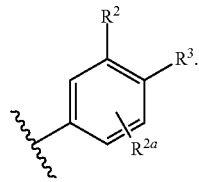

3. The compound of claim 2, wherein $R^2$ is —$NO_2$.

4. The compound of claim 2, wherein $R^3$ is —$N(R^{4a})(R^{4b})$.

5. The compound of claim 4, wherein $R^{4a}$ is selected from the group consisting of optionally substituted $C_{1-6}$ alkyl, optionally substituted $C_{3-6}$ cycloalkyl, optionally substituted heterocyclo, optionally substituted heteroalkyl, optionally substituted (cycloalkyl)alkyl, and optionally substituted (heterocyclo)alkyl; and Rob is hydrogen.

6. The compound of claim 5, wherein $R^{4a}$ is selected from the group consisting of optionally substituted (heterocyclo)alkyl.

7. The compound of claim 2, wherein $R^{2a}$ is hydrogen.

8. The compound of claim 2, wherein $R^{2a}$ is fluorine.

9. The compound of claim 1, wherein $R^{1a}$ and $R^{1b}$ taken together with the carbon atom to which they are attached form (i) —CH$_2$—CH$_2$—CH$_2$—; or (ii) —CH$_2$—O—CH$_2$—.

10. The compound of claim 1, wherein E is a carbon atom and the depicted dashed bond forms a double bond.

11. The compound of claim 1, wherein E is —C(H)— and the depicted dashed bond is absent to form a single bond.

12. The compound of claim 1, wherein E is a nitrogen atom and the depicted dashed bond is absent to form a single bond.

13. The compound of claim 1, wherein $X^1$, $X^2$, and $X^3$ are each independently selected from the group consisting of —CR$^8$=.

14. The compound of claim 13, wherein $R^8$ is hydrogen.

15. A pharmaceutical composition comprising the compound of claim 1 and a pharmaceutically acceptable carrier.

16. A method of treating a patient, the method comprising administering to the patient a therapeutically effective amount of the compound of claim 1, wherein the patient has a cancer selected from the group consisting of acute monocytic leukemia, acute myelogenous leukemia, chronic myelogenous leukemia, chronic lymphocytic leukemia mixed lineage leukaemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

* * * * *